US010092624B2

(12) United States Patent
Gourdie et al.

(10) Patent No.: US 10,092,624 B2
(45) Date of Patent: *Oct. 9, 2018

(54) METHODS OF TREATING CANCERS WITH PEPTIDE-BASED MODULATORS

(71) Applicants: MUSC FOUNDATION FOR RESEARCH DEVELOPMENT, Charleston, SC (US); UNIVERSITY OF SOUTH CAROLINA, Columbia, SC (US)

(72) Inventors: Robert G. Gourdie, Roanoke, VA (US); Edie C. Goldsmith, Columbia, SC (US); L. Jane Jourdan, Roanoke, VA (US); Joshua Matthew Rhett, Charleston, SC (US); Michael J. Yost, Charleston, SC (US)

(73) Assignees: MUSC Foundation for Research Development, Charleston, SC (US); University of South Carolina, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/135,780

(22) Filed: Apr. 22, 2016

(65) Prior Publication Data

US 2016/0287663 A1    Oct. 6, 2016

Related U.S. Application Data

(63) Continuation of application No. 14/396,571, filed as application No. PCT/US2013/038207 on Apr. 25, 2013, now Pat. No. 9,345,744.

(60) Provisional application No. 61/638,094, filed on Apr. 25, 2012.

(51) Int. Cl.

| | |
|---|---|
| A61L 27/22 | (2006.01) |
| C08L 77/04 | (2006.01) |
| A61P 35/04 | (2006.01) |
| A61K 38/17 | (2006.01) |
| C07K 7/08 | (2006.01) |
| A61L 27/34 | (2006.01) |
| A61L 27/54 | (2006.01) |
| A61L 31/04 | (2006.01) |
| A61L 31/10 | (2006.01) |
| A61L 31/16 | (2006.01) |
| A61L 15/32 | (2006.01) |
| A61L 15/44 | (2006.01) |
| A61L 17/00 | (2006.01) |
| A61K 9/00 | (2006.01) |
| A61K 47/10 | (2017.01) |
| C07K 14/47 | (2006.01) |
| A61K 38/08 | (2006.01) |
| A61K 38/10 | (2006.01) |
| A61K 45/06 | (2006.01) |
| C07K 7/06 | (2006.01) |
| C07K 14/46 | (2006.01) |
| A61K 38/00 | (2006.01) |

(52) U.S. Cl.
CPC ........ *A61K 38/1703* (2013.01); *A61K 9/0048* (2013.01); *A61K 38/08* (2013.01); *A61K 38/10* (2013.01); *A61K 45/06* (2013.01); *A61K 47/10* (2013.01); *A61L 15/32* (2013.01); *A61L 15/44* (2013.01); *A61L 17/005* (2013.01); *A61L 27/22* (2013.01); *A61L 27/34* (2013.01); *A61L 27/54* (2013.01); *A61L 31/047* (2013.01); *A61L 31/10* (2013.01); *A61L 31/16* (2013.01); *C07K 7/06* (2013.01); *C07K 7/08* (2013.01); *C07K 14/46* (2013.01); *C07K 14/47* (2013.01); *C07K 14/4703* (2013.01); *A61K 38/00* (2013.01); *A61L 2300/25* (2013.01); *A61L 2300/252* (2013.01); *A61L 2300/412* (2013.01); *A61L 2430/16* (2013.01); *C07K 2319/035* (2013.01)

(58) Field of Classification Search
None
See application file for complete search history.

(56) References Cited

U.S. PATENT DOCUMENTS

| | | |
|---|---|---|
| 7,786,074 B2 | 8/2010 | Gourdie et al. |
| 2005/0100999 A1 | 5/2005 | Yokota |
| 2010/0286762 A1 | 11/2010 | Gourdie et al. |
| 2011/0086068 A1 | 4/2011 | Gourdie et al. |
| 2011/0130345 A1 | 6/2011 | Rohrer et al. |
| 2011/0195911 A1 | 8/2011 | Tarasova et al. |

FOREIGN PATENT DOCUMENTS

| | | |
|---|---|---|
| WO | WO 2006/069181 | 6/2006 |
| WO | WO 2006/134494 | 12/2006 |
| WO | WO 2008/157840 | 12/2008 |
| WO | WO 2009/075881 | 6/2009 |
| WO | WO 2011/016861 | 2/2011 |
| WO | WO 2012/019192 | 2/2012 |

OTHER PUBLICATIONS

Gura, T. Science (1997), 278(5340); pp. 1041-1042.*
Kamb, A. Nat. Rev. Drug Discov. (2005), 4(2); pp. 161-165.*

(Continued)

*Primary Examiner* — Kevin S Orwig
(74) *Attorney, Agent, or Firm* — Parker Highlander PLLC

(57) ABSTRACT

Provided are peptides that can inhibit collagen synthesis, processing and/or secretion. In some aspects, the therapeutic peptides may be used to treat a cancer such as, e.g., a pancreatic cancer or a glioblastoma.

22 Claims, 17 Drawing Sheets

Specification includes a Sequence Listing.

(56) References Cited

OTHER PUBLICATIONS

Roberts, T. G., et al. JAMA. (2004), 292(17); pp. 2130-2140.*
Oyamada, M., et al. Biochim. Biophys. Acta. (2005), 1719(1-2); pp. 6-23.*
Montecino-Rodriguez, E., et al. Blood (2000), 96(3); 917-924.*
Zhang, A., et al. Oncotarget Advance Pubs. (2015), pp. 1-12; www.impactjournals.com/oncotarget.*
Human Protein Atlas entry for GJA1 (Cx43) (https://www.proteinatlas.org/ ENSG00000152661-GJA1/tissue; accessed online Jan. 30, 2018).*
"Connexin 47 [Mesocricetus auratus]," NCBI Genbank Accession No. AAM34255.1, May 22, 2002.
"Gap junction protein alpha 1 [Felis catus]," NCBI GenBank Accession No. ADM89621.1, Sep. 11, 2010.
Eltzschig et al., "TP release from activated neutrophils occurs via connexin 43 and modulates adenosine-dependent endothelial cell function," *Cir. Res.*, 99(10):1100-1108, 2006.
Francis et al., "A hierarchy of signals regulates entry of membrane proteins into the ciliary membrane domain in epithelial cells," *J. Cell. Biol.*, 193(1):219-233, 2011.
Fu et al., "CCN3 (NOV) interacts with connexin43 in C6 glioma cells: possible mechanism of connexin-mediated growth suppression," *J. Biol. Chem.*, 279(35):36943-36950, 2004.
Gao et al., "A cell-penetrating peptide from a novel pVII-pIX phage-displayed random peptide library," *Bioorg. Med. Chem.*, 10(12):4057-4065, 2002.
Goodenough and Paul, "Beyond the gap: functions of unpaired connexon channels," *Nat. Rev. Mol. Cell Biol.*, 4(4):285-294, 2003.
Gresh et al., "Structure-function analysis of rods and cones in juvenile, adult, and aged C57bl/6 and Balb/c mice," *Vis. Neurosci.*, 20(2):211-220, 2003.
Hong and Clayman, "Isolation of a peptide for targeted drug delivery into human head and neck solid tumors," *Cancer Res.*, 60:6551-6556, 2000.
Huang et al., "Critical role of connexin 43 in secondary expansion of traumatic spinal cord injury," *J. Neurosci.*, 32(10):3333-3338, 2012.
Hunter et al., "Zonula occludens-1 alters connexin43 gap junction size and organization by influencing channel accretion," *Mol. Biol. Cell*, 16(12):5686-5698, 2005.
Lu et al., "ATP released from cardiac fibroblasts via connexin hemichannels activates profibrotic P2Y2 receptors," *FASEB J.*, 26(6):2580-2591, 2012. Published online before print on Mar. 13, 2012.
Lundberg et al., "Cell membrane translocation of the N-terminal (1-28) part of the prion protein," *Biochem. Biophys. Res. Comm.*, 299(1), 85-90, 2002.
Morris et al.,"A peptide carrier for the delivery of biologically active proteins into mammalian cells," *Nat. Biotechnol.*, 19(12):1173-1176, 2001.
Notice of Allowance issued in U.S. Appl. No. 14/396,571, dated Jan. 29, 2016.
Palatinus et al., "Translational lessons from scarless healing of cutaneous wounds and regenerative repair of the myocardium," *Journal of Molecular and Cellular Cardiology*, 48(3):550-557, 2009.
PCT International Search Report and Written Opinion issued in International Patent Application No. PCT/US2013/038207, dated Jul. 29, 2013.
Rouselle et al., "New advances in the transport of doxorubicin through the blood-brain barrier by a peptide vector-mediated strategy," *Mol. Pharmacol.*, 57:679-686, 2000.
Sawada et al., "Cytoprotective membrane-permeable peptides designed from the Bax-binding domain of Ku70," *Nature Cell Biol.*, 5(4):352-357, 2003.
Soder et al., "The connexin43 carboxyl-terminal peptide ACT1 modulates the biological response to silicone implants," *Plast. Reconstr. Surg.*, 123(5):1440-1451, 2009.
Toyofuku et al., Direct association of the gap junction protein connexin-43 with ZO-1 in cardiac myocytes, *J. Biol. Chem.*, 273(21):12725-12731, 1998.
Jaraíz-Rodríguez et al., "A short region of connexin43 reduces human glioma stell cell migration, invasion, and survival through Src, PTEN, and FAK," *Stem Cell Reports*, 9:451-463, 2017.
Lamouille et al., "Abstract 4765: Targeting glioblastoma cancer stem cells with a novel Connexin43 mimetic peptide," In: Proceedings of the American Association for Cancer Research Annual Meeting 2017, *Cancer Res.*, 77(Suppl. 13), Abstract No. 4765, 2017.
Leithe et al., "The connexin 43 C-terminus: A tail of many tales," *Biochimica et Biophysica Acta*, 17 pages, http://dx.doi.org/10.1016/j.bbamem.2017.05.008, available online May 16, 2017.
Rhett et al., "Mechanism of action of the anti-inflammatory connexin43 mimetic peptide JM2," *Am. J Physiol. Cell Physiol.*, 313:C314-C326, 2017.
Tabernero et al., "The role of connexin43-Src interaction in astrocytomas: A molecular puzzle," *Neuroscience*, 323:183-194, 2016.
Zhu et al., "ACT1 Peptide Modulates Glioma Cell Invasiveness," Presented at: 2007 Pediatric Academic Societies' Annual Meeting, Toronto, Canada, May 6, 2007.

* cited by examiner

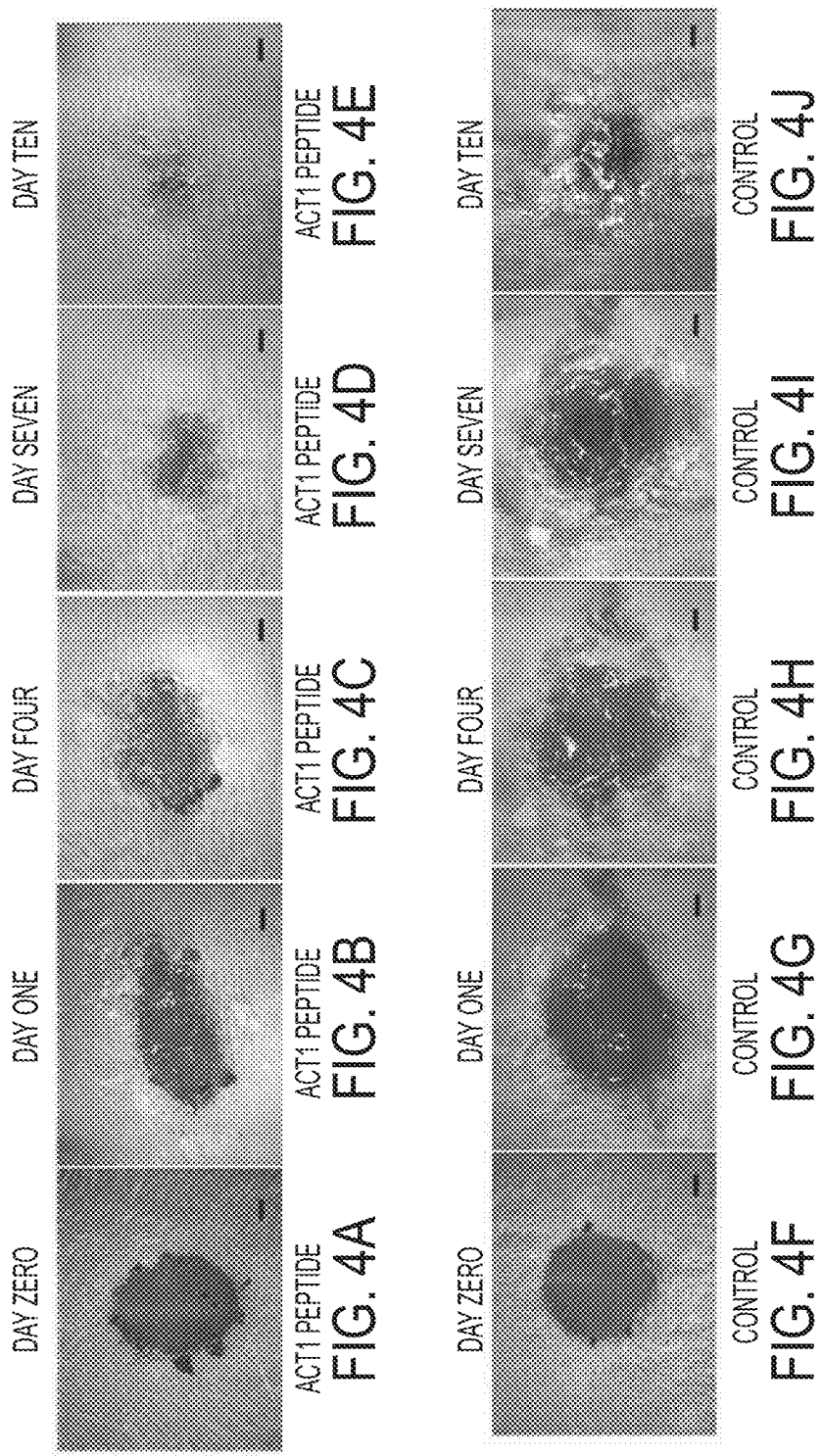

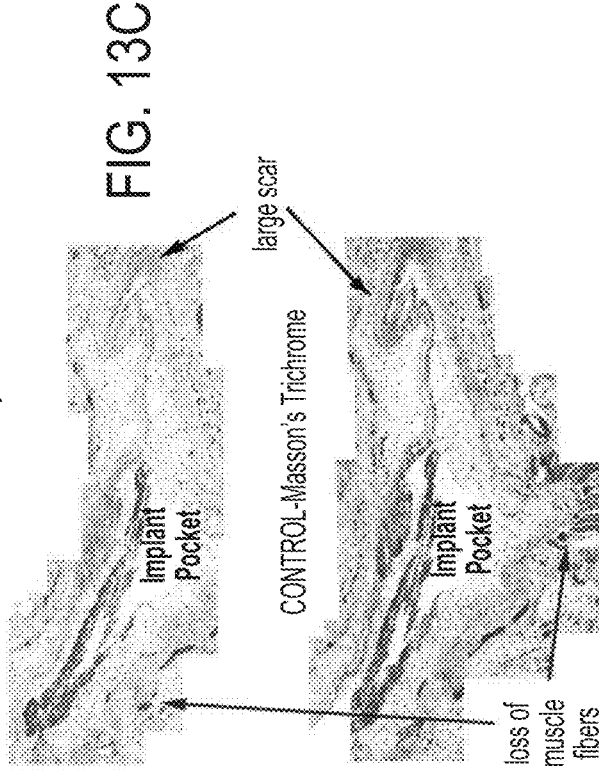
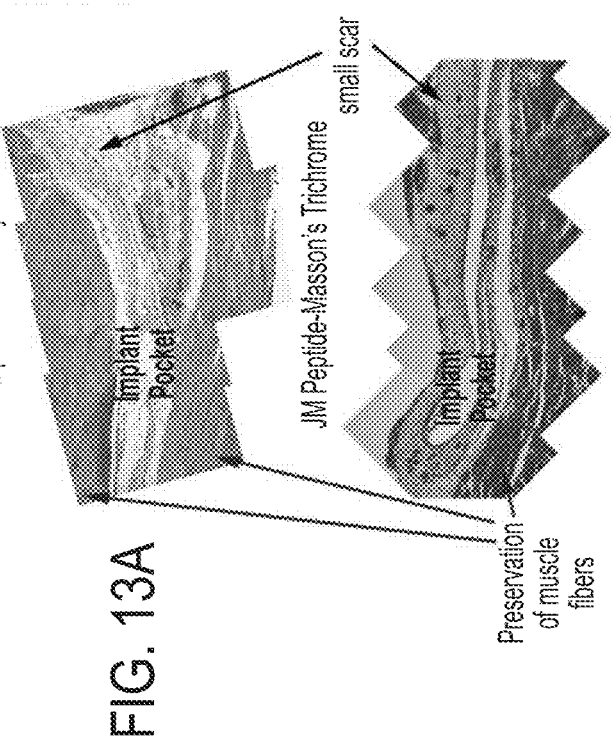
FIG. 13A  FIG. 13B  FIG. 13C  FIG. 13D

SEQUENCE LISTING

<160> NUMBER OF SEQ ID NOS: 66

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Val Phe Phe Lys Gly Val Lys Asp Arg Val
1               5                   10

<210> SEQ ID NO 2
<211> LENGTH: 15

```
<212> TYPE: PRT
<213> ORGANISM: Artificial Sequence
<220> FEATURE:
<223> OTHER INFORMATION: Synthetic peptide

<400> SEQUENCE: 2

Val Phe Phe Lys Gly Val Lys Asp Arg Val Lys Gly Arg Ser Asp
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Arg Arg Arg Arg Arg Arg Arg Arg
1               5

<210> SEQ ID NO 4
<211> LENGTH: 23
<212> TYPE: PRT
<213> ORGANISM: Artificial Sequence
<220> FEATURE:
<223> OTHER INFORMATION: Synthetic peptide

<400> SEQUENCE: 4

Arg Arg Arg Arg Arg Arg Arg Arg Val Phe Phe Lys Gly Val Lys Asp
1               5                   10                  15

Arg Val Lys Gly Arg Ser Asp
            20

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide

<400> SEQUENCE: 5

Arg Arg Arg Arg Arg Arg Arg Arg Val Phe Phe Lys Gly Val Lys Asp
1               5                   10                  15

Arg Val

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Val Phe Phe Lys Gly Val Lys Asp Arg Val Lys Gly Lys Ser Asp
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Val Phe Phe Lys Gly Val Lys Asp Arg Val
1               5                   10
```

```
<210> SEQ ID NO 8
<211> LENGTH: 23
<212> TYPE: PRT
<213> ORGANISM: Artificial Sequence
<220> FEATURE:
<223> OTHER INFORMATION: Synthetic peptide

<400> SEQUENCE: 8

Arg Arg Arg Arg Arg Arg Arg Arg Val Phe Phe Lys Gly Val Lys Asp
1               5                   10                  15

Arg Val Lys Gly Arg Ser Asp
            20

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Arg Arg Arg Arg Arg Arg Arg Arg Val Phe Phe Lys Gly Val Lys Asp
1               5                   10                  15

Arg Val

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Val Phe Phe Lys Gly Val Lys Asp Arg Val Lys Gly Arg Ser Asp
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

Val Phe Phe Lys Gly Val Lys Asp Arg Val Lys Gly Arg Ser Asp Pro
1               5                   10                  15

Tyr His Ala Thr
            20

<210> SEQ ID NO 12
<211> LENGTH: 15
<212> TYPE: PRT
<213> ORGANISM: Homo sapiens

<400> SEQUENCE: 12

Val Phe Phe Lys Gly Val Lys Asp Arg Val Lys Gly Lys Ser Asp
1               5                   10                  15

<210> SEQ ID NO 13
<211> LENGTH: 15
<212> TYPE: PRT
<213> ORGANISM: Mus musculus

<400> SEQUENCE: 13
```

Val Phe Phe Lys Gly Val Lys Asp Arg Val Lys Gly Arg Ser Asp
1               5                   10                  15

<210> SEQ ID NO 14
<211> LENGTH: 15
<212> TYPE: PRT
<213> ORGANISM: Canis lupus

<400> SEQUENCE: 14

Val Phe Phe Lys Gly Val Lys Asp Arg Val Lys Gly Gln Ser Asp
1               5                   10                  15

<210> SEQ ID NO 15
<211> LENGTH: 15
<212> TYPE: PRT
<213> ORGANISM: Gallus gallus

<400> SEQUENCE: 15

Val Phe Phe Lys Gly Val Lys Asp Arg Val Lys Gly Lys Thr Asp
1               5                   10                  15

<210> SEQ ID NO 16
<211> LENGTH: 15
<212> TYPE: PRT
<213> ORGANISM: Danio rerio

<400> SEQUENCE: 16

Val Leu Phe Lys Arg Ile Lys Asp Arg Val Lys Ser Arg Gln Asn
1               5                   10                  15

<210> SEQ ID NO 17
<211> LENGTH: 15
<212> TYPE: PRT
<213> ORGANISM: Danio rerio

<400> SEQUENCE: 17

Val Ile Phe Lys Arg Met Lys Asp Gln Ile Arg Glu Ser Glu Lys
1               5                   10                  15

<210> SEQ ID NO 18
<211> LENGTH: 15
<212> TYPE: PRT
<213> ORGANISM: Canis lupus

<400> SEQUENCE: 18

Val Phe Phe Lys Gly Val Lys Asp Arg Val Lys Gly Gln Ser Asp
1               5                   10                  15

<210> SEQ ID NO 19
<211> LENGTH: 15
<212> TYPE: PRT
<213> ORGANISM: Cricetulus griseus

<400> SEQUENCE: 19

Val Phe Phe Lys Gly Ile Lys Asp Arg Val Lys Gly Arg Asn Asp
1               5                   10                  15

<210> SEQ ID NO 20
<211> LENGTH: 15
<212> TYPE: PRT
<213> ORGANISM: Ornithorhynchus anatinus

<400> SEQUENCE: 20

Val Phe Phe Lys Gly Val Lys Asp Arg Val Lys Gly Arg Ile Asp

```
<210> SEQ ID NO 21
<211> LENGTH: 15
<212> TYPE: PRT
<213> ORGANISM: Erinaceus europaeus

<400> SEQUENCE: 21

Val Phe Phe Lys Gly Ile Lys Asp Arg Val Lys Gly Lys Ser Asp
1               5                   10                  15

<210> SEQ ID NO 22
<211> LENGTH: 14
<212> TYPE: PRT
<213> ORGANISM: Sus scrofa

<400> SEQUENCE: 22

Phe Phe Lys Gly Val Lys Asp Arg Val Lys Gly Lys Ser Asp
1               5                   10

<210> SEQ ID NO 23
<211> LENGTH: 13
<212> TYPE: PRT
<213> ORGANISM: Cynops pyrrhogaster

<400> SEQUENCE: 23

Phe Lys Ser Val Lys Asp Arg Ile Lys Gly Arg Ser Asp
1               5                   10

<210> SEQ ID NO 24
<211> LENGTH: 15
<212> TYPE: PRT
<213> ORGANISM: Oryctolagus cuniculus

<400> SEQUENCE: 24

Val Phe Phe Arg Ser Val Lys Asp His Val Lys Gly Lys Ser Asp
1               5                   10                  15

<210> SEQ ID NO 25
<211> LENGTH: 12
<212> TYPE: PRT
<213> ORGANISM: Oreochromis aureus

<400> SEQUENCE: 25

Val Phe Phe Lys Arg Ile Lys Asp Arg Val Lys Gly
1               5                   10

<210> SEQ ID NO 26
<211> LENGTH: 13
<212> TYPE: PRT
<213> ORGANISM: Carassius auratus

<400> SEQUENCE: 26

Val Leu Phe Lys Gln Ile Lys Asp Arg Val Lys Gly Arg
1               5                   10

<210> SEQ ID NO 27
<211> LENGTH: 13
<212> TYPE: PRT
<213> ORGANISM: Cyprinus carpio

<400> SEQUENCE: 27

Val Leu Phe Lys Arg Ile Lys Asp Arg Val Lys Gly Arg
1               5                   10
```

```
<210> SEQ ID NO 28
<211> LENGTH: 11
<212> TYPE: PRT
<213> ORGANISM: Artificial Sequence
<220> FEATURE:
<223> OTHER INFORMATION: Synthetic peptide

<400> SEQUENCE: 28

Phe Glu Val Ala Phe Leu Leu Ile Gln Trp Ile
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide

<400> SEQUENCE: 29

Leu Leu Ile Gln Trp Tyr Ile Gly Phe Ser Leu
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Synthetic peptide

<400> SEQUENCE: 30

Ser Leu Ser Ala Val Tyr Thr Cys Lys Arg Asp Pro Cys Pro His Gln
1               5                   10                  15

Glu

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31

Val Asp Cys Phe Leu Ser Arg Pro Thr Glu Lys Thr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide

<400> SEQUENCE: 32

Ser Arg Pro Thr Glu Lys Thr Ile Phe Ile Ile
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic peptide

<400> SEQUENCE: 33

Leu Gly Thr Ala Val Glu Ser Ala Trp Gly Asp Glu Gln
1               5                   10
```

<210> SEQ ID NO 34
<211> LENGTH: 12
<212> TYPE: PRT
<213> ORGANISM: Artificial Sequence
<220> FEATURE:
<223> OTHER INFORMATION: Synthetic peptide

<400> SEQUENCE: 34

Gln Ser Ala Phe Arg Cys Asn Thr Gln Gln Pro Gly
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic peptide

<400> SEQUENCE: 35

Gln Gln Pro Gly Cys Glu Asn Val Cys Tyr Asp Lys Glu
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic peptide

<400> SEQUENCE: 36

Val Cys Tyr Asp Lys Ser Phe Pro Ile Ser His Val Arg Glu
1               5                   10

<210> SEQ ID NO 37
<211> LENGTH: 13
<212> TYPE: PRT
<213> ORGANISM: Oreochromis aureus

<400> SEQUENCE: 37

Val Phe Phe Lys Arg Ile Lys Asp Arg Val Lys Gly Lys
1               5                   10

<210> SEQ ID NO 38
<211> LENGTH: 11
<212> TYPE: PRT
<213> ORGANISM: Taylorella equigenitalis

<400> SEQUENCE: 38

Val Phe Phe Lys Gly Ile Phe Gln Lys Asp Arg
1               5                   10

<210> SEQ ID NO 39
<211> LENGTH: 10
<212> TYPE: PRT
<213> ORGANISM: Dictyostelium discoideum

<400> SEQUENCE: 39

Ile Phe Phe Arg Val Lys Asp Arg Val Lys
1               5                   10

<210> SEQ ID NO 40
<211> LENGTH: 12
<212> TYPE: PRT
<213> ORGANISM: Bacteroides splanchnicus

```
<400> SEQUENCE: 40

Val Phe Phe Asp Glu Leu Lys Asp Arg Val Lys Gly
1               5                   10

<210> SEQ ID NO 41
<211> LENGTH: 12
<212> TYPE: PRT
<213> ORGANISM: Bacillus cereus

<400> SEQUENCE: 41

Ile Phe Phe Lys Ser Val Lys Arg Ile Lys Gly Lys
1               5                   10

<210> SEQ ID NO 42
<211> LENGTH: 11
<212> TYPE: PRT
<213> ORGANISM: Fusobacterium nucleatum

<400> SEQUENCE: 42

Gly Phe Phe Lys Gly Val Lys Asp Lys Val Lys
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide

<400> SEQUENCE: 43

Val Phe Phe Lys Gly Val Arg Asp Lys Val Lys Gly Lys Thr Asp
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide

<400> SEQUENCE: 44

Val Phe Phe Lys Gly Val Lys Asp Arg Val Lys Gly Lys Ser Asp
1               5                   10                  15

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide

<400> SEQUENCE: 45

Val Phe Phe Lys Gly Val Lys Asp Arg Val
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Synthetic peptide

<400> SEQUENCE: 46

Ile Phe Phe Lys Gly Val Lys Asp Arg Val Lys Gly Lys Ser Asp
1               5                   10                  15
```

```
<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Ile Phe Phe Lys Gly Val Lys Asp Arg Val
1               5                   10

<210> SEQ ID NO 48
<211> LENGTH: 15
<212> TYPE: PRT
<213> ORGANISM: Artificial Sequence
<220> FEATURE:
<223> OTHER INFORMATION: Synthetic peptide

<400> SEQUENCE: 48

Val Ile Phe Lys Arg Met Lys Asp Gln Ile Arg Glu Ser Glu Lys
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic peptide

<400> SEQUENCE: 49

Val Phe Phe Lys Gly Val Lys Asp Arg Val Lys Gly Lys Thr Asp
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic peptide

<400> SEQUENCE: 50

Val Phe Phe Lys Gly Val Lys Asp Arg Val Lys Gly Arg Ser Asp
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic peptide

<400> SEQUENCE: 51

Val Phe Phe Lys Gly Val Lys Asp Arg Val Arg Gly Lys Ser Asp
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide

<400> SEQUENCE: 52

Val Phe Phe Lys Gly Val Lys Asp Lys Val Lys Gly Lys Ser Asp
1               5                   10                  15
```

```
<210> SEQ ID NO 53
<211> LENGTH: 15
<212> TYPE: PRT
<213> ORGANISM: Artificial Sequence
<220> FEATURE:
<223> OTHER INFORMATION: Synthetic peptide

<400> SEQUENCE: 53

Ile Ile Phe Arg Gly Val Arg Asp Arg Val Arg Gly Arg Ser Asp
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic peptide

<400> SEQUENCE: 54

Val Ile Phe Lys Arg Met Lys Asp Gln Ile Arg Glu Ser Glu Lys
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic peptide

<400> SEQUENCE: 55

Val Ile Phe Lys Arg Met Lys Asp Gln Ile Arg Glu Arg Glu Lys
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide

<400> SEQUENCE: 56

Val Ile Phe Lys Arg Met Lys Asp Lys Ile Arg Glu Arg Glu Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic peptide

<400> SEQUENCE: 57

Val Phe Phe Lys Arg Val Lys Asp Arg Ile Arg Glu Arg Ser Lys
1               5                   10                  15

<210> SEQ ID NO 58
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 58

Arg Arg Arg Arg Arg Arg Arg Arg Val Phe Phe Lys Gly Val Lys Asp
1               5                   10                  15

Arg Val Lys Gly Lys Ser Asp
            20
```

```
<210> SEQ ID NO 59
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 59

Arg Arg Arg Arg Arg Arg Arg Val Phe Phe Lys Gly Val Lys Asp
1               5                   10                  15

Arg Val

<210> SEQ ID NO 60
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 60

Arg Arg Arg Arg Arg Arg Val Phe Phe Lys Gly Val Lys Asp Arg Val
1               5                   10                  15

Lys Gly Lys Ser Asp
            20

<210> SEQ ID NO 61
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 61

Arg Arg Arg Arg Arg Val Phe Phe Lys Gly Val Lys Asp Arg Val
1               5                   10                  15

<210> SEQ ID NO 62
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 62

Arg Gln Pro Lys Ile Trp Phe Pro Asn Arg Arg Lys Pro Trp Lys Lys
1               5                   10                  15

Val Phe Phe Lys Gly Val Lys Asp Arg Val
            20                  25

<210> SEQ ID NO 63
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 63

Arg Gln Ile Lys Ile Trp Phe Gln Asn Arg Arg Met Lys Trp Lys Lys
1               5                   10                  15

Val Phe Phe Lys Gly Val Lys Asp Arg Val
            20                  25

<210> SEQ ID NO 64
```

```
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 64

Arg Lys Lys Arg Arg Gln Arg Arg Arg Val Phe Phe Lys Gly Val Lys
1               5                   10                  15

Asp Arg Val Lys Gly Lys Ser Asp
            20

<210> SEQ ID NO 65
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 65

Arg Lys Lys Arg Arg Gln Arg Arg Arg Val Phe Phe Lys Gly Val Lys
1               5                   10                  15

Asp Arg Val

<210> SEQ ID NO 66
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 66

Val Phe Phe Lys Gly Val Lys Asp Lys Val Lys Gly Lys Asp
1               5                   10
```

METHODS OF TREATING CANCERS WITH PEPTIDE-BASED MODULATORS

This application is a continuation of U.S. patent application Ser. No. 14/396,571, filed Oct. 23, 2014, which is a national phase application under 35 U.S.C. § 371 of International Application No. PCT/US2013/038207, filed Apr. 25, 2013, which claims the benefit of priority to U.S. Provisional Patent Application No. 61/638,094, filed Apr. 25, 2012. The entire contents of the above-referenced disclosures are specifically incorporated herein by reference.

This invention was made with government support under Grant No. RO-1 HL56728 and Grant No. R01 DE019355-05 awarded by the National Institutes of Health. The government has certain rights in the invention.

Pursuant to 37 C.F.R. 1.821(c), a sequence listing is submitted herewith as an ASCII compliant text file named "MESCP0061USC1_ST25.txt", created on Apr. 11, 2016 and having a size of ~16 kilobytes. The content of the aforementioned file is hereby incorporated by reference in its entirety.

BACKGROUND OF THE INVENTION

Field of the Invention

The present invention relates generally to the fields of molecular biology and medicine. More particularly, it concerns therapeutic peptides.

Description of Related Art

Age-related macular degeneration (AMD) is a progressive multifactorial disease involving genetic abnormalities and environmental insults. It is the leading cause of blindness for Americans over sixty. Dry AMD is characterized by drusen, retinal pigment epithelia (RPE) damage, and photoreceptor loss. In wet AMD, which develops from dry AMD, subsequent pathological events include breakdown of RPE/Bruch's membrane, increased release of the pro-angiogenic factor VEGF and development of choroidal neovascularization (CNV). Intact tight-junctions have been shown to be essential for efficient removal of fluid from the subretinal space and for barrier function of the RPE. Subretinal fluid accumulation has been reported in AMD, implying impaired barrier function. Barrier properties rely on tight junctions (TJ), which are protein complexes (including claudin, occludin, Jam) that link via the zonula occludens (ZO-1) protein to the actin cytoskeleton. ZO-1 is believed to form a scaffold at the face of the junction, and ZO-1 may function as a key cytoplasmic regulator of TJ stability.

Treatment options for AMD are currently limited. VEGF blocking therapies are often used to treat wet AMD; however, such therapies present various limitations. For example, VEGF treatment typically involves repeated intravitreal injections and is FDA-limited to 2-years, as side effects from repeat injections might outweigh treatment benefit.

Injuries and inflammation resulting from trauma, surgery, or disease continues to be a problem. Clearly, there is a need for new therapies to promote wound healing and/or decrease inflammation.

SUMMARY OF THE INVENTION

The present invention overcomes limitations in the prior art by providing therapeutic peptides. In some embodiments, the peptides may be used to provide an anti-fibrotic, anti-scarring, anti-inflammatory, and/or pro-regenerative effect on a wounded, diseased, or broken tissue. A peptide of the present invention may be included for example in a pharmaceutical preparation, a wound dressing, or a medical implant.

An aspect of the present invention relates to an isolated peptide, wherein the peptide is less than 50, preferably less than 45, preferably less than 40, preferably less than 35 amino acids (aa) in length and comprises JM1 (SEQ ID NO:1) or JM2 (SEQ ID NO:2), or a sequence having at least 90% sequence identity to JM1 (SEQ ID NO:1) or JM2 (SEQ ID NO:2). The peptide may be coupled a cell penetrating peptide or a cell internalization peptide. The cell penetrating peptide may be a polyarginine, penetratin, an Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-I, SynB1, Pep-7, HN-1, BGSC (Bis-Guanidinium-Spermidine-Cholesterol, or BGTC (BisGuanidinium-Tren-Cholesterol). In some embodiments, the cell penetrating peptide is a polyarginine. The polyarginine may comprise D-isomers of arginine. The polyarginine consists of five to nine arginine residues, wherein a plurality of the arginine residues in the polyarginine are D-isomers of arginine. In some embodiments, the polyarginine consists of RRRRRRRR (SEQ ID NO:3), wherein the arginine residues in the polyarginine are D-isomers of arginine. The peptide may consists of the sequence rrrrrrrrVFFKGVKDRVKGRSD (SEQ ID NO:4) or rrrrrrrrVFFKGVKDRV (SEQ ID NO:5). In some embodiments, the peptide does not comprise a cell penetrating peptide sequence or a cell internalization peptide. The peptide may consist of VFFKGVKDRVKGKSD (SEQ ID NO: 6) or VFFKGVKDRV (SEQ ID NO: 7). The peptide may comprise one or more D-amino acids or modified amino acids. The peptide may consist of L-amino acids. The peptide may be pegylated or chemically modified. The chemical modification may comprise peptide cyclization, acylation, phosphorylation, acetylation, or nitrosylation. The peptide may be produced recombinantly or synthetically. The peptide may be comprised in a kit.

In some embodiments, the peptide is comprised in a pharmaceutical preparation. The pharmaceutical preparation may be a topical composition, such as, e.g., an ointment, lotion, spray, cream, or gel. The gel may be a pluronic gel. The pharmaceutical preparation may comprise a poloxamer, a cross-linked collagen, or a collagen polymer. The pharmaceutical preparation may comprise from about 0.001-2% w/v or v/v to about 2-10% w/v or v/v of the peptide. The pharmaceutical preparation may comprise from about 0.1 µM to about 1000 µM of the peptide. The pharmaceutical preparation further comprises a second therapeutic agent such as, e.g., an antimicrobial agent, an anti-fungal agent, an anti-viral agent, or an anti-inflammatory agent. In some embodiments, the second therapeutic agent is an antimicrobial agent. The antimicrobial agent may be an antibiotic. The antimicrobial agent may comprise or consist of iodine, ethanol, isopropanol, or chlorhexidine.

Another aspect of the present invention relates to an isolated nucleic acid segment encoding a peptide of the present invention.

Yet another aspect of the present invention relates to a vector comprising a contiguous sequence consisting of the nucleic acid segment encoding a peptide of the present invention.

Another aspect of the present invention relates to a host cell comprising a nucleic acid segment encoding a peptide of the present invention.

Yet another aspect of the present invention relates to a wound-treating material coated with or comprising a peptide of the present invention. The material may be selected from the group consisting of a bandage, steri-strip, suture, staple, and graft. The material may be a silicone implant or may comprise silicone. The silicone implant may be a breast implant. In some embodiments, one or more peptides may be coated on or applied to the surface of a medical implant or prosthetic implant to decrease inflammation associated with implantation of the medical implant or prosthesis. For example, the medical implant may be a silicone breast implant, vascular stent, implanted pacemaker, or tissue engineered scaffold containing stem cells. The material may be a medical implant, a bio-engineered material, a tissue engineered scaffold, or the material may comprise a biodegradable scaffold or a biocompatible scaffold.

Another aspect of the present invention relates to a medical device coated with or comprising a peptide of the present invention. The medical device may comprise silicone. The medical device may be a breast implant, tissue expander, implantable cardioverter defibrillator, artificial hip, pacemaker, metal screw, pin, plate, and/or rod used in surgery, artificial knee, coronary stent, ear tube, or an artificial eye lens.

Yet another aspect of the present invention relates to a composition comprising a peptide of the present invention, a nucleic acid of the present invention, a vector of the present invention, or a wound-treating material of the present invention for use in promoting wound healing, decreasing scarring, decreasing inflammation, or promoting muscle formation.

Another aspect of the present invention relates to a composition comprising a peptide of the present invention, a nucleic acid the present invention, a vector of the present invention, or a wound-treating material the present invention for use as a medicament.

Yet another aspect of the present invention relates to a peptide of the present invention, a nucleic acid of the present invention, a vector of the present invention, or a wound-treating material of the present invention for use in the manufacture of a medicament for promoting wound healing, decreasing scarring, decreasing inflammation, or promoting muscle formation.

Another aspect of the present invention relates to a method of promoting wound healing, decreasing scarring, or decreasing inflammation in a subject, comprising administering to a subject a therapeutically effective dose of a peptide of the present invention to the subject. The subject may be a mammal, such as a human. The wound may be a slow healing wound, a diabetic foot ulcer, a pressure ulcer, a neural injury, a dental injury, a cardiac injury, an ischemic brain injury, a spinal cord injury, a periodontal injury, a tendon or ligament injury, a venous leg ulcer, an ischemic ulcer, a bed sore, or a corneal ulcer. The wound may result from a muscle atrophy disease, a neurodegenerative disease (e.g., Alzheimer's disease, Parkinson's disease, Hungton's disease, a motor neuron disease, dementia, an extrapyramidal or movement disorder), a heart disease, metabolic syndrome, an eye disease, or a disease of the skin or other organ systems of the body. The subject may have a wound or injury to or of the skin or cartilage. The peptide may be administered to the subject topically or parenterally. The peptide may be comprised in a pharmaceutical formulation. A pharmaceutically effective dose of the peptide may be administered to the subject that is sufficient to promote wound healing, to decrease inflammation, and/or to decrease scarring in the subject. The peptide may further comprise a detectable label.

Another aspect of the present invention relates to a method of treating an inflammatory eye disease in a subject, comprising administering to the subject a pharmacologically effective or a therapeutically effective dose of a peptide of the present invention to a subject. The inflammatory eye disease may be age related macular degeneration, a diabetic eye disease, a retinopathy, or a retinopathy of prematurity. The peptide may be comprised in a pharmaceutical preparation. The pharmaceutical preparation may be eye drops. The peptide may be encoded by a nucleic acid, wherein the nucleic acid is comprised in a vector. The method may further comprise administering, injecting, or introducing the peptide into the eye of the subject. For example, the peptide may be administered, injected, or introduced into the vitreous of the eye.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 4A-M. Healing of excisional wounds on adult mice over 10 days following wounding and peptide treatment. (FIGS. 4A-E) versus a vehicle control (FIGS. 4F-J). FIG. 4K is a quantitative demonstration that ACT1-treated wounds (n=102, blue bars) are significantly smaller in size at 24 hr, 4, 7 and 10 days as compared to controls (n=95, purple bars). Wound redness in the same wounds measured for closure is significantly decreased at 24 hr and 4 days post-wounding (FIG. 4L) and scarring/overall appearance is significantly improved at 7 and 10 days post-wounding (FIG. 4M) after ACT1 peptide treatment compared to controls. Scale for FIGS. 4A-J=1 mm.

(FIGS. 6A-E) Representative tracings from premature ventricular pacing protocol on isolated perfused hearts illustrate no arrhythmia (FIG. 6A), 3 spontaneous PVCs (FIG. 6B), resolving tachycardia (FIG. 6C), sustained tachycardia (FIG. 6D), and fibrillation (FIG. 6E). The numbers in FIGS. 6A-D label the s1, s2, and s3 stimuli. The blue arrows in FIG. 6A denote the stimulated ventricular action potential. (FIG. 6F) Numbers of hearts displaying arrhythmias (dark red and blue colors) that were unsustained (left-hand bar graph) or sustained (right-hand bar graph) in αCT1, Rev and Veh groups following pacing. Lighter red and blue colors within bars indicate number of hearts within groups in which arrhythmia was not induced by pacing. (FIG. 6G) Graphical representation of the median severity of arrhythmia for the three treatment groups ($p<0.02$ αCT1/Rev, $p<0.02$ αCT1/Veh). $N \geq 11$ (mice/group). p values for comparisons of frequency and severity of induced arrhythmia were generated from Chi square and Kruskal-Wallis tests and post-tests, respectively.

(FIGS. 12A-B) Muscle sensor implant interface 24 hrs post-operation treated with 50 µL of 180 µM JM2 peptide. (FIGS. 12C-D) muscle sensor implant interface 24 hrs post operation with no peptide treatment (controls). In controls (FIGS. 12C-D), high levels of inflammatory infiltrate are seen adjacent the "implant pocket" regions consistent with an acute inflammatory response. The line in FIG. 12C marks a tissue reaction area next to the implant. In FIG. 12D the arrows show dying/necrotic skeletal muscle fibers. In treatments FIGS. 12A-B, a narrower tissue reaction zone is seen (line in FIG. 12B), as well as significantly lower levels of inflammatory cells. There is little evidence of muscle necrosis (small arrows in FIG. 12B). Overall, these images demonstrate that treatment with JM peptide reduces inflammatory infiltrate, narrows tissue reaction zone, reduces necrosis of skeletal muscle and allows for a more intact border zone between reaction area and native tissue at 24 hrs post implantation. Images shown are from tissue sections are stained with H&E and imaged with a 10× objective.

FIG. 13A-D. JM peptide decreases scarring and preserves muscle associated with silicon implants. (FIGS. 13A-B) Muscle sensor implant interface 4.5 weeks post-operation treated with 50 µL of 180 µM JM2 peptide. (FIGS. 13C-D) Muscle sensor implant interface 4.5 weeks post operation with no peptide treatment (controls). In controls (FIGS. 13C-D), high levels of fibrotic scar tissue are seen adjacent the "implant pocket" consistent with a strong fibrotic/scarring response. There is profound loss of skeletal muscle fibers around the implant. In treatments (FIGS. 13A-B), a narrower, more compact scar is seen (arrows in FIG. 13A), as well as significantly higher levels of surrounding skeletal muscle. Overall, these images demonstrate that treatment with JM peptide reduces scarring and fibrosis and preserves and/or promotes the growth and/or regeneration of skeletal muscle cells 4.5 weeks after the implantation procedure. Images shown are from tissue sections stained with H&E (FIGS. 13A & C) and Masson's Trichrome (FIGS. 13B & D) and imaged with a 10× objective.

DESCRIPTION OF ILLUSTRATIVE EMBODIMENTS

The present invention overcomes limitations in the prior art by providing peptides that can inhibit collagen synthesis, processing, and/or secretion in scar forming cells or fibroblasts. In various aspects, the peptides may be used to promote anti-fibrotic, anti-scarring, anti-inflammatory and/or pro-regenerative effects on wounded, diseased, or broken tissues. In certain embodiments, the inventors have surprisingly discovered that various peptides of the present invention can exhibit an increased potency in inhibiting collagen processing and secretion, as compared to the previously identified peptides of alpha connexin such as ACT1.

JM Peptides

The present invention is based, in part, on the identification that certain peptides, e.g., the juxtamembrane peptides JM1 and JM2, can inhibit collagen synthesis, processing, and secretion from scar forming cells or fibroblasts. These compositions can be used in methods for: a) promoting tissue regeneration, b) promoting healing, c) curing disease, d) inhibiting metastasis, e) blocking scarring, and f) promoting normalized and/or improved physiological state and function.

Synthetic JM peptides disclosed in this invention include those of the amino acid sequence: rrrr rrrr VFFK-GVKDRVKGRSD—JM2 (SEQ ID NO: 8) and rrrr rrrr VFFKGVKDRV—JM1 (SEQ ID NO:9). The 8 lower case r's represent D isomers of the amino acid arginine and together form a cell penetration sequence. The subsequent 15 (JM2) or 10 (JM1) amino acids (aas) are based on the juxtamembrane sequence of the gap junction protein Cx43. JM1 is based on aas 231 to 241 of Cx43. JM2 is based on aas 231 to 246 of Cx43.

Figure 1:
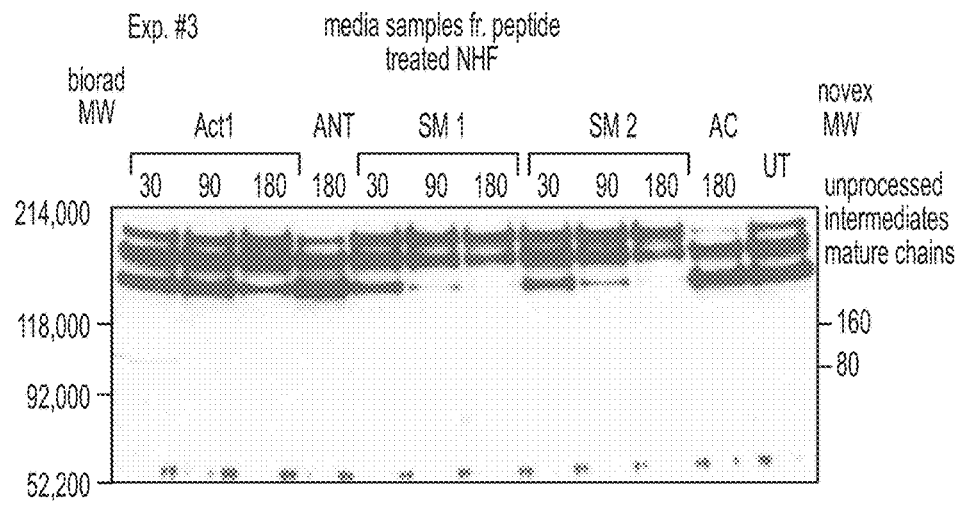
FIG. 1. Western blot analysis of collagen I α1 chain expression by cardiac fibroblasts. Conditioned media was collected from neonatal rat cardiac fibroblast cells cultures which had been treated with increasing concentrations of the ACT1 peptide (ACT1), an ACT1 sequence control peptide (ANT), increasing concentrations of the JM1 and JM2 peptides, vehicle control (HC 180) or left untreated (UT). The upper band in each lane represents the unprocessed α1 chain of rat type I collagen, the middle band processing intermediates and the lower band fully processed α1 collagen type I chains capable of incorporating into collagen fibrils. While treatment with the ACT1 peptide resulted in decreased levels of fully processed collagen I α1 chains relative to control or untreated samples, treatment with both JM1 and JM2 peptides at the maximum dose tested resulted in no detectable mature collagen I α1 chains.
Figure 2:
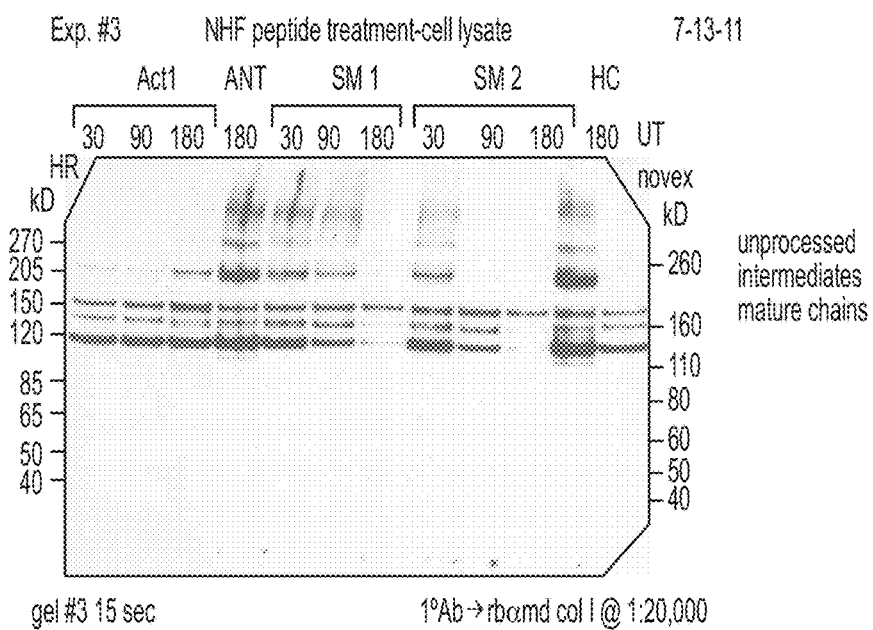
FIG. 2. Western blot analysis of collagen I α1 chain expression in fibroblast cell lysates. Cell lysates were prepared from neonatal rat cardiac fibroblast cells cultures which had been treated with increasing concentrations of the ACT1 peptide (ACT1), an ACT1 sequence control peptide (ANT), increasing concentrations of the JM1 and JM2 peptides, vehicle control (HC 180) or left untreated (UT). The largest bands in the image represent aggregates of multiple α1 chains. Bands corresponding to the unprocessed α1 chain of rat type I collagen, processing intermediates and the fully processed α1 collagen type I chains are indicated. While treatment with the ACT1 peptide resulted in slight decreases in processed collagen I α1 chains, treatment with both JM1 and JM2 peptides at the maximum dose tested resulted in barely detectable mature collagen I α1 chains and a significant loss of processed intermediates. The decreased production of mature collagen monomers correlates with an absence of higher molecular weight collagen species in response to ACT1 and for the highest doses of JM1 and JM2 tested. This would suggest that fibroblasts treated with those peptide concentrations would have difficulty producing and assembling collagen fibers and that the JM peptides may be used in wound healing and/or anti-fibrotic therapies aimed at controlling collagen deposition.
Figure 3:
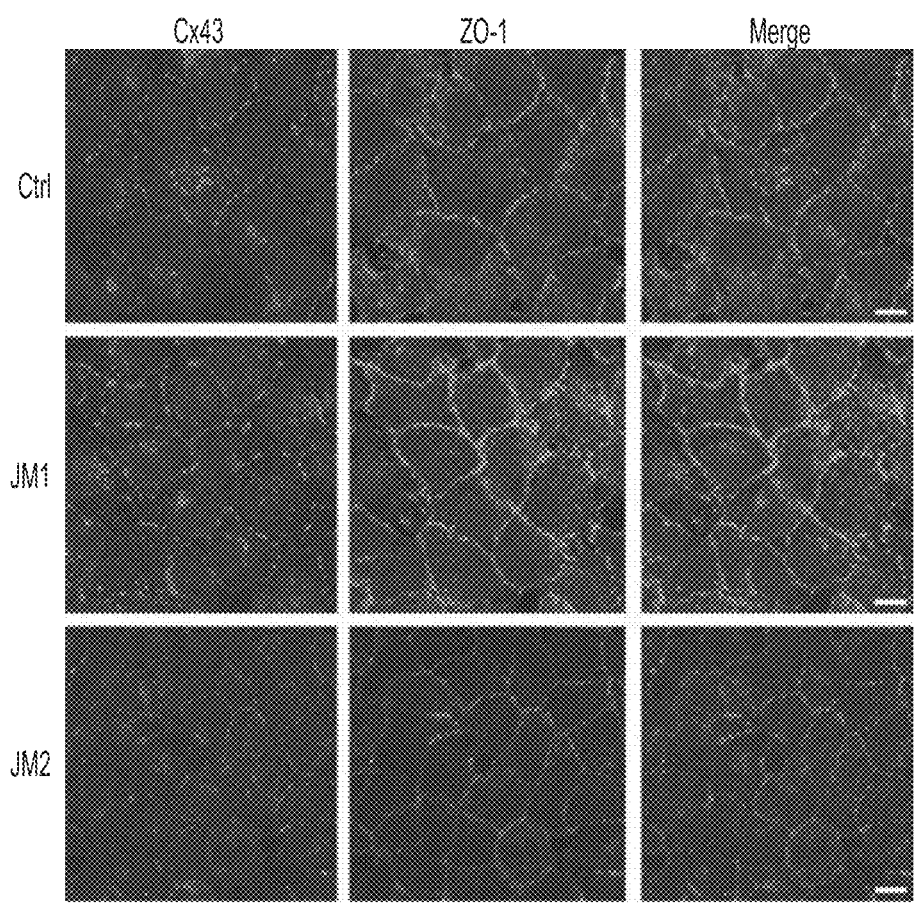
FIG. 3. JM1 and JM2 affect quantity and subcellular distribution of Cx43 and ZO-1. Cx43-HeLa cells were treated for 24 hours with either nothing (Ctrl), 10 μM JM1, or 10 μM JM2, fixed and stained for Cx43 or ZO-1. For both JM1 and JM2, greater cytoplasmic Cx43 was observed, particularly in perinuclear regions. However the most striking effects were on ZO-1 organization. In control cells ZO-1 localized to cell borders, often at sites of small, finger-like projections between the cells. Cytoplasmic ZO-1 was also notable. In JM-treated cells a strong contrast in the ratio of cell border to cytoplasmic ZO-1 was found, with relative levels at cell borders being increased over controls.

The potency of these peptides were gauged by comparison to ACT1, another Cx43 sequence that has been also shown to promote wound healing, regeneration and tissue repair (Gourdie et al., Compositions and methods for promoting wound healing and tissue regeneration, U.S. Pat. No. 7,786,074). ACT1 incorporates aas 373 to 382 of Cx43 and thus is distinct from JM1 and JM2. In the same assay on cultured fibroblasts, ACT1 also reduced collagen processing and secretion, but this reduction was less than that prompted by JM1 and JM2 (FIGS. 1 and 2). Examples of cell biological testing of JM peptides are shown in FIGS. 1-3.

In some embodiments, therapeutic polypeptides are provided that comprise a JM region of a connexin or related protein, wherein the polypeptide does not comprise the full-length of said protein. In some embodiments, the JM1 peptide comprises or consists of a JM peptide from a connexin.

Connexins are the sub-unit proteins that form gap junction channels, which are involved in intercellular communication (Goodenough and Paul, 2003). Hemichannel opening can mediate cell death and injury propagation. Release of molecules from hemichannels, such as ATP, can promote immune activation and guidance of immune cells, such as neutrophils, microglia and macrophages (Huang et al., 2012; Eltzschig et al., 2006). Without wishing to be bound by any theory, release of ATP by connexin hemichannels may promote fibrosis via activation of pro-fibrotic signaling pathways, such as via P2Y2 receptors (Lu et al., 2012). Connexin channels, as well as structurally related molecules, can act as single membrane channels or hemichannels. Connexin molecules can also act as regulatory molecules of signal transduction pathways inside cells and may have assignments outside of cells. For example, it has been shown that Cx43 can modulate the TGF-beta signaling pathway via a targeting of SMADs, downstream regulators of TGF-beta signaling (Dai et al., 2007). In another example, nephroblastoma overexpressed protein (NOV) interacts with the Cx43 carboxyl terminal (CT) domain (Fu et al., 2004).

The CT sequence of connexins is a regulatory domain. The CT amino acid sequences of connexins are generally characterized by distinct and conserved features. This preservation of structure is consistent with the ability to form characteristics 3D shapes, interact with multiple other proteins, interact with lipids and biomembranes, interact with nucleic acids including RNA, transit and/or block membrane channels and provide consensus sequences for proteolytic cleaving, cross-linking, nitrosylation, acetylation, ADP-ribosylation, glycosylation, phosphorylation, and other important regulatory domains. JM1 and JM2 peptides are based on sequences within the CT domain of Cx43 that mediates binding to proteins, lipids and other molecules. For example, the scaffolding protein ZO-1 interacts with the CT domain of Cx43 (Toyofuku et al., 1998). Without wishing to be bound by any theory, it is anticipated that this and other proteins may interact with other proteins or molecules forming mechanistic complexes involved in key aspects of biological function. In some embodiments, a polypeptide as disclosed herein may inhibit, activate, or otherwise modulate the operation of such molecular machinery, for example, having effects on processes including the regulation of aggregation of gap junction channels from hemichannels, connexin channel function, or regulating the trafficking of connexins to and from the plasma membrane of cells.

In some embodiments, peptides are provided which comprise a region of a connexin 43 (Cx43) that is proximal to or comprises at least part of a protein transmembrane domain that may be in close association with the lipid bilayer. In various embodiments, it is anticipated that the peptide comprises a region of a connexin from a non-human species that is homologous to amino acid positions 231-233 of human Cx43. Specific examples of JM peptides that may be used with the present invention are shown below in Table 1.

In some embodiments, the JM peptide may be an amino terminal (NT) sequence containing a short hydrophobic sequence. For example, for human Cx43 hydrophobic 3 hydrophobic amino acid (aa) residues VFF are positioned at amino acid positions 231-233. An identical and highly conserved JM VFF domain is seen in all Cx43 isoforms from various species from fish to humans. In another instance, the aforementioned hydrophobic 3 aas of all Cx43 isoforms are followed NT to CT by sequences with a high content of hydrophilic and polar aas, with particular enrichment for the aas K, R, and D. In another instance, polar and positively charged amino acids (marked in bold in the following JM2 sequence) display a distinctive alternating sequence as seen in JM2 (VFFKGVKDRVKGRSD, SEQ ID NO:10). In another example, an alternating sequence of positively charged amino acids interspersed with hydrophobic and negatively charged amino acids—as illustrated in bold in this depiction of JM2 (VFFKGVKDRVKGRSD, SEQ ID NO:10) is seen. The polypeptide used with the disclosed invention may, in some embodiments, comprise up to 30 amino acids of the JM region including 3, 4, 5, 6, 7, 8, 9, 10, 11, 12, 13, 14, 15, 16, 17, 18, 19, 20, 21, 22, 23, 24, 25, 26, 27, 28, 29, or 30 contiguous amino acids of a JM region. The JM region may be comprised in connexin 30.2, connexin 31.9, connexin 38, connexin 39, connexin 39.9, connexin 40, connexin 40.1, connexin 43.4, connexin 44, connexin 44.2, connexin 44.1, connexin 45, connexin 46, connexin 46.6, connexin 47, connexin 49, connexin 50, connexin 56, or connexin 59. It is anticipated that connexins more strongly related to Cx43 may exhibit a similar effect. Different isoforms of Cx43 found in different species may be used such as, e.g., dog Cx43, human Cx43, frog Cx43, and Fish Cx43, all have JM regions. Zebrafish Cx40.8, a non Cx43 isoform that also has a JM region, may be used in some embodiments.

A peptide of the present invention, such as a JM peptide, may be flanked at the N-terminus or the C-terminus by additional amino acids, such as amino acids from a connexin that are outside the range of the juxtamembrane region. For example, proximal amino acids that may be coupled or attached (e.g., via a linker or peptide bond) to the N-terminus of a JM sequence include 1, 2, 3, 4, 5, 6, 7, 8, 9 or more or all of amino acids 209 to 230 of human Cx43. Amino acids that may be coupled or attached to the C-terminus of a JM sequence include, e.g., 1, 2, 3, 4, 5, 6, 7, 8, 9 or more or all of amino acids 262 to 382 of human Cx43. In some embodiments, the peptide may further comprise a linker or a cell internalization sequence.

A JM peptide can retain function, in various embodiments, when flanked with polypeptides of up to at least 239 amino acids. Indeed, as long as the peptide is able to exhibit a therapeutic effect or access its cellular targets, it may be used with or attached to a JM peptide. Polypeptides exceeding 239 amino acids in addition to the CT-most peptide may be used in some embodiments.

The JM regions of connexins are highly conserved from humans to fish (e.g., as shown between connexin sequences for humans and zebrafish in Table 1). It is anticipated that proteins having significant homology (e.g., at least 80, 85, 90, 95 or more percent sequence identity) with a JM region, such as JM1, JM2, and/or JM3 (VFFKGVKDRVKGRSD-PYHAT, SEQ ID NO: 11) may be used in various aspects of the present invention.

TABLE 1

Examples of Connexin JM
Amino Acid Sequences

| | |
|---|---|
| Human Cx43 | VFF KGV KDRV KGKSD (SEQ ID NO: 12) |

TABLE 1-continued

Examples of Connexin JM Amino Acid Sequences

| | |
|---|---|
| Mouse Cx43 | VFF KGV KDRV KGRSD (SEQ ID NO: 13) |
| Dog Cx43 | VFF KGV KDRV KGQSD (SEQ ID NO: 14) |
| Chick alpha1 | VFF KGV KDRV KGKTD (SEQ ID NO: 15) |
| Zebrafish Cx43 | VLF KRI KDRV KSRQN (SEQ ID NO: 16) |
| Zebrafish Cx40.8 | VIF KRM KDQI RESEK (SEQ ID NO: 17) |

It is anticipated that homologous peptides from virtually any connexin may be used with the present invention. For example, a JM peptide that may be used with the present invention may comprise a peptide (e.g., an amino acid sequence homologous to JM1 or JM2) or a fragment of a connexin from a human, murine, bovine, monotrene, marsupial, primate, rodent, cetacean, mammalian, avian, reptilian, amphibian, piscine, chordate, or protochordate or other connexin or conservative variant thereof. Fragments of a connexins with conserved JM and/or proximal non-JM amino acids may be used in various embodiments of the present invention.

Other JM2 variants include:

```
canis lupus familiaris
                      (SEQ ID NO: 18)
VFFKGVKDRVKGQSD cricetulus griseus
                      (SEQ ID NO: 19)
VFFKGIKDRVKGRND ornithorhynchuys anatinus
                      (SEQ ID NO: 20)
VFFKGVKDRVKGRID erinaceus europaeus
                      (SEQ ID NO: 21)
VFFKGIKDRVKGKSD sus scrofa
                      (SEQ ID NO: 22)
FFKGVKDRVKGKSD cynops pyrrhogaster
                      (SEQ ID NO: 23)
FKSVKDRIKGRSD oryctolagus cuniculus
                      (SEQ ID NO: 24)
VFFRSVKDHVKGKSD oreochromis niloticus
                      (SEQ ID NO: 25)
VFFKRIKDRVKG carassius auratus
                      (SEQ ID NO: 26)
VLFKQIKDRVKGR cyprinus carpio
                      (SEQ ID NO: 27)
VLFKRIKDRVKGR
```

Peptides, peptide mimetics or conservative variants can be made to modulate gap junction, hemichannel or other independent biological functions that are based on the amino-terminal, extracellular, cytoplasmic loop and/or transmembrane domains of a connexin. Connexin family members may be used to develop peptide gap junction, hemichannel, or connexin based signal transduction modulating agents. Such peptides can comprise from 3-30, from 6-15, or 6, 7, 8, 9, 10, 11, 12, 13, 14, or 15 contiguous amino acids of a connexin. In some embodiments, one or more of the following sequences may be used as a Cx43 mimetic peptidergic inhibitor of a Cx43-based gap junction communication: FEVAFLLIQWI (SEQ ID NO: 28), LLIQWYIGFSL (SEQ.ID.NO: 29), SLSAVYTCKRDPCPHQ E2 (SEQ ID NO: 30) VDCFLSRPTEKT (SEQ.ID.NO: 31), SRPTEKTIFII (SEQ.ID.NO: 32), LGTAVESAWGDEQ (SEQ.ID.NO: 33), QSAFRCNTQQPG (SEQ.ID.NO: 34), QQPGCENVCYDK E1 (SEQ.ID.NO: 35), and VCYDKSFPISHVR E1 (SEQ.ID.NO: 36). The sequence may comprise of consist of a sequence found in the extracellular loop domain of connexins.

It is anticipated that a related sequence, e.g., a sequence homologous to JM1 or JM2, from connexins, innexins, or pannexins may be used in various embodiments of the present invention to promote wound healing or reduce inflammation. Related sequences incorporating the extracellular loop domains that modulate gap junction, hemichannel, or other independent biological functions can be found in other connexin family members connexins including Cx45, Cx40, Cx32, Cx26, Cx31 and other known connexins, innexins, and pannexins by those skilled in the art.

In various embodiments, a sequence having homology to a JM peptide (e.g., JM1, JM2, or JM3) may be used with the present invention to promote wound healing or decrease inflammation. JM-like regions can be found in proteins other than in connexins in a manner that is conserved from humans to viruses (e.g., as shown in Table 2). These sequences display the characteristic conserved 3 hydrophobic amino acid N-terminal amino acids rich in V, I and F, followed by the distinctive repeating sequence of polar and positively charged amino acids K and R. In some embodiments, one or more of the following sequences may be used with the present invention.

TABLE 2

Examples of Amino Acid Sequences with Similarity to JM2 from human Cx43

| Species | Protein | JM or JM-like sequence |
|---|---|---|
| human | Connexin43 | VFFKGVKDRVKGKSD (SEQ ID NO: 6) |
| Oreochromis niloticus (fish) | gap junction alpha-1 protein-like | VFFKRI K DRVKGK (SEQ ID NO: 37) |
| T. equigenitalis (bacterium) | Type I restriction-modification system, restriction subunit R | VFFK GIF Q KD R (SEQ ID NO: 38) |
| Dictyostelium discoideum (bacterium) | hypothetical protein DDB_G0282759 | IFFRVK D RVK (SEQ ID NO: 39) |
| Bacteroides sp. (bacterium) | transglutaminase-related protein | VFFDELKDRVKG (SEQ ID NO: 40) |

TABLE 2-continued

Examples of Amino Acid Sequences with Similarity to JM2 from human Cx43

| Species | Protein | JM or JM-like sequence |
|---|---|---|
| Bacillus cereus (bacterium) | stage V sporulation protein B | IFFKSVKRIKGK (SEQ ID NO: 41) |
| Fusobacterium nucleatum (virus/phage) | Phage protein | GFFKGVKDKVK (SEQ ID NO: 42) |

Phosphorylation is a common post-translational modification of proteins and is crucial for modulating or modifying protein structure and function. Aspects of protein structure and function modified by phosphorylation include protein conformation, protein-protein interactions, protein-lipid interactions, protein-nucleic acid interactions, channel gating, protein trafficking and protein turnover. Thus, in some aspects, phospho-Tyrosine (Y), phospho-Serine (S) and/or phospho-Threonine (T) rich sequences may be necessary for modifying the function of the molecules, increasing or decreasing efficacy of the polypeptides in their actions. The therapeutic polypeptide may comprise phosphorylated S, T and/or Y sequences. Exemplary phosphorylating agents are well known in the art and can include, TPA, Src or G protein-coupled receptor antagonists and agonists. Phosphorylation and dephosphorylation may be used to inhibit, enhance, or modify the activity of peptides of the present invention.

Peptides of the present invention may be acetylated. Acetylation is a common post-translational modification of proteins and is crucial for modulating or modifying protein structure and function. Aspects of protein structure and function modified by acetylation include protein conformation, protein-protein interactions, protein-lipid interactions, protein-nucleic acid interactions, channel gating, protein trafficking, and protein turnover. In some embodiments, the lysine (K) rich sequences may be necessary for modifying the function of the molecules, increasing or decreasing efficacy of the polypeptides in their actions. The therapeutic polypeptide may comprise K rich sequences or motifs. Exemplary acetylation and deacetylation agents are well known in the art and can include, HDAC activators and trichostatin-A. Acetylation can be used to inhibit, enhance, or otherwise modify the activity of a therapeutic polypeptide or JM peptide.

It is anticipated that one or more amino acid substitution, insertion, or deletion may be made to a peptide of the present invention (e.g., a JM peptide) without substantially reducing or eliminating the ability of the peptide to impart a therapeutic effect, such as promoting wound healing or reducing inflammation, in a subject. Protein variants and derivatives are contemplated for use with the present invention and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions typically involve smaller insertions than those of amino or carboxyl terminal fusions, for example, an insertion of one to four amino acid residues. Deletions are characterized by the removal of one or more amino acid residues from the protein sequence. Variants may be prepared by site-specific mutagenesis of nucleotides in the DNA encoding the protein, thereby producing DNA encoding the variant, and thereafter expressing the DNA in recombinant cell culture. Alternately, variants may be produced by peptide synthesis. Techniques for making substitution mutations at predetermined sites in DNA having a known sequence are well known and include, for example, M13 primer mutagenesis and PCR mutagenesis. Amino acid substitutions typically involve mutation of single residues, but may occur at a number of different locations at once, e.g., on 1, 2, 3, 4, or 5 amino acid residues. Deletions or insertions may be made in adjacent pairs, i.e., a deletion of 2 residues or an insertion of 2 residues. Substitutions, deletions, insertions or any combination thereof can be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place. Such substitutions generally are made in accordance with the following Table 3 and are referred to as conservative substitutions.

TABLE 3

Amino Acid Substitutions

| Original Residue | Exemplary Substitutions |
|---|---|
| Ala | Ser |
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Pro | Gly |
| Ser | Thr |
| Thr | Ser |
| Trp | Tyr |
| Tyr | Trp; Phe |
| Val | Ile; Leu |

For example, the replacement of one amino acid residue with another that is biologically and/or chemically similar is known to those skilled in the art as a conservative substitution. A conservative substitution may involve, e.g., replacing one hydrophobic residue for another hydrophobic residue, or one polar residue for another polar residue. Substitutions include combinations shown in Table 3. Conservatively substituted variations of each explicitly disclosed sequence are included within the polypeptides provided herein.

Conservative substitutions may have little to no impact on the biological activity of a resulting polypeptide. In some embodiments, a conservative substitution in a peptide does not substantially affect the biological function of the peptide. A peptide can include one or more amino acid substitutions, for example 2-10 conservative substitutions, 2-5 conservative substitutions, 4-9 conservative substitutions, or 1, 2, 3, 4, 5 or 10 conservative substitutions.

Conservative substitutions can be introduced into a peptide sequence by known methods such as, e.g., site-directed mutagenesis or PCR. Alternatively, a polypeptide can be produced to contain one or more conservative substitutions by using standard peptide synthesis methods. An alanine scan may be used to identify which amino acid residues in a protein can tolerate an amino acid substitution. In one example, the biological activity of the protein is not decreased by more than 25%, for example not more than 20%, for example not more than 10%, when an alanine, or other conservative amino acid (e.g., as shown in Table 3), is substituted for one or more native amino acids. Further information about conservative substitutions can be found, e.g., in Ben-Bassat et al. (1987); O'Regan et al. (1989); Sahin-Toth et al. (1994); Hochuli et al. (1988) and in standard textbooks of genetics and molecular biology.

Substitutional or deletional mutagenesis may be employed to insert sites for N-glycosylation (Asn-X-Thr/Ser) or O-glycosylation (Ser or Thr). Deletions of cysteine or other labile residues may be performed. Deletions or substitutions of potential proteolysis sites, e.g., Arg, may be accomplished for example by deleting one of the basic residues or substituting one by glutaminyl or histidyl residues.

Certain post-translational derivatizations may result from expression of a peptide of the present invention in recombinant host cells. Glutaminyl and asparaginyl residues are frequently post-translationally deamidated to the corresponding glutamyl and asparyl residues. Alternatively, these residues may be deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (Creighton, 1983), acetylation of the N-terminal amine and, in some instances, amidation of the carboxyl-terminal.

It also is understood in the art that the substitution of like amino acids can be made effectively on the basis of hydrophilicity, particularly where the biological functional equivalent protein and/or peptide thereby created is intended for use in therapeutic or immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

It is understood that there are numerous amino acid and peptide analogs, which can be incorporated into the disclosed compositions. For example, there are numerous D amino acids or amino acids which have different substituents than the amino acids shown in Table 3. The opposite stereoisomers of naturally occurring peptides and/or the stereoisomers of peptide analogs may be used in peptides of the present invention.

For example, a peptide of the present invention (e.g., a JM peptide, JM1 peptide, or JM2 peptide) may comprise D isomers of arginine (R). These amino acids can readily be incorporated into polypeptide chains by charging tRNA molecules with the amino acid of choice and engineering genetic constructs that utilize, for example, amber codons, to insert the analog amino acid into a peptide chain in a site specific way (e.g., Thorson et al., 1991; Zoller, 1992; Ibba, 1995; Cahill et al., 1989; Benner, 1994; Ibba and Hennecke, 1994, all of which are herein incorporated by reference).

Molecules can be produced that resemble polypeptides, but which are not connected via a natural peptide linkage. For example, linkages for amino acids or amino acid analogs can include —CH2NH—, —CH2S—, —CH2-CH2-, —CH=CH— (cis and trans), —COCH2-, —CH(OH)CH2-, and —CHH2SO— (see, e.g., Spatola, 1983a; Spatola, 1983b; Morley, 1980; Hudson et al., 1979 (—CH2NH—, CH2CH2-); Spatola et al., 1986 (—CHH2-S); Hann, 1982 (—CH—CH—, cis and trans); Almquist et al., 1980 (—COCH2-); Jennings-White et al., 1982 (—COCH2-); European Appln, EP 45665 CA (—CH(OH)CH2-); Holladay et al., 1983 (—C(OH)CH2-); and Hruby, 1982 (—CH2-S—); each of which is incorporated herein by reference). It is understood that peptide analogs can have more than one atom between the bond atoms, such as b-alanine, g-aminobutyric acid, and the like.

Amino acid analogs and analogs and peptide analogs may have enhanced or desirable properties, such as more economical production, greater chemical stability, enhanced pharmacological properties (e.g., half-life, absorption, potency, efficacy, etc.), altered specificity (e.g., a broad-spectrum of biological activities), reduced antigenicity, and others.

D-amino acids may be included in a peptide of the present invention and can be used to improve the stability or half-life of peptides because D-amino acids are not recognized by peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch, 1992, incorporated herein by reference). Cyclized conservative variants of a peptide of the present invention, such as a JM peptide, are thus contemplated and may be used. In one example, a JM peptide incorporates D-amino acids in the poly-R cell internalization sequences (CIS) and this can confer the benefits of D-amino acids described herein.

In some embodiments, a peptide of the present invention may comprise a conservative variant. As shown in Table 3, an example of a single conservative substitution within the sequence for JM2 VFFKGVKDRVKGKSD (SEQ ID NO: 6) is given in the sequence VFFKGVKDKVKGKD (SEQ ID NO:66). An example of three conservative substitutions within the sequence JM2 VFFKGVKDRVKGKSD (SEQ ID NO: 6) is given in the sequence VFFKGVRDKVKGKTD (SEQ ID NO: 43). Thus, the provided polypeptide can comprise an amino acid sequence shown in Table 4.

TABLE 4

Polypeptide Variants of JM sequences

VFF KGV KDRV KGKSD (SEQ ID NO: 44)

VFF KGV KDRV (SEQ ID NO: 45)

IFF KGV KDRV KGKSD (SEQ ID NO: 46)

IFF KGV KDRV (SEQ ID NO: 47)

VIF KRM KDQI RESEK (SEQ ID NO: 48)

VFF KGV KDRV KGKTD (SEQ ID NO: 49)

VFF KGV KDRV KGRSD (SEQ ID NO: 50)

VFF KGV KDRV RGKSD (SEQ ID NO: 51)

VFF KGV KDKV KGKSD (SEQ ID NO: 52)

IIF RGV RDRV RGRSD (SEQ ID NO: 53)

VIF KRM KDQI RESEK (SEQ ID NO: 54)

VIF KRM KDQI REREK (SEQ ID NO: 55)

VIF KRM KDKI REREK (SEQ ID NO: 56)

VFF KRV KDRI RERSK (SEQ ID NO: 57)

It is understood that one way to define any variants, modifications, or derivatives of the disclosed genes and proteins herein is through defining the variants, modification, and derivatives in terms of sequence identity (also referred to herein as homology) to specific known sequences. Specifically disclosed are variants of the nucleic acids and polypeptides herein disclosed which have at least 80, 81, 82, 83, 84, 85, 86, 87, 88, 89, 90, 91, 92, 93, 94, 95, 96, 97, 98, 99 percent sequence identity to the stated or known sequence. Those of skill in the art readily understand how to determine the sequence identity of two proteins or nucleic acids. For example, the sequence identity can be calculated after aligning the two sequences so that the sequence identity is at its highest level.

Another way of calculating sequence identity can be performed by published algorithms. Optimal alignment of sequences for comparison can be conducted by the local sequence identity algorithm of Smith and Waterman (1981), by the sequence identity alignment algorithm of Needleman and Wunsch (1970), by the search for similarity method of Pearson and Lipman (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference in their entirety for the methods of calculating sequence identity. Sequence identity can be obtained for nucleic acids by, for example, the algorithms disclosed in Zuker (1989); Jaeger et al. (1989a); Jaeger et al. (1989b), which are herein incorporated by reference.

As used herein, the term "peptide" encompasses amino acid chains comprising less than 100 amino acids and preferably less than 50 amino acid residues, wherein the amino acid residues are linked by covalent peptide bonds. The peptide may comprise one or more modified or unusual amino acids as shown below in Table 5.

A peptide of the present invention may comprise a sequence having at least about, or comprise a sequence with at least about, 90%, 95%, or 100% sequence identity with any of SEQ ID NOs: 1 or 2 (also referred to as "JM1 peptide" and "JM2 peptide," respectively) disclosed herein. The peptide may be from 8 to 45, 10 to 40, 10 to 30, 10 to 25, 10 to 20, 10 to 15, 9, 10, 11, 12, 13, 14, 15, 16, 17, 18, 19, 20, 21, 22, 23, 24, 25, 26, 27, 28, 29, or 30 amino acids in length, or any length or range derivable therein. The peptide may be a recombinant peptide, synthetic peptide, purified peptide, immobilized peptide, detectably labeled peptide, encapsulated peptide, or a vector-expressed peptide.

TABLE 5

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Connexins may be affected by G-protein-coupled receptor (GPCR) activation. For example, cell-cell coupling mediated by Cx43 is reduced after GPCR activation (Tence et al., 2012). Agonists for this GPCR or G(i/o) response include endothelin (ET), thrombin, nucleotides (e.g., ATP), lysophosphatidic acid (LPA), noradrenalin, anandamide and bioactive lipids, such as S1P (Giaume paper), many of which are potent inflammatory mediators. This response appears to occur directly via effects on phosphatidylinositol 4,5-bisphosphate (Ptd Ins (4,5) P-2) P I P-2. Levels of P I P-2 in the plasma membrane dictate the response of Cx43 gap junctional communication to GPCR stimulation. Dephosphorylation of Cx43 that accompanies activation by GPCR agonists such as by ET occur via a phosphatase action of calcineurin. In addition to its key role in vascular tone, ET signaling has key assignments in initiation and in maintenance of fibrosis health and disease. ET signaling may also be the ultimate basis of pro-fibrotic effects of the other agents, including pro-fibrotic and pro-inflammatory cytokines. For example, the effect of angiotensin II on collagen I expression is mediated by the profibrogenic action of endothelin (Boffa et al., 1999). ET has been shown to have potent effects on collagen gene expression and procollagen processing in fibroblasts (Dawes et al., 1996).

Without wishing to be bound by any theory, it is envisioned that a mode of action of JM peptides is via effects on the opening and closing of connexin hemichannels and gap junction channels. A mode of action of JM peptides might involve effects on expression, translation, post-translational modification, intracellular retention, membrane targeting, trafficking, aggregation, turnover, and/or breakdown of connexins, connexin and pannexin hemichannels and gap junction channels. Without wishing to be bound by any theory, it is contemplated that JM peptides may exert a therapeutic effect via modulation of GPCR signaling.

Therapeutic peptides of the present invention may be used to treat a variety of diseases. More specifically, GPCR-mediated modulation of Cx43 function may have broad physiological and pathophysiological consequences for signaling in Cx43 expressing cells, tissues and disease processes including in systemic sclerosis, scleroderma, congestive heart failure, pulmonary hypertension, pulmonary fibrosis, posterior capsule opacification, fibrotic disease of the eye lens and/or trabecular meshwork, glaucoma, mast cell activation, atherosclerosis, diabetic cardiomyopathy, hepatic fibrosis, kidney disease, fibrosis of liver, pancreas and intestine, cancer, including pancreatic cancer, cerebral vasospasm following subarachnoid hemorrhage, arterial hypertension, pain mediation, and/or cardiac hypertrophy. Targeting of GPCR signaling can inhibit, prevent, ameliorate, or substantially correct dysfunctions or diseases including, but not limited to, infections such as bacterial, fungal, protozoan, and viral infections, peripheral (PNS) and central nervous system (CNS) disorders including acute and chronic pain, posterior capsule opacification, fibrotic disease of the eye lens and trabecular meshwork, glaucoma, cardiovascular diseases including acute heart failure, hypotension, hypertension, angina pectoris, myocardial infarction (MI), hematological diseases, cancers, allergies including asthma, genito-urinary diseases including benign prostate hyperplasia and urinary incontinence and, osteoporosis, Alzheimer's disease, Parkinson's disease, respiratory diseases, gastro-enterological diseases, metabolic diseases, inflammatory diseases, endocrine diseases, diseases of the skin, reproductive, immune muscululosketal system or congenital and developmental diseases. In some embodiments, a pharmaceutically acceptable carrier may comprise a combination of one, two or more of any of the herein provided JM polypeptides for the treatment of one or more of these diseases.

Methods of Polypeptide Synthesis

In certain embodiments of the present invention, the polypeptide is encoded by a single recombinant nucleic acid sequence using recombinant techniques. In other embodiments, the vascular endothelial targeting amino acid sequence and the cytotoxic amino acid sequence have been encoded by separate nucleic acid sequences, and subsequently joined by chemical conjugation. In further embodiments, the polypeptide has been synthesized de novo.

Recombinant Techniques

In certain embodiments of the present invention, a peptide of the present invention is encoded by a single recombinant polynucleotide using recombinant techniques well-known to those of ordinary skill in the art. The polynucleotide may include a sequence of additional nucleic acids that direct the expression of the chimeric polypeptide in appropriate host cells.

Due to the inherent degeneracy of the genetic code, other DNA sequences that encode substantially the same or a functionally equivalent amino acid sequence, may be used in the practice of the invention of the cloning and expression of the chimeric protein. Such DNA sequences include those capable of hybridizing to the peptide sequences or their complementary sequences under stringent conditions. In one embodiment, the phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with a 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

Altered DNA sequences that may be used in accordance with the invention include deletions, additions or substitutions of different nucleotide residues resulting in a sequence that encodes the same or a functionally equivalent polynucloetide. The polynucleotide may contain deletions, additions or substitutions of amino acid residues within a chimeric sequence, which result in a silent change thus producing a functionally equivalent chimeric polynucleotide. Such amino acid substitutions may be made on the basis of similarity in polarity, charge, solubility, hydrophobicity, hydrophilicity, and/or the amphipathic nature of the residues involved, as discussed above.

The DNA sequences of the invention may be engineered in order to alter a chimeric coding sequence for a variety of ends, including but not limited to, alterations that modify processing and expression of the gene product. For example, mutations may be introduced using techniques that are well known in the art, e.g., site-directed mutagenesis, to insert new restriction sites, to alter glycosylation patterns, phosphorylation, etc.

In order to express a biologically active chimeric polypeptide, the nucleotide sequence coding for a chimeric polypeptide, or a functional equivalent, is inserted into an appropriate expression vector, i.e., a vector that contains the necessary elements for the transcription and translation of the inserted coding sequence. The chimeric gene products as well as host cells or cell lines transfected or transformed with recombinant chimeric expression vectors can be used for a variety of purposes. These include, but are not limited to, generating antibodies (i.e., monoclonal or polyclonal) that bind to epitopes of the proteins to facilitate their purification.

Methods that are well known to those skilled in the art can be used to construct expression vectors containing the chimeric coding sequence and appropriate transcriptional/translational control signals. These methods include in vitro recombinant DNA techniques, synthetic techniques and in vivo recombination/genetic recombination. See, for example, the techniques described in Sambrook et al., 2001.

A variety of host-expression vector systems may be utilized to express the chimeric polypeptide coding sequence. These include but are not limited to microorganisms such as bacteria transformed with recombinant bacteriophage DNA, plasmid DNA or cosmid DNA expression vectors containing the chimeric protein coding sequence; yeast transformed with recombinant yeast expression vectors containing the chimeric protein coding sequence; insect cell systems infected with recombinant virus expression vectors (e.g., baculovirus) containing the chimeric protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the chimeric protein coding sequence; or animal cell systems. It should be noted that since most apoptosis-inducing proteins cause programmed cell death in mammalian cells, it is preferred that the chimeric protein of the invention be expressed in prokaryotic or lower eukaryotic cells.

The expression elements of each system vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the chimeric DNA, SV40-, BPV- and EBV-based vectors may be used with an appropriate selectable marker.

In bacterial systems a number of expression vectors may be advantageously selected depending upon the use intended for the peptide expressed. For example, when large quantities of peptide are to be produced, vectors that direct the expression of high levels of protein products that are readily purified may be desirable. Such vectors include but are not limited to the E. coli expression vector pUR278 (Ruther et al., 1983), in which the chimeric protein coding sequence may be ligated into the vector in frame with the lacZ coding region so that a hybrid AS-lacZ protein is produced; pIN vectors (Van Heeke and Schuster, 1989); and the like.

An alternative expression system that could be used to express chimeric polypeptide is an insect system. In one such system, Autographa californica nuclear polyhidrosis virus (AcNPV) is used as a vector to express foreign genes. The virus grows in Spodoptera frugiperda cells. The chimeric protein coding sequence may be cloned into non-essential regions (for example the polyhedrin gene) of the virus and placed under control of an AcNPV promoter (for example the polyhedrin promoter). Successful insertion of the chimeric polypeptide coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith et al., 1983; U.S. Pat. No. 4,215,051).

Specific initiation signals may also be required for efficient translation of the inserted chimeric protein coding sequence. These signals include the ATG initiation codon and adjacent sequences. In cases where the entire chimeric gene, including its own initiation codon and adjacent sequences, is inserted into the appropriate expression vector, no additional translational control signals may be needed. However, in cases where the chimeric protein coding sequence does not include its own initiation codon, exogenous translational control signals, including the ATG initiation codon, must be provided. Furthermore, the initiation codon must be in phase with the reading frame of the chimeric protein coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of consensus N-glycosylation sites in a chimeric protein may require proper modification for optimal chimeric protein function. Different host cells have characteristic and specific mechanisms for the post-translational processing and modification of proteins. Appropriate cell lines or host systems can be chosen to ensure the correct modification and processing of the chimeric protein. To this end, eukaryotic host cells which possess the cellular machinery for proper processing of the primary transcript, glycosylation, and phosphorylation of the chimeric protein may be used. Such mammalian host cells include but are not limited to CHO, VERO, BHK, HeLa, COS, MDCK, 293, W138, and the like.

For long-term, high-yield production of recombinant chimeric polypeptides, stable expression is preferred. For example, cell lines that stably express the chimeric polypeptide may be engineered. Rather than using expression vectors that contain viral originals of replication, host cells can be transformed with a chimeric coding sequence controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler et al., 1977), hypoxanthine-guanine phosphoribosyltransferase (Szybalski and Szybalski, 1962), and adenine phosphoribosyltransferase (Lowy et al., 1980) genes can be employed in tk-, hgprt- or aprt-cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan and Berg, 1981); neo, which confers resistance to the aminoglycoside G-418 (Colbere-Garapin et al., 1981); and hygro, which confers resistance to hygromycin (Santerre et al., 1984) genes. Additional selectable genes have been described, namely trpB, which allows cells to utilize indole in place of tryptophan; hisD, which allows cells to utilize histinol in place of histidine (Hartman and Mulligan, 1988); and ODC (ornithine decarboxylase) which confers resistance to the ornithine decarboxylase inhibitor, 2-(difluoromethyl)-DL-ornithine, DFMO (see McConlogue, 1986).

De Novo Synthesis

In an alternate embodiment of the invention, a peptide of the present invention could be synthesized de novo in whole or in part, using chemical methods well known in the art (see, for example, Caruthers et al., 1980; Crea and Horn, 1980; and Chow and Kempe, 1981). For example, the component amino acid sequences can be synthesized by solid phase techniques, cleaved from the resin, and purified by preparative high performance liquid chromatography followed by chemical linkage to form a chimeric protein. (e.g., see Creighton, 1983). The composition of the synthetic peptides may be confirmed by amino acid analysis or sequencing (e.g., the Edman degradation procedure; see Creighton, 1983).

Polypeptide synthesis techniques are well known to those of skill in the art (see, e.g., Bodanszky et al., 1976). These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. Such protecting group moieties may be used in the course of synthesis, but they are removed before the peptides are used. Additional reactions may be necessary, as described elsewhere, to form intramolecular linkages to restrain conformation.

Cell Penetrating Peptides

A peptide of the present invention may comprise or be coupled to (e.g., via a peptide bond, linker, or cleavable linker) a cell penetrating peptide or a cellular internalization transporter. As used herein the terms "cell penetrating peptide," "cellular internalization transporter," and "membrane translocation domain" are used interchangeably and refer to segments of polypeptide sequence that allow or promote a polypeptide to cross the cell membrane, such as the plasma membrane of a eukaryotic cell. Examples of cell penetrating peptide segments include, but are not limited to, segments derived from HIV Tat, herpes virus VP22, the *Drosophila* Antennapedia homeobox gene product, or protegrin I, penetratin (PENE), KALA, R11, K11, and polyarginine.

The herein provided polypeptides may, in certain embodiments, be directly contacted to a tissue in a subject. However, efficiency of cytoplasmic localization of the provided polypeptide may be enhanced in some embodiments by a cellular internalization transporter chemically linked in cis or trans with the polypeptide. Efficiency of cell internalization transporters are enhanced further by light or co-transduction of cells with Tat-HA peptide.

Thus, the provided polypeptide can comprise a cellular internalization transporter or sequence. The cellular internalization sequence can be any internalization sequence known or newly discovered in the art, or conservative variants thereof. The cellular internalization transporter may comprise D-amino acids or be D-isomers of a peptide or amino acid sequence. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-I, SynB1, Pep-7, HN-1, BGSC (Bis-Guanidinium-Spermidine-Cholesterol, and BGTC (BisGuanidinium-Tren-Cholesterol) and certain poly arginine (poly-R) sequences. Poly-R sequences may vary in length from 3, 4, 5, 6, 7, 8, 9, and 10 R amino acids in length. The NT of the CIS sequences may be modified, for example, by adding a lipid moiety, myristolation, or acylation, to improve uptake and stability.

Thus, the provided polypeptide can further comprise amino acid sequences and other molecules described in, e.g., Bucci et al., 2000; Derossi et al., 1994; Fischer et al., 2000; Frankel and Pabo, 1988; Green and Loewenstein, 1988; Park et al., 2000; Pooga et al., 1998; Oehlke et al., 1989; Lin et al., 1995; Sawada et al., 2003; Lundberg et al., 2002; Morris et al., 2001; Rousselle et al., 2000; Gao et al., 2002; Hong and Clayman, 2000.

A peptide of the present invention may further comprise BGSC (Bis-Guanidinium-Spermidine-Cholesterol) or BGTC (Bis-Guanidinium-Tren-Cholesterol) (Vigneron et al., 1998). The preceding references are incorporated herein by reference in their entirety for the teachings of cellular internalization vectors and sequences. Any other internalization sequences now known or later identified can be combined with a peptide of the invention.

Examples of JM peptides comprising a cell internalization sequence are provided below in Table 6. It is anticipated that any combination of a JM peptide and cell internalization sequence shown in Table 6 may be generated and used to produce a therapeutic effect in a subject.

TABLE 6

Examples of JM Polypeptides with Cell Internalization Sequences

| | |
|---|---|
| Poly-r7-JM2 | rrrr rrrr VFF KGV KDRV KGKSD (SEQ ID NO: 58) |
| Poly-r7-JM1 | rrrr rrrr VFF KGV KDRV (SEQ ID NO: 59) |
| Poly-R6-JM2 | RRR RRR VFF KGV KDRV KGKSD (SEQ ID NO: 60) |
| Poly-r5-JM1 | rrrr r VFF KGV KDRV (SEQ ID NO: 61) |
| Antp-JM1 | RQPKIWFPNRRKPWKK VFF KGV KDRV (SEQ ID NO: 62) |
| Penetratin-JM1 | RQIKIWFQNRRMKWKK VFF KGV KDRV (SEQ ID NO: 63) |
| Tat-JM2 | RKKRRQRRR VFF KGV KDRV KGKSD (SEQ ID NO: 64) |
| Tat-JM1 | rkkrrqrrr VFF KGV KDRV (SEQ ID NO: 65) |

(Cell internalization sequences are in bold. Upper case letters = L isomers, lower case letters D isomers). For example, the polypeptide may comprise a poly-r7 (i.e., 7 R aas in a sequence) sequence in the D-isomer (as indicated by lower case r) with a JM2 sequence.

Linkers/Coupling Agents

If desired, the compound of interest may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Additionally, while numerous types of disulfide-bond containing linkers are known which can successfully be employed to conjugate moieties, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the moiety prior to binding at the site of action.

Additionally, any other linking/coupling agents and/or mechanisms known to those of skill in the art can be attached to a peptide of the present invention, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

Cross-linking reagents are used to form molecular bridges that tie together functional groups of two different molecules, e.g., a stablizing and coagulating agent. However, it is contemplated that dimers or multimers of the same analog can be made or that heteromeric complexes comprised of different analogs can be created. To link two different compounds in a step-wise manner, hetero-bifunctional cross-linkers can be used that eliminate unwanted homopolymer formation.

TABLE 7

HETERO-BIFUNCTIONAL CROSS-LINKERS

| linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Protein Purification

In certain embodiments of the present invention, the polypeptide has been purified. Generally, "purified" will refer to a polypeptide composition that has been subjected to fractionation to remove various other components, and which composition substantially retains its expressed biological activity. Where the term "substantially purified" is used, this designation will refer to a composition in which the polypeptide or peptide forms the major component of the composition, such as constituting about 50% to about 99.9% or more of the proteins in the composition.

Various methods for quantifying the degree of purification of the polypeptide will be known to those of skill in the art in light of the present disclosure. Exemplary techniques include high performance liquid chromatography, ion exchange chromatography, gel electrophoresis, affinity chromatography and the like. The actual conditions used to purify a particular polypeptide will depend, in part, on factors such as net charge, hydrophobicity, hydrophilicity, etc., and will be apparent to those having skill in the art.

For affinity chromatography purification, any antibody that specifically binds the polypeptide may be used. For the production of antibodies, various host animals, including but not limited to rabbits, mice, rats, etc., may be immunized by injection with a chimeric protein or a fragment thereof. The protein may be attached to a suitable carrier, such as bovine serum albumin (BSA), by means of a side chain functional group or linkers attached to a side chain functional group. Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhold limpet hemocyanin, dinitrophenol, and potentially useful human adjuvants such as BCG (bacilli Calmetter-Guerin) and *Corynebacterium parvum*.

Monoclonal antibodies to a chimeric polypeptide may be prepared using any technique that provides for the production of antibody molecules by continuous cell lines in culture. These include but are not limited to the hybridoma technique originally described by Koehler and Milstein (1975), the human B-cell hybridoma technique (Cote et al., 1983), and the EBV-hybridoma technique (Cole et al., 1985). In addition, techniques developed for the production of "chimeric antibodies" (Morrison et al., 1984; Neuberger et al., 1984; Takeda et al., 1985) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce chimeric protein-specific single chain antibodies for chimeric protein purification and detection.

Nucleic Acids Encoding Peptides

A therapeutic peptide of the present invention may be encoded in a nucleic acid or vector. Genetic vectors (e.g., cDNA, cDNA for transfection, viral vectors and the like) expressing the amino acid sequences listed above and JM sequences or conservative variants thereof, or combinations of other factors with said vectors and peptides are also contemplated to be used in association with the provided invention.

Also provided are isolated nucleic acids encoding the polypeptides. The disclosed nucleic acids are made up of for example, nucleotides, nucleotide analogs, or nucleotide substitutes. The preparation of nucleotide sequences encoding JM peptide aa sequences and cell penetration aa sequences and JM peptide aa sequences are well known to those skilled in the art. Non-limiting examples of these and other molecules are discussed herein. It is understood that for example, when a vector is expressed in a cell, the expressed mRNA will typically be made up of A, C, G, and U.

By "isolated nucleic acid" or "purified nucleic acid" is meant DNA that is free of the genes that, in the naturally occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (e.g., a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized.

The herein provided nucleic acid can be operably linked to an expression control sequence. Also provided is a vector comprising one or more of the herein provided nucleic acids, wherein the nucleic acid is operably linked to an expression control sequence. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff et al. (1990); and Wolff (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver genes into cells (e.g., a plasmid), or as part of a general strategy to deliver genes, e.g., as part of recombinant retrovirus or adenovirus (Ram et al., 1993).

As used herein, plasmid or viral vectors are agents that transport the disclosed nucleic acids, into the cell without degradation and include a promoter yielding expression of the gene in the cells into which it is delivered. In some embodiments the promoters are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also disclosed are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a trans gene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. Also disclosed is a viral vector which has been engineered so as to suppress the immune response of the host organism, elicited by the viral antigens. Vectors of this type can carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

A retrovirus is an animal virus belonging to the virus family of Retroviridae, including any types, subfamilies, genus, or tropisms (e.g., lentivirus). Retroviral vectors, in general, are described by Verma (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan (1993), the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., 1987; Massie et al., 1986; Haj-Ahmad et al., 1986; Davidson et al., 1987; Zhang, 1993). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, 1993; Kirshenbaum, 1993; Roessler, 1993; Moullier, 1993; La Salle, 1993; Gomez-Foix, 1992; Rich, 1993; Zabner, 1994; Guzman, 1993; Bout, 1994; Zabner, 1993; Caillaud, 1993; and Ragot, 1993). Recombinant adenoviruses achieve gene transduction by binding to specific cell surface receptors, after which the virus is internalized by receptor-mediated endocytosis, in the same manner as wild type or replication-defective adenovirus (Chardonnet and Dales, 1970; Brown and Burlingham, 1973; Svensson and Persson, 1985; Seth et al., 1984; Seth et al., 1984; Varga et al., 1991; Wickham et al., 1993).

A viral vector can be based on an adenovirus which has had the E1 gene removed, and these virons are generated in a cell line such as the human 293 cell line. In some aspects, both the E1 and E3 genes are removed from the adenovirus genome.

Another type of viral vector is based on an adeno-associated virus (AAV). This defective parvovirus can infect many cell types and is nonpathogenic to humans. AAV type vectors can transport about 4 to 5 kb and wild type AAV is known to stably insert into chromosome 19. As an example, this vector can be the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B 19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral vectors usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Molecular genetic experiments with large human herpes viruses have provided a means whereby large heterologous DNA fragments can be cloned, propagated and established in cells permissive for infection with herpes viruses (Sun et al., 1994; Cotter and Robertson, 1999). These large DNA viruses (herpes simplex virus (HSV) and EpsteinBarr virus (EBV)), have the potential to deliver fragments of human heterologous DNA>150 kb to specific cells. EBV recombinants can maintain large pieces of DNA in the infected B cells as episomal DNA. Individual clones carrying human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed polypeptides, nucleic acids or vectors, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. (1989); Feigner et al. (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

The compositions can be delivered to the subject's cells in vivo and/or ex vivo by a variety of mechanisms well known in the art (e.g., uptake of naked DNA, liposome fusion, intramuscular injection of DNA via a gene gun, endocytosis, by virus and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Promoters controlling transcription from vectors in mammalian host cells may be obtained from various sources, for example, the genomes of viruses, such as polyoma, Simian Virus 40 (SV40), adenovirus, retroviruses, hepatitis-B virus, cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., 1978). The immediate early promoter of the human cytomegalovirus is conveniently obtained as a HindIII E restriction fragment (Greenway et al., 1982). Of course, promoters from the host cell or related species also are useful herein.

Enhancer generally refers to a sequence of DNA that functions at no fixed distance from the transcription start site and can be either 5' (Laimins et al., 1981) or 3' (Lusky et al., 1983) to the transcription unit. Furthermore, enhancers can be within an intron (Banerji et al., 1983) as well as within the coding sequence itself (Osborne et al., 1984). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, a-fetoprotein and insulin), typically one will use an enhancer from a eukaryotic cell virus for general expression. Examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A promoter of this type is the CMV promoter (650 bases). Other such promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. The transcription unit can also contain a polyadenylation region. One benefit of this region is that it increases the likelihood that the transcribed unit will be processed and transported like mRNA. The identification and use of polyadenylation signals in expression constructs is well established. Homologous polyadenylation signals can be used in the transgene constructs. In certain transcription units, the polyadenylation region is derived from the SV40 early polyadenylation signal and consists of about 400 bases. Transcribed units may contain other standard sequences alone or in combination with the above sequences improve expression from, or stability of, the construct.

The viral vectors can include nucleic acid sequence encoding a marker product. This marker product is used to determine if the gene has been delivered to the cell and once delivered is being expressed. Example marker genes are the E. coli lacZ gene, which encodes ~-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: Chinese hamster ovary (CHO) D HFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact D HFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern and Berg, 1982), mycophenolic acid, (Mulligan and Berg, 1980) orhygromycin, (Sugden et al., 1985). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Also provided is a cell comprising one or more of the herein provided vectors. As used herein, "cell", "cell line", and "cell culture" may be used interchangeably and all such designations include progeny. The disclosed cell can be any cell used to clone or propagate the vectors provided herein. Thus, the cell can be from any primary cell culture or established cell line. The method may be applied to any cell, including prokaryotic or eukaryotic, such as bacterial, plant, animal, and the like. The cell type can be selected by one skilled in the art based on the choice of vector and desired use. Cells expressing the disclosed compositions may be used as a vector for delivery in vivo or otherwise.

Disclosed are animals produced by the process of transfecting a cell within the animal with any of the nucleic acid molecules or vectors disclosed herein. Disclosed are animals produced by the process of transfecting a cell within the animal any of the nucleic acid molecules or vectors disclosed herein, wherein the animal is a mammal. Also disclosed are animals produced by the process of transfecting a cell within the animal any of the nucleic acid molecules or vectors disclosed herein, wherein the mammal is mouse, rat, rabbit, cow, sheep, pig, or primate and animals derived from the mating of such animals.

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

In various embodiments, a vector may comprise a promoter, enhancer, initiation signal, internal ribosome binding sites, multiple cloning site, splice site, termination signal, polyadenylation signal, origin of replication, selectable and/or screenable marker. In some embodiments, a plasmid vector or a viral vector may be used.

Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). A peptide of the present invention such as a JM peptide may be encoded by a nucleic acid comprised in a viral vector. Non-limiting examples of virus vectors that may be used to deliver a nucleic acid of the present invention are described below.

In various embodiments, the viral vector may be an adenoviral vector, an AAV vector, a retroviral vector, or a lentiviral vector. Other viral vectors that may be employed to deliver a nucleic acid encoding a peptide of the present invention include, e.g., vaccinia virus, sindbis virus, cytomegalovirus and herpes simplex virus.

Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783; 5,563,055; 5,550,318; 5,538,877; and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be transiently, stably or transgenically transformed.

Pharmaceutical Preparations

The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1289-1329, 1990, incorporated herein by reference). Except insofar as any conventional carrier is incompatible with the active ingredient, its use in compositions of the present invention is contemplated.

A pharmaceutical composition of the present invention may comprise different types of carriers depending on whether it is to be administered in solid, liquid or aerosol form, and whether it needs to be sterile for such routes of administration as injection. A pharmaceutical composition disclosed herein can be administered topically, transdermally, intravenously, intradermally, intraarterially, intraperitoneally, intralesionally, intracranially, intraarticularly, intraprostaticaly, intrapleurally, intratracheally, intranasally, intravitreally, intravaginally, intrarectally, intramuscularly, intraperitoneally, subcutaneously, subconjunctivally, intravesicularlly, mucosally, intrapericardially, intraumbilically, intraocularly, orally, locally, or by inhalation, injection, infusion, continuous infusion, lavage, or localized perfusion. A pharmaceutical composition may also be administered to a subject via a catheter, in cremes, in lipid compositions, by ballistic particle delivery, or by other method or any combination of the forgoing as would be known to one of ordinary skill in the art (see, for example, Remington: The Science and Practice of Pharmacy, 21$^{st}$ Ed. Lippincott Williams and Wilkins, 2005, incorporated herein by reference). In certain embodiments, a peptide of the present invention is comprised in a topical or transdermal formulation, e.g., that is formulated to promote healing of a wound or reduce scarring.

While any suitable carrier known to those of ordinary skill in the art may be employed in the pharmaceutical compositions of this invention, the type of carrier will vary depending on the mode of administration. For parenteral administration, such as subcutaneous injection, the carrier may comprise water, saline, alcohol, a fat, a wax or a buffer. For oral administration, a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. The pharmaceutical preparation may comprise a microcapsule, a microparticle, a microsphere, a nanocapsule, a nanoparticle, a nanosphere, or a combination thereof.

In some embodiments, the pharmaceutical preparation may comprise a liposome or lipid composition. Liposomes are well known in the art and include, e.g., unilamellar, multilamellar, and multivesicular liposomes.

In other embodiments, a pharmaceutical composition comprises an immobilized or encapsulated peptide of the present invention and a support substrate. In these embodiments, a support substrate can include, but is not limited to, a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides, have been reviewed (U.S. Pat. Nos. 5,567,434; 5,552,157; 5,565,213; 5,738,868 and 5,795,587, each of which is specifically incorporated in its entirety by reference).

A peptide may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Sterile injectable solutions are prepared by incorporating the active peptides in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsions, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, and DMSO may be used as a as solvent and may result in increased penetration, delivering high concentrations of the active agents to a small area. In particular embodiments, prolonged absorption of an injectable composition can be brought about by the use in the compositions of agents delaying absorption, such as, for example, aluminum monostearate, gelatin or combinations thereof.

The pharmaceutical composition is generally stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212. Likewise, the delivery of drugs using intranasal microparticle resins (e.g., Takenaga et al., 1998) and lysophosphatidyl-glycerol compounds (e.g., U.S. Pat. No. 5,725,871) are also well-known in the pharmaceutical arts. Likewise, transmucosal drug delivery in the form of a polytetrafluoroetheylene support matrix may be used with the present invention and is described, e.g., in U.S. Pat. No. 5,780,045.

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

The pharmaceutical preparation may also contain an antimicrobial compound. The antimicrobial compound may be an antibiotic such as, e.g., polymyxin B, neomycin, bacitracin, or triclosan. Alternately the antimicrobial compound may be an antiseptic compound such as, e.g., iodine, ethanol, isopropanol, or chlorhexidine.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

A pharmaceutical preparation may further comprise any known or newly discovered substance that can be administered to a tissue of a subject. For example, the provided composition can further comprise one or more of classes of antibiotics (e.g.

Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anticancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Di ethyl stilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Ciclo-profen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid' Flumizole-Flunisolide Acetate; Flunixin; Flunixin Meglumine; Flu~cortin Butyl; Fluorometholone Acetate; Fluquazone; Flurbiprofen; Fluretofen; Fluticasone Propi onate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; IsoflupredoneAcetate; Isoxepac; Isoxicam; Ketoprofen; Lofemizole Hydrochloride; Lomoxicam; Lotepredno Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Brompheniramine, Clemastine, Acetaminophen, Pseudoephedrine, Triprolidine).

The herein provided composition can further comprise anti-VEGF (anti-Vascular Endothelial Growth Factor) agents. Examples of these agents include Ranibizumab (Lucentis™), Bevacizumab (Avastin™) and Pegaptanib (Macugen™).

The compositions may be administered topically, orally, or parenterally. For example, the compositions can be administered extracorporeally, intracranially, intravaginally, intraanally, subcutaneously, intradermally, intracardiac, intra gastric, intravenously, intramuscularly, by intraperitoneal injection, transdermally, intranasally, or by inhalant. As used herein, "intracranial administration" means the direct delivery of substances to the brain including, for example, intrathecal, intracisternal, intraventricular or trans-sphenoidal delivery via catheter or needle.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

As used herein, "topical intranasal administration" means delivery of the compositions into the nose and nasal passages through one or both of the nares and can comprise delivery by a spraying mechanism or droplet mechanism, or through aerosolization of the therapeutic peptide, nucleic acid, or vector. Administration of the compositions by inhalant can be through the nose or mouth via delivery by a spraying or droplet mechanism. Delivery can also be directly to any area of the respiratory system (e.g., lungs) via intubation.

The exact amount of the compositions required will vary from subject to subject, depending on the species, age, weight and general condition of the subject, the severity of the disease or wound being treated, the particular therapeutic peptide, nucleic acid, or vector used, its mode of administration and the like. Thus, it is not possible to specify an exact amount for every composition. However, an appropriate amount can be determined by one of ordinary skill in the art using only routine experimentation given the teachings herein.

The materials may be in solution or suspension (for example, incorporated into microparticles, liposomes, or cells). These may be targeted to a particular cell type via antibodies, receptors, or receptor ligands. The following references are examples of the use of this technology to target specific proteins to tumor tissue (Senter et al., 1991; Bagshawe, 1989; Bagshawe et al., 1988; Senter et al., 1993; Battelli et al., 1992; Pietersz and McKenzie, 1992; and Roffier et al., 1991). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., 1989; and Litzinger and Huang, 1992). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, 1991).

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8, from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), perfusion solutions, and the like. Preservatives and other additives may also be present such as, for example, antimicrobials, anti-oxidants, chelating agents, and inert gases and the like.

Formulations for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a micro fiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

In some aspects the provided pharmaceutically acceptable carrier is a poloxamer. Poloxamers, referred to by the trade name Pluronics®, are nonionic surfactants that form clear thermoreversible gels in water. Poloxamers are polyethylene oxide-polypropylene oxide-polyethylene oxide (PEOPPO-PEO) tri-block copolymers. The two polyethylene oxide chains are hydrophilic but the polypropylene chain is hydrophobic. These hydrophobic and hydrophilic characteristics take charge when placed in aqueous solutions. The PEO-PPO-PEO chains take the form of small strands where the hydrophobic centers would come together to form micelles. The micelle, sequentially, tend to have gelling characteristics because they come together in groups to form solids (gels) where water is just slightly present near the hydrophilic ends. When it is chilled, it can liquefy, but it can harden when warmed. This characteristic makes it useful in pharmaceutical compounding because it can be drawn into a syringe for accurate dose measurement when it is cold. When it warms to body temperature (e.g., when applied to skin) it can thicken to a useful consistency (especially when combined with soy lecithin/isopropyl palmitate) to facilitate proper inunction and adhesion. Pluronic® F127 (F127) may be used in some embodiments. F127 has a EO:PO:EO ratio of 100:65:100, which by weight has a PEO:PPO ratio of 2:1. Pluronic gel is an aqueous solution and typically contains 20-30% F-127. Thus, the provided compositions can be administered in F127.

For example, in applications as a laboratory tool for research, the peptide compositions can be used in doses as low as 0.001% w/v. The dosage can be as low as 0.02% w/v and possibly as high as 10% w/v in topical treatments. Thus, upper limits of the provided polypeptides may be up to 2-10% w/v or v/v if given as an initial bolus delivered for example directly into a tumor mass. Recommended upper limits of dosage for parenteral routes of administration for example intramuscular, intracerebral, intracardicardiac and intraspinal could be up to 1% w/v or vivo This upper dosage limit may vary by formulation, depending for example on how the polypeptide(s) is combined with other agents promoting its action or acting in concert with the polypeptide(s).

For continuous delivery of the provided polypeptides, for example, in combination with an intravenous drip, upper limits of 0.01 g/kg body weight over time courses determined by the doctor based on improvement in the condition can be used. In another example, upper limits of concentration of the provided nucleic acids delivered topically would be 5-10 flg/cm$^2$ of tissue depending for example on how the nucleic acid is combined with other agents promoting its action or acting in concert with the nucleic acids. This would be repeated at a frequency determined by the doctor based on improvement. In another example, upper limits of concentration of the provided nucleic acids delivered internally for example, intramuscular, intracerebral, intracardicardiac and intraspinal would be 50-100 flg/ml of solution. The frequency would be determined by the doctor based on improvement.

Viral vectors remain highly experimental tools that nonetheless show considerable potential in clinical applications. As such, caution is warranted in calculation of expected dosage regimes for viral vectors and will depend considerably on the type of vector used. For example, retroviral vectors infect dividing cells such as cancer cells efficiently, intercalating into the host cell genome and continuing expression of encoded proteins indefinitely. Typical dosages of retroviruses in an animal model setting are in the range of $10^7$ to $10^9$ infectious units per ml. By contrast, adenoviruses may efficiently target post-mitotic cells, but cells typically are quickly eliminated by the host immune system or virus is eventually lost if infected cells resume proliferation and subsequently dilute the viral episomal DNA. Indeed, this transient time course of infection may be useful for short-term delivery of the composition described herein in certain clinical situations. In animal models, concentrations of $10^8$-$10^{11}$ infectious units per ml of adenovirus are typical for uses in research. Dose ranges of vectors based on data derived from animal models would be envisaged to be used eventually in clinical setting (s), pending the development of pharmaceutically acceptable formulation(s).

Two topical applications of the compositions at 0.02% w/v; one applied acutely and the second applied 24 hours later can be used in treating or preventing pathologies involving epithelial permeablization and/or neovascularization. However, in a clinical setting an increased frequency of up to 3 applications per day topically at a concentration of up to 5% is recommended until significant improvement is achieved as determined by a doctor. For internal administration, for example, intravenously, intramuscularly, intracerebral, intracardicardiac and intraspinally and increased frequency of up to 3 dosages of 1% w/v or v/v per day is recommended until significant improvement is determined by the doctor.

Also provided are materials comprising the compositions herein (e.g., polypeptides, nucleic acids, or vectors). For example, provided are materials coated with a JM polypeptide.

For example, the material can be soaked in the provided polypeptide at a concentration ranging from 0.1-1000 µM. The material can then be dried and sealed in a sterile container. The material can also be immersed in liquid 10-30% pluronic gel at 4° C. containing polypeptide at 0.1-1000 µM concentration. The material can then be brought to approximate room temperature so that the gel polymerizes, leaving a coat of polypeptide-impregnated gel surrounding the material, which can be sealed in a sterile container. The polypeptide can also be incorporated into a cross-linkable hydrogel system, such as the poly(lactic-co-glycolic acid) (PLGA) or polyurethane, which can then be fashioned into materials for treating a desired pathology. Thus, provided are composite hydrogel-peptide materials.

Other non-peptidergic modulating agents that can be used in association with the disclosed invention include, e.g., fatty acids; oleic acid, arachidonic acid, and lipoxygenase metabolites; aliphatic alcohols; heptanol, octanol anesthetics; halothane, propofol, ethflurane, and thiopental; anandamide; arylaminobenzoate (FFA: flufenamic acid and lipophilic derivatives); 2',5'-dihydroxychalcone; Chlorohydroxyfuranones; 3-chloro-4-chloromethyl-5-hydroxy-2(5H)-furanone; dexamethasone; doxorubicin (and derivatives); eicosanoid thromboxane A(2) (TXA(2)) mimetics; nitric oxide; Fenamates; Genistein; glycyrrhetinic acid (GA):18a-glycyrrhetinic acid and 18-beta-glycyrrhetinic acid, and derivatives thereof; lysophosphatidic acid; lindane; mefloquine; menadione; 2-Methyl-1,4-naphthoquinone, vitamin K(3); nafenopin; okadaic acid; oleamide; PH, gating by intracellular acidification; e.g. acidifying agents; polyunsaturated fatty acids; quinidine; quinine; all trans-retinoic acid; vitamin A and retinoic acid derivatives and tamoxifen.

Without wishing to be bound by any theory, a therapeutic peptide of the present invention may affect modulation of gap junctional intercellular coupling or between extracellular and the intercellular space by connexin/pannexin hemichannels, effects of connexin domains on signal transduction, enzymatic pathways, cell morphology, cell migration, adhesivity/cohesivity, chaperoning or transport of molecules, effects on ECM molecular, cellular organization or other biological processes.

As shown in the below examples and similar to ACT1, JM peptides displayed pro-healing and anti-inflammatory and acti-scarring effects (e.g., FIGS. 1 and 2). Thus, JM peptides may be used in some embodiments to promote the healing of normal wounds, including those resulting from accidents, surgery, or failure of healing of a surgical wound (e.g., a dehiscent wound). Without wishing to be bound by any theory, a JM peptide may modulate one or more biological processes including collagen production, ECM deposition, cell migration and proliferation, reducing inflammation, accelerating wound healing, reduce scarring, or promoting repair, regeneration and restoration of structure and function in a tissue. A reduction in inflammation can speed-up wound closure and consequently the process of wound healing. Healing of wounds, post-peptide application may involve significantly reduced fibrosis, consequently reduced scarring in skin wounds and fibrous patches in internal tissue injuries, promoting tissue regeneration and restoring tissue and organ structure and function.

A therapeutic peptide of the present invention may be used to treat external wounds caused by, but not limited to scrapes, cuts, lacerated wounds, bite wounds, bullet wounds, stab wounds, burn wounds, sun burns, chemical burns, surgical wounds, bed sores, radiation injuries, all kinds of acute and chronic wounds, wounds or lesions created by cosmetic skin procedures. The peptide may also be used to ameliorate the effects of skin aging. The peptide may accelerate wound healing in an external wounds and/or improve the cosmetic appearance of wounded areas, or skin subject to aging and disease. The peptide may be used to treat internal injury caused by, but not limited to, disease, surgery, gunshots, stabbing, accidents, infarcts, ischemic injuries, to organs and tissues including but not limited to heart, bone, brain, spinal cord, retina, peripheral nerves and other tissues and organs commonly subject to acute and chronic injury, disease, congenital and developmental malformation and aging processes.

Injury to internal organs causes a fibrotic response, which leads to loss of structure and function in organ systems. In central nervous system (CNS) this response to injury is mediated by astrocytes (fibroblast-like cells in the CNS) and thus will subsequently be referred to as an astrocytic response. In some embodiments a therapeutic peptide as described herein may be used to treat fibrotic/astrocytic response hence helping in repair and regeneration of injured tissues and restoration of tissue and organ structure and function.

A therapeutic peptide of the present invention may be used to induce the regenerative healing and/or medical benefit. Stem cells may be used in combination with a JM peptide or may be receptive to stimulation by a therapeutic peptide of the present invention. Stem cells include bone-marrow derived stem cells (BMSCs) and BMSCs can be substituted by other stem cell types including totipotent, omnipotent, pluripotent, multipotent, oligopotent and unipotent stem cell types, including embryonic, fetal, and adults stem cells, amniotic stem cells and other stem cells derived from the various stem cell niches and fluids found within or emanating from the bodies, mesenchymal stem cells, tissue and lineage specific stem cells and induced progenitor stem cells. Other differentiated cell types may also provide benefit following treatment in vitro or in vivo by the by the provided compositions and methods, particularly if it is combined with a regimen that reverts these cells to induced pluripotent stem cells (iPS) or iPS-like state.

In one instance, a treatment of skin wounds with a toroid of bone marrow stem cells BMSCs (prepared as described in Gourdie and Potts, Compositions and Methods for Tissue Engineering, Tissue Regeneration and Wound Healing. US Patent application, US20110086068) and the provided compositions can significantly enhance regenerative healing and inhibit scarring over that occurring for treatments with a BMSC toroid alone or the peptide alone. In another example, treatment of skin wounds with a toroid of BMSCs and TGF-beta3 may significantly enhance regenerative healing and/or inhibit scarring over that occurring for treatments with a BMSC toroid alone or the peptide alone. It is anticipated that, in some embodiments, a therapeutic peptide as disclosed herein may be used to promote processes similar to embryonal scarless healing in the neonate, postnate or adult.

The present disclosure contemplates combination of the provided composition with co-treatments known to improve healing and/or reduce scarring. The co-treatment may include, e.g., αCT1, GAP27, GAP27, GAP19, GAP134, ZP123, danepeptide, rotigaptide, AA10, connexin CT domain peptides and mimetics, connexin extracellular loop domain peptides and mimetics, connexin cytoplasmic loop domain peptides and mimetics, osteopontin, platelet-derived growth factor (PDGF), transforming growth factor and beta, TGF-B1-3, TGFb or Cx43 antisense or peptides can be of significant benefit. Other molecules that are contemplated for use with the present disclosure include bone morphogenetic proteins (BMP), epidermal growth factors (EGF), erythropoietins (EPO), fibroblast growth factors (FGF), platelet derived growth factors (PDGFs), ligands for the seven transmembrane helix family, granulocyte-colony stimulating factor (GCSF), granulocyte-macrophage colony-stimulating factor (GMCSF), growth differentiation factor-9 (GDF9), hepatocyte growth factor (HGF), hepatoma derived growth factor (HDGF), human growth hormones (HGH), interleukins (IL), insulin growth factors (IGF), insulin growth factor binding proteins (IGFBP), myostatins (GDF-8), nerve growth factors (NGF) and other neurotrophins, thrombopoietins (TPO), vascular endothelial growth factors (VEGF), caveolins, matricellular proteins (e.g., periostin, CCNs, thrombospondins), osteopontin, canonical (e.g., Wnt1, Wnt3a) and non-canonical WNTs (e.g., Wnt5a, Wnt11), interleukins, tumor necrosis factors (TNFs), Notch-Delta, hyaluronin and related molecules, Hyaluronic synthetic enzymes (e.g., HAS2, HAS3), relaxins, acetylcholine, chitosan, DMSO, N-acetyl-glucosamine, catecholamines, lipids, poly unsaturated fats, estrogens and related/derivative molecules, androgens and related molecules, inhibitors of collagen processing (e.g., prolyl 4-hydroylase, C-proteinase and lysyl hydoxylase, HRT peptidases) and NADPH oxidases, factors effecting connective tissue growth factors (CTGFs), endothelins, and angiotensins, complement proteins, bioactive fragments or polymers of these molecules, genetic or cellular vectors producing these molecules, binding proteins, molecules targeting the receptors or downstream signal transduction mediators and combinations thereof. As these molecules and their different family members can have opposing effects in different circumstances ligands, agonists (activating factors) and antagonists (or inhibiting factors) of these molecules will be used in the disclosed invention.

Regenerative processes aided by the present composition include, but are not limited to internal and external injury, regeneration of tissues, organs, or other body parts, healing and restoration of function following vascular occlusion and ischemia, brain stroke, myocardial infarction, spinal cord damage, brain damage, peripheral nerve damage, ocular damage (e.g., to corneal tissue), bone damage and other insults to tissues causing destruction, damage or otherwise resulting from, but not limited to, injury, surgery, cancer, congenital and developmental malformation, and diseases causing progressive loss of tissue structure and function, including but not limited to diabetes, bacterial, viral and prion-associated diseases, Alzheimer's disease, Parkinson's disease, HIV infection or AIDS, and other genetically determined, environmentally determined or idiopathic disease processes causing loss of tissue/organ/body part structure and function. In addition, the composition can be administered with drugs or other compounds promoting tissue and cellular regeneration including, but not limited to, trophic factors in processes including, but not limited to, brain, retina, spinal cord and peripheral nervous system regeneration (e.g., NGFs, FGFs, Neurtrophins, Neuregulins, Endothelins, GDNFs, BDNF. BMPs, TGFs, Wnts).

Said composition may help with repair after cosmetic and/or clinical procedures involving, but not limited to, controlled damage— e.g., corneal laser surgery, laser and dermabrasion/dermaplaning, skin resurfacing, and punch excision. Application of the present treatment immediately after surgery or any cosmetic procedure can be used to reduce or substantially eliminate scarring. Uses of said composition may reduce keloid scar formation. Keloid scars are common in darker skinned people, e.g., of Asian, African, or Middle Eastern descent. Keloid scar is a thick, hypertrophic puckered, itchy cluster of scar tissue that grows beyond the edges of a wound or incision. Keloid scars are sometimes very nodular in nature, and they are often darker in color than surrounding skin. They occur when the body continues to produce tough, fibrous protein (known as collagen) after a wound has healed. Application of the present treatment may be used to ameliorate formation of Keloid or hypertrophic scars.

A therapeutic peptide of the present invention may be used to treat a disease or other condition (e.g., congenital and developmental defects, aging) associated with inflammatory responses, fibrosis, or a connective tissue disorder. Fibrosis is a common condition noted after trauma to any bodily organ or tissue. Excessive fibrosis can result in loss of structure and function and scarring at the trauma site. The present treatment may reduce fibrosis and promote regeneration, and restoration of structure and function.

The therapeutic peptide may modulate collagen production, scar formation, or cell proliferation. The peptide may be used alone or in association with drugs used in the treatment of uncontrolled proliferation (e.g., anti-cancer drugs) and procedures (e.g., radiation therapy). Diseases of uncontrolled cell proliferation, or hyperplasias, are common health problems. Examples of diseases of cell over-proliferation include but are not limited to psoriasis, seborrhea, scleroderma, eczema, benign prostate hyperplasia, congenital adrenal hyperplasia, endometrial hyperplasia, squamous cell (vulvular) hyperplasia, sebaceous hyperplasia, Crohn's Disease, leukemia, carcinoma, sarcoma, glioma, and lymphoma. The present composition limits undesirable cellular proliferation and may thus be used to improve prognosis of conditions associated with excessive cell proliferation.

The therapeutic peptide may affect cell migration, proliferation, or differentiation. In some embodiments the peptide may be administered to reduce metastasis. The peptide may be administered alone or in association with drugs or procedures used in the treatment of metastasis including, but not limited to, Altretamine, Asparaginase, Bleomycin, Busulfan, Carboplatin, Carmustine, Chlorambucil, Cisplatin, Cladribine, Cyclophosphamide, Cytarabine, Dacarbazine, Di ethyl stilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine. Metastasis is the spread of cancer from its primary site to other places in the body. Cell migration is the movement of cells from one part of the body to another. The present treatments effects on cell migration demonstrates its ability to inhibit spread of tumors.

The actual required amount of a composition of the present invention administered to a subject can be determined by physical and physiological factors such as body weight, severity of condition, the type of disease being treated or prevented, previous or concurrent therapeutic interventions, idiopathy of the patient and on the route of administration. The practitioner responsible for administration will, in any event, determine the concentration of active ingredient(s) in a composition and appropriate dose(s) for the individual subject.

For systemic administration, a therapeutically effective dose can be estimated initially from in vitro assays. Initial dosages can also be estimated from in vivo data, e.g., animal models, using techniques that are well known in the art. One having ordinary skill in the art could readily optimize administration to humans based on animal data.

The composition can be formulated with a pharmaceutically acceptable carrier to provide the desired final concentration for site-specific, transient or systemic effect in association with the provided invention.

The route of delivery of compositions, preparations and medicaments of the invention can be in gels, oils, foams, sprays, ointments, suspensions, instillations, salves, creams, solutions, emulsions, lotions, paints, sustained release formulations, or powders, and typically contain active concentrations that will be the same as those listed above for integral administration.

The disclosed invention can also be combined with a pharmaceutically acceptable carrier or diluent to provide a pharmaceutical composition. Suitable for this are isotonic saline solutions, water, saline, dextrose, glycerol, or the like, and combinations thereof. In addition substances such as emulsifying agents, stabilizing or pH buffering agents can be present.

The composition can be administered topically, orally, or parenterally. For example, the compositions can be administered extracorporeally, intracranially, intravaginally, ophthalmically intraanally, rectally, subcutaneously, intradermally, intracardiac, intragastric, intravenously, intramuscularly, by intraperitoneal injection, transdermally, intranasally, or by inhalant. As used herein, "intracranial administration" means the direct delivery of substances to the brain including, for example, intrathecal, intracisternal, intraventricular or trans-sphenoidal delivery via catheter, needle or intravenous drip.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients, such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels (e.g., poloxamer gel), drops, suppositories, sprays, liquids and powders. Conventional pharmaceutical carriers, aqueous, powder or oily bases, thickeners and the like can be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or all bio-engineered materials.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the compositions can be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual doctor in the event of counter indications. Dosage can vary, and can be administered in one or more dose administrations daily, for one or several days. Guidance can be found in the literature for appropriate dosages for given classes of pharmaceutical products. Anaphylactic not usually dose dependent.

The dose effective for the provided composition for a given subject or wound can be determined by experimenting via methods known to those skilled in the art or developed by experimentation by those skilled in the art using culture, animal models and other biomedical approaches. Therapeutically effective doses are those that render therapeutic benefit in at least 50% of the population, and that show minimal, low or no toxicity at the effective dose. Other factors such as the route of administration, frequency of administration, and patient age, sex, weight, health, disease-profile, and other relevant medical information, the wound exhibited by the subject and the modulating agent that is being used will be also used to calculate effective dose. For example depending on the size of the wound treated and scale of the composition dose can have to be adjusted accordingly. Different active agents can be delivered together or separately, and simultaneously or at different times within the day. The doses can be administered in single or divided applications and given at repeat intervals over a time course beneficial to the subject or suitable for the therapeutic use at hand.

A suitable dose of the composition can be based on the mass of modulating agent per kg of body weight of the patient, and include, from ~0.00002 to about 200 mg/kg body weight e.g., 0.002 to about 50 mg/kg body weight. A suitable dose can however be from ~0.0002 to 0.2 mg/kg body weight e.g., 0.002 to about 0.060 mg/kg body weight. Doses from ~1 to 100, 200, 300, 400, 500, 1000, 2000 micrograms per administration are appropriate. In certain embodiments, modulating agent composition can be used at ~0.0001 micromolar ($\mu M$) or 0.06 $\mu M$ to about 300 $\mu M$, or up to 500 $\mu M$ or up to 1500 $\mu M$, or up to 3000 $\mu M$ or up to 4200 $\mu M$ or more, final concentration at the treatment site and/or adjacent to the treatment site, and any doses and dose ranges within these dose numbers.

The composition can be present in direct association with for example a tissue engineered device or present in a substantially isolated form; a state that will not change following mixing with carriers or diluents. The composition can be administered integral with a hydrogel or tissue engineered construct. In this case the provided agent will be dissolved in solution within the solution of the hydrogel or can be present as particles, nano-particles or some other vector that releases the agent into the healing tissue. The agent can also chemically bonded to the molecules of hydrogel itself. The hydrogel will contain ~001% to about 1.5% of active ingredient(s), about 2%-60% of active ingredient(s), ~2%-70% of active ingredient(s), or up to ~90% of active ingredient(s).

The skin provides one example of scar reduction/regenerative healing effects that are anticipated for JM peptides based on data including performance in the experiments on implants (see, e.g., FIGS. 12 and 13) and relative to ACT1. The present disclosure provides examples of and also contemplates the composition being of use in the regenerative repair and scar reduction in various tissues and organs including the skin, heart, brain, spinal cord and eye. The benefits would apply following injury, surgery, medication, chronic or acute disease, malformation and other normal or pathological processes causing loss of tissue structure and function, pathology and/or replacement with scar tissue.

Treatment of Disease

Peptides of the present invention may be used, in some aspects, to treat a disease. The peptides provided herein above may be given in association with the invention, such as described herein as a therapy or medicament to improve the healing of wounds, injuries, disease processes, surgeries, congenital malformations and regenerating tissue in a subject. Peptides of the present invention may be used in a cellular therapy to synchronize healing, scar reduction, and/or regenerative capacity. A composition comprising a JM peptide may be used to promote or assist in the regeneration of a tissues, organ, or body part. In some embodiments, but not limited to organ/tissue or body part transplantation of engrafted cells.

Compositions of the present invention may be used to treat a wound. The wound may result from a trauma or a disease. In some embodiments, the wound is a slow healing wound, such as, e.g., diabetic wounds. Diabetic wounds are examples of difficult to heal wound can include, for example, a wound that is often characterized by slower than normal re-epithelialization/closure inflammatory phase and delayed formation and remodeling of extracellular matrix.

The disclosed invention can also assist in the healing of chronic wounds or wounds that appear to not completely heal. Wounds that have not healed within three months, for example, are said to be chronic. Chronic wounds include, diabetic, diabetic foot ulcers, ischemic, venous ulcers, venous leg ulcers, venous stasis, arterial, pressure, vasculitic, infectious, decubitis, burn, trauma-induced, gangrenous and mixed ulcers. Chronic wounds include wounds that are characterized by and/or chronic inflammation, deficient and overprofuse granulation tissue differentiation and failure of re-epithelialization and wound closure and longer repair times. Chronic wounds can include ocular ulcers, including corneal ulcers. Use of the disclosed invention in would healing and tissue regeneration would include in humans and agricultural, sports and pet animals.

A further embodiment of the invention comprises the use of the composition to alleviate the symptoms of multiple sclerosis (MS). MS is a chronic disease of the central nervous system. Pathologically, MS is characterized by the presence of areas of demyelination and T-cell predominant perivascular inflammation in the brain white matter. The anti-inflammatory, ant-scarring and regenerative properties of our treatment will help in the treatment of MS and other conditions similar to it.

The disease may be psoriasis, scleroderma, acne, eczema, or a disease of the skin and/or connective tissues. Psoriasis, a chronic, inflammatory and scarring skin disease characterized by an uncontrolled shedding of the skin and afflicts millions of people throughout the world. The effects of our treatment on fibroblasts and inflammatory response of the treatments, as stated in the claims above, will help alleviate psoriasis. Eczema is characterized by painful swelling, oozing of the skin, bleeding cracks, severe scaling, itching and burning. As stated above, the effects of our treatment on fibroblasts and inflammatory response, combined with accelerated healing properties will relieve symptoms of eczema.

It is anticipated that the regenerative effects of a composition comprising a therapeutic peptide of the present invention may result in beneficial changes in membrane excitability and ion transients of the heart, nervous system, uterus and other tissues in health and disease.

There are many different types of arrhythmia that can lead to abnormal function in the human heart. All forms of arrhythmia have associated morbidity and can have the potential to result in sudden cardiac death (SCD). Tachyarrhythmias, like ventricular tachycardia and ventricular fibrillation are the predominant mechanisms leading to SCD. In the clinic, SCD is most commonly linked to coronary artery disease and subsequent transient ischemia. These episodes of transient ischemia can induce gap junction remodeling in un-injured tissues, and this remodeling can then cause arrhythmia.

Common arrhythmias include bradycardias, tachycardias, automaticity defects, reentrant arrhythmias, fibrillation, AV nodal arrhythmias, atrial arrhythmias and triggered beats. It is anticipated that the said composition, in addition its use in regenerative restoration of heart structures. will be used to treat cardiac rhythm disturbances of these types.

There are many diseases of congenital, genetic and acquired origins that manifest as a primarily electrical pathophysiology. In such cases accompanying tissue injury is not a factor in the generation of the arrhythmogenic substrate, that may or may not include excessive scarring and fibrosis and infiltration of scar tissue into normal myocardium. These include, but are not limited to, Long QT syndrome, Short QT syndrome, Brugada syndrome, and several accessory pathway disorders. One example, Wolff-Parkinson-White syndrome (WPW) is a condition where an accessory bundle of muscle, expressing electrical connection, links the atrium and the ventricle of the subject. This additional pathway provides the substrate for a reentrant circuit between the atrium and the ventricle which when activated can result in ventricular tachycardia, and potentially lead to SCD. The inventors contemplate that treatment of the subject with the composition will modulate the likelihood of this reentrant pathway to become activated. It is anticipated that this effect may result from the modulation of membrane excitability in the region of reentrant activity, as well as production of fibrotic and scar tissue in the diseased heart.

Arrhythmias can also be the result of molecular abnormalities in the working myocardium. These molecular abnormalities can be caused by the cellular response to environmental stress, genetic mutations, infection, and other conditions. One example of this type of disease is Hypertrophic Cardiomyopathy (HCM). HCM is the number one cause of sudden cardiac death in patients under 30 years of age. This disease can be transmitted genetically and results in the unchecked growth of the myocardium without any signs of injury. It can be diagnosed with a preventative physical exam and/or thorough family history. In this condition, gap junction remodeling in the hypertrophic working myocardium leads to the increased incidence of arrhythmia and can cause SCD. This outcome is often seen as the otherwise healthy young person who suddenly dies after a period of exercise. Examples of such subjects occasionally can be seen in media stories concerning young prominent athletes who die suddenly of an unexpected heart attack. It is contemplated that treatment with the provided composition may prevent or reduce the occurrence of unexpected arrhythmias in these subjects.

Other common arrhythmias include premature atrial Contractions, wandering Atrial pacemaker, Multifocal atrial tachycardia, Atrial flutter, Atrial fibrillation, Supraventricular tachycardia, AV nodal reentrant tachycardia is the most common cause of Paroxysmal Supraventricular Tachycardia, Junctional rhythm, Junctional tachycardia, Premature junctional complex, Wolff-Parkinson-White syndrome, Lown-Ganong-Levine syndrome, Premature Ventricular Contractions (PVC) sometimes called Ventricular Extra Beats, Accelerated idioventricular rhythm, Monomorphic Ventricular tachycardia, Polymorphic ventricular tachycardia, Ventricular fibrillation, First degree heart block, which manifests as PR prolongation, Second degree heart block, Type 1 Second degree heart block, Type 2 Second degree heart block, Third degree heart block. It is anticipated that the composition can be used to treat cardiac rhythm disturbances of these types.

Common drugs used for arrhythmia treatments include class Ia drugs, e.g., Quinidine, Procainamide, Disopyramide, class Ib drugs e.g., Lidocaine, Phenytoin, Mexiletine, class Ic drugs e.g., Flecainide, Propafenone, Moricizine, class II drugs e.g., Propranolol, Esmolol, Timolol, Metoprolol and Atenolol, class III drugs, e.g., Amiodarone, Sotalol, Ibutilide and Dofetilide, class IV drugs, e.g., Verapamil, Diltiazem and class V drugs e.g., Adenosine and Digoxin. A JM peptide may be provided to a subject alone or together with other components, such as an anti-arythmia drug, may be used in conjunction with these approaches to treatment of an arrhythmia.

Other arrhythmia treatments include: Anticoagulant therapies, electrical treatments, electrical cautery, cryo-ablation, radio frequency ablation, implantable cardioverter-defibrillator, and implantable pacemaker. The composition may be used in association with these approaches for the treatment of arrhythmia (e.g., αCT1).

Another condition that the said composition is contemplated to treat is Heart failure (HF) or congestive heart failure (CHF). Common causes of CHF include myocardial infarction (MI) and other types of ischemic heart disease, cardiomyopathy, hypertension, and cardiac valve disease. CHF is a frequent, expensive, debilitating, and potentially fatal disease in developed countries, effecting approximately 2% of adults. For individuals over the age of 65, the disease rate is as high as 10% of the adult population.

Disease resulting from systolic dysfunction is one of more readily recognized manifestations of CHF. It is characterized by ventricular ejection fractions of less than 45%, resulting in insufficient output of blood from the heart. In general, this failure of the pump caused by dysfunction or destruction of cardiac myocytes and the replacement of muscle cells by scar or fibrotic tissue. A general diffuse fibrosis is also often seen in CHF. The most common cause of this type of tissue damage is ischemia. After MI, expired cardiomyocytes are substituted by scar tissue, negatively affecting the mechanical performance of the myocardium—a characteristic which can be imaged in a patient by echocardiogram and manifest by abnormal or absent motion of the ventricular wall.

It is contemplated that said composition can be used as a treatment for CHF. This includes alone or in conjunction with other acute treatments usually such as commonly used vasodilators (nitroglycerin, diuretics such as furosemide) and in longerterm management of the disease including therapies such as angiotensin-converting enzyme (ACE) inhibitors (i.e., enalapril, captopril, lisinopril, ramipril), or in patients with severe cardiomyopathy, in conjunction with a implanted automatic defibrillator.

In peripheral vascular diseases (PVD) arterial and/or venous flow is lowered, causing an imbalance between the supply of blood and proper levels of oxygenation of tissue. PVD includes acute arterial thrombosis, chronic peripheral arterial occlusive disease (PAOD), acute arterial thrombosis and embolism, Raynaud's phenomenon, inflammatory vascular disorders and venous and arterial disorders. It is contemplated that said composition can be used as a treatment of PVD.

During atherosclerosis vessel wall is remodeled, with deleterious effects on the lumen of the vessel. Atherosclerotic remodeling involves accumulation of smooth muscle cells and monocytic or monocyte-derived inflammatory cells, in the vessel wall intima. These cells accumulate lipid, resulting in the form a mature atherosclerotic lesion. The most serious consequences associated with atherosclerosis occur when a lesion ruptures. This breakdown of the atherosclerotic lesion releases thrombogenic material that acutely can lead to blockade of an artery, including a coronary or carotid artery. In the case of a coronary arterial blockade will cause a myocardial infarction (or heart attack) and potentially sudden death from cardiac arrhythmia. In the case of a carotid artery, released thrombolytic debris may lodge in and occlude a cerebral artery leading to vascular stroke in the brain, causing death of CNS tissue with attendant acute and chronic effects on CNS function, and possibly also resulting in death. It is contemplated that said composition can be used as a treatment of atherosclerosis, with uses in treatment in heart attack and stroke.

Epilepsy is a chronic neurological disorder characterized by recurrent, transient, unprovoked seizures, resulting from disturbed neuronal activity in the brain. There is evidence that epilepsy is caused by dysregulated connexin coupling between neuronal cells and disturbances to Cx43 have been noted in human hippocampus associated with severe epilepsy. Over 50 million people worldwide have epilepsy. Over 30% of people with epilepsy do not respond to currently available medications. The uncontrolled electrical disturbance associated with epilepsy often leads to comparisons to cardiac arrhythmias.

Common forms of epilepsy include: Autosomal dominant nocturnal frontal lobe epilepsy, Benign centrotemporal lobe epilepsy of childhood, Benign occipital epilepsy of childhood, Catamenial epilepsy, Childhood absence epilepsy, Dravet's syndrome, Frontal lobe epilepsy, Juvenile absence epilepsy, Juvenile myoclonic epilepsy, Lennox-Gastaut syndrome, Primary reading epilepsy, Progressive myoclonic epilepsies, Rasmussen's encephalitis, Symptomatic localization-related epilepsies, Temporal lobe epilepsy, West syndrome. The composition may be used to treat these epilepsies.

The following medications are used for treatment of epilepsy: carbamazepine, clorazepate (Tranxene) clonazepam (Klonopin), ethosuximide (Zarontin), felbamate (Felbatol), fosphenytoin (Cerebyx), gabapentin (Neurontin), lamotrigine (Lamictal), levetiracetam (Keppra), oxcarbazepine (Trileptal), phenobarbital (Luminal), phenytoin (Dilantin), pregabalin (Lyrica), primidone (Mysoline), tiagabine (Gabitril), topiramate (Topamax), valproate semisodium (Depakote), valproic acid (Depakene), zonisamide (Zonegran), clobazam (Frisium) and vigabatrin (Sabril), retigabine, brivaracetam, and seletracetam, diazepam (Valium, Diastat) and lorazepam (Ativan), Paral, midazolam (Versed), and pentobarbital (Nembutal), acetazolamide (Diamox), progesterone, adrenocorticotropic hormone (ACTH, Acthar), various corticotropic steroid hormones (prednisone), or bromide. The composition may be used in association with an additional drugs or therapy in the treatment of epilepsy. Other epilepsy treatments include: ketogenic diet, electrical stimulation, vagus nerve stimulation, responsive neurostimulator system (rns), deep brain stimulation, invasive or noninvasive surgery, avoidance therapy, warning systems, alternative or complementary medicine.

Provided herein compositions and methods are contemplated for treating or preventing pathologies involving epithelial permeablization and/or neovascularization (e.g., angiogenesis or vasculogenesis), comprising administering to the subject a polypeptide comprising a JM peptide or a conservative variant thereof.

In some aspects, the epithelial permeablization and/or neovascularization of the disclosed methods is mediated by vascular endothelial growth factor (VEGF), which promotes vascular permeability and angiogenesis/vasculogenesis.

For example, provided are compositions and methods of treating or preventing respiratory distress syndrome (RDS) in a subject, comprising: identifying a subject having or at risk of having said RDS, and administering to the lung of the subject a polypeptide disclosed herein.

Also provided are compositions and methods of treating or preventing ischemia in a subject, comprising: identifying a subject having or at risk of having said ischemia symptoms, and administering to the lung of the subject a polypeptide disclosed herein.

Also provided are compositions and methods of treating or preventing hemorrhagic stroke in a subject, comprising: identifying a subject having or at risk of having said stroke, and administering to the lung of the subject a polypeptide disclosed herein.

Also provided is a method of treating or preventing reperfusion injury, such as that observed in myocardial infarction and stroke, in a subject, comprising: identifying a subject having or at risk of having said reperfusion injury, and administering to the lung of the subject a polypeptide disclosed herein.

Also provided are compositions and methods of treating or preventing a dermal vascular blemish or malformation in a subject, comprising: identifying a subject having or at risk of having said blemish, and administering to the skin of the subject a polypeptide disclosed herein.

Also provided herein are compositions and methods of treating or preventing macular degeneration in a subject, comprising administering to the subject a therapeutically effective amount of an isolated polypeptide comprising JM peptides or a conservative variant thereof.

Also provided herein is a method of treating or preventing macular degeneration in a subject comprising: identifying a subject having or at risk of having said macular degeneration, and administering to the eye of the subject a polypeptide disclosed herein.

By "macular degeneration" is meant the degeneration of the center of the inner lining of the eye, known as the macula. In some aspects, the macular degeneration is age-related macular degeneration (AMD). In some aspects, the macular degeneration is neovascular or exudative AMD, the wet form of advanced AMD.

Also provided are compositions and methods of reducing or preventing neovascularization of choriocapillaries through Bruch's membrane.

In some aspects, the subject has been diagnosed with macular degeneration. In some aspects, the subject has been identified as being at risk of developing macular degeneration. Thus, the subject can be anyone over 50, 60, 65, 70, and 75 years of age. In some aspects, the subject is known to smoke tobacco. In some aspects, the subject is known to have a relative with macular degeneration. In some aspects, the subject has been identified as having a single nucleotide polymorphism (SNP) associated with macular degeneration. For example, the SNP can be complement system protein factor H(CFH) Tyr402H. As another example, the SNP can be rsl 1200638 in HTRAI. In some aspects, the subject has been identified as having high blood pressure. In some aspects, the subject has been identified as having high cholesterol. In some aspects, the subject is obese. In some aspects, the subject has been identified as having drusen in the macula. In some aspects, the subject has been identified as having abnormal neovascularization of choriocapillaries through Bruch's membrane.

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. According to the American Academy of Ophthalmology, it is the leading cause of central vision loss (blindness) in the United States today for those over the age of fifty years. Although some macular dystrophies that affect younger individuals are sometimes referred to as macular degeneration, the term generally refers to age-related macular degeneration (AMD or ARMD).

Age-related macular degeneration begins with characteristic yellow deposits in the macula called drusen between the retinal pigment epithelium and the underlying choroid. Thus, also provided are compositions and methods of reducing or preventing drusen in the macula of a subject. Drusen are tiny yellow or white accumulations of extracellular material that build up in Bruch's membrane of the eye. The presence of a few small ("hard") drusen is normal with advancing age, and most people over 40 have some hard drusen. However, the presence of larger and more numerous drusen in the macula is a common early sign of age-related macular degeneration (AMD). Drusen associated with aging and macular degeneration are distinct from optic disc drusen, which are present in the optic nerve head. Both age-related drusen and optic disc drusen can be observed by ophthalmoscopy.

Most people with these early changes (referred to as age-related maculopathy) have good vision. People with drusen can go on to develop advanced AMD. The risk is considerably higher when the drusen are large and numerous and associated with disturbance in the pigmented cell layer under the macula. Recent research indicates that large and soft drusen are related to elevated cholesterol deposits and can respond to cholesterol lowering agents or the Rheo Procedure.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. Vitamin supplements with high doses of antioxidants, lutein and zeaxanthin, have been demonstrated by the National Eye Institute and others to slow the progression of dry macular degeneration and in some patients, improve visual acuity.

Neovascular or exudative AMD, the wet form of advanced AMD, causes vision loss due to abnormal blood vessel growth in the choriocapillaries, through Bruch's membrane, ultimately leading to blood and protein leakage below the macula. Bleeding, leaking, and scarring from these blood vessels eventually cause irreversible damage to the photoreceptors and rapid vision loss if left untreated.

Anti-angiogenics or anti-VEGF (anti-Vascular Endothelial Growth Factor) agents, when injected directly into the vitreous humor of the eye using a small needle, can cause regression of the abnormal blood vessels and improvement of vision. The injections frequently have to be repeated on a monthly or bi-monthly basis. Examples of these agents include Lucentis, Avastin and Macugen.

The Amsler Grid Test is one of the simplest and most effective methods for patients to monitor the health of the macula. The Amsler Grid is essentially a pattern of intersecting lines (identical to graph paper) with a black dot in the middle. The central black dot is used for fixation (a place for the eye to stare at). With normal vision, all lines surrounding the black dot will look straight and evenly spaced with no missing or odd looking areas when fixating on the grid's central black dot. When there is disease affecting the macula, as in macular degeneration, the lines can look bent, distorted and/or missing.

Macular degeneration by itself will not lead to total blindness. For that matter, only a very small number of people with visual impairment are totally blind. In almost all cases, some peripheral vision remains. Other complicating conditions may possibly lead to such an acute condition (severe stroke or trauma, untreated glaucoma, etc.), but few macular degeneration patients experience total visual loss. The area of the macula comprises about 5% of the retina and is responsible for about 35% of the visual field. The remaining 65% (the peripheral field) remains unaffected by the disease.

Similar symptoms with a very different etiology and different treatment can be caused by Epiretinal membrane or macular pucker or leaking blood vessels in the eye.

Fluorescein angiography allows for the identification and localization of abnormal vascular processes. Optical coherence tomography is now used by most ophthalmologists in the diagnosis and the follow-up evaluation of the response to treatment by using either Avastin or Lucentis which are injected into the vitreous of the eye at various intervals.

Juvenile macular degeneration is not a term in standard usage at this time. The preferred term for conditions that affect the macula in younger individuals related to genetics is macular dystrophy. Examples of these include: Best's disease, Doyne's honeycomb retinal dystrophy, Sorsby's disease, and Stargardt's disease.

In some aspects, subjects are identified by medical diagnosis. For example, subjects with diabetic retinopathy and macular degeneration can be identified by visualization of excess blood vessels in the eyes. Acute lung injury can be diagnosed by lung edema in the absence of congenital heart failure. Ischemic stroke can be diagnosed by neurologic presentation and imaging (MRI and CT). Other known or newly discovered medical determinations can be used to identify subjects for use in the disclosed methods.

In addition, subjects can be identified by genetic predisposition. For example, genes that predispose patients to age related macular degeneration have been identified (Klein R J, et al, 2005; Yang Z, et al. 2006; Dewan A, et al. 2006). Likewise, genetic mutations that predispose patients to vascular malformations in the brain have been identified (Zhang J et al., 2001). Other known or newly discovered genetic determinations can be used to identify subjects for use in the disclosed methods.

Also provided are compositions and methods of treating or preventing diabetic retinopathy in a subject comprising: identifying a subject having or at risk of having said diabetic retinopathy, and administering to the retina of the subject a polypeptide disclosed herein.

Diabetic retinopathy is damage to the retina caused by complications of diabetes mellitus, which could eventually lead to blindness. It is an ocular manifestation of systemic disease which affects up to 80% of all diabetics who have had diabetes for 10 years or more. Despite these statistics, research indicates that at least 90% of these new cases could be reduced if there was proper and vigilant treatment and monitoring of the eyes.

Diabetic retinopathy often has no early warning signs. Even macular edema, which can cause vision loss more rapidly, may not have any warning signs for some time. In general, however, a person with macular edema is likely to have blurred vision, making it hard to read or drive, for example. In some cases, the vision will get better or worse during the day.

As new blood vessels form at the back of the eye as a part of proliferative diabetic retinopathy (PDR), they can bleed (haemorrhage) and blur vision. The first time this happens, it may not be very severe. In most cases, it will leave just a few specks of blood, or spots, floating in a person's visual field, though the spots often go away after a few hours.

These spots are often followed within a few days or weeks by a much greater leakage of blood, which blurs vision. In extreme cases, a person will only be able to tell light from dark in that eye. It may take the blood anywhere from a few days to months or even years to clear from the inside of the eye, and in some cases the blood will not clear. These types of large hemorrhages tend to happen more than once, often during sleep.

Diabetic retinopathy is the result of microvascular retinal changes. Hyperglycemia-induced pericyte death and thickening of the basement membrane lead to incompetence of the vascular walls. These damages change the formation of the blood-retinal barrier and also make the retinal blood vessels become more permeable.

Small blood vessels-such as those in the eye-are especially vulnerable to poor blood sugar control. An overaccumulation of glucose and/or fructose damages the tiny blood vessels in the retina. During the initial stage, called nonproliferative diabetic retinopathy (NPDR), most people do not notice any change in their vision.

Some people develop a condition called macular edema. It occurs when the damaged blood vessels leak fluid and lipids into the macula, the part of the retina that lets us see detail. The fluid makes the macula swell, which blurs vision.

As the disease progresses, severe nonproliferative diabetic retinopathy can enter an advanced, or proliferative, stage. The lack of oxygen in the retina causes fragile, new, blood vessels to grow along the retina and into the clear, gel-like vitreous humour that fills the inside of the eye. Without timely treatment, these new blood vessels can bleed, cloud vision, and destroy the retina. Fibrovascular proliferation can also cause tractional retinal detachment. New blood vessels can also grow into the angle of the anterior chamber of the eye and cause neovascular glaucoma. Nonproliferative diabetic retinopathy shows up as cotton wool spots (microinfarction of the retina), lipid exudate, intraretinal microvascular abnormalities (IRMA), or microvascular abnormalities or as superficial retinal hemorrhages. Even so, the advanced proliferative diabetic retinopathy (PDR) can remain asymptomatic for a very long time, and so should be monitored closely with regular checkups.

All people with diabetes mellitus are at risk (those with Type I diabetes Juvenile onset) and those with Type II diabetes (adult onset). The longer a person has diabetes, the higher the risk of developing some ocular problem. Between 40 to 45 percent of Americans diagnosed with diabetes have some stage of diabetic retinopathy. After 20 years of diabetes, nearly all patients with type 1 diabetes and >60% of patients with type 2 diabetes have some degree of retinopathy.

Diabetic retinopathy is detected during an eye examination that includes Visual acuity test, Pupil dilation, Ophthalmoscopy, Ocular Coherence Tomography or OCT, Tonometry, Digital Retinal Screening Programs, and Slit Lamp Biomicroscopy Retinal Screening Programs.

Visual acuity test uses an eye chart to measure how well a person sees at various distances (i.e., visual acuity). During Pupil dilation, the eye care professional places drops into the eye to widen the pupil. This allows him or her to see more of the retina and look for signs of diabetic retinopathy. After the examination, close-up vision may remain blurred for several hours. Ophthalmoscopy is an examination of the retina in which the eye care professional: (1) looks through a device with a special magnifying lens that provides a narrow view of the retina, or (2) wearing a headset with a bright light, looks through a special magnifying glass and gains a wide view of the retina. Note that hand-held ophthalmoscopy is insufficient to rule out significant and treatable diabetic retinopathy. OCT is a scan similar to an ultrasound which is used to measure the thickness of the retina. It produces a cross section of the retina and can determine if there is any swelling or leakage. Tonometry is a standard test that determines the fluid pressure (intraocular pressure) inside the eye. Elevated pressure is a possible sign of glaucoma, another common eye problem in people with diabetes. Digital Retinal Screening Programs are systematic programs for the early detection of eye disease including diabetic retinopathy are becoming more common, such as in the UK, where all people with diabetes mellitus are offered retinal screening at least annually. This involves digital image capture and transmission of the images to a digital reading center for evaluation and treatment referral. See Vanderbilt Ophthalmic Imaging Center and the English National Screening Program for Diabetic Retinopathy. Slit Lamp Biomicroscopy Retinal Screening Programs are systematic programs for the early detection of diabetic retinopathy using slit-lamp biomicroscopy. These exist either as a standalone scheme or as part of the Digital program (above) where the digital photograph was considered to lack enough clarity for detection and/or diagnosis of any retinal abnormality.

The eye care professional can look at the retina for early signs of the disease, such as: (1) leaking blood vessels, (2) retinal swelling, such as macular edema, (3) pale, fatty deposits on the retina (exudates), signs of leaking blood vessels, (4) damaged nerve tissue (neuropathy), and (5) any changes in the blood vessels. If the doctor suspects macular edema, he or she can perform a test called fluorescein angiography. In this test, a special dye is injected into the arm. Pictures are then taken as the dye passes through the blood vessels in the retina. This test allows the doctor to find the leaking blood vessels and areas of non-perfusion.

Treatments for diabetic retinopathy include laser surgery, injection of triamcinolone into the eye, and vitrectomy. Laser photocoagulation can be used in two scenarios for the treatment of diabetic retinopathy. Panretinal photocoagulation, or PRP (also called scatter laser treatment), is used to treat proliferative diabetic retinopathy (PDR). The goal is to create 1,000-2,000 burns in the retina with the hope of reducing the retina's oxygen demand, and hence the possibility of ischemia. In treating advanced diabetic retinopathy, the burns are used to destroy the abnormal blood vessels that form in the retina. This has been shown to reduce the risk of severe vision loss for eyes at risk by 50%.

Before the laser, the ophthalmologist dilates the pupil and applies anesthetic drops to numb the eye. In some cases, the doctor also can numb the area behind the eye to prevent any discomfort. The patient sits facing the laser machine while the doctor holds a special lens to the eye. The physician can use a single spot laser or a pattern scan laser for two dimensional patterns such as squares, rings and arcs. During the procedure, the patient may see flashes of light. These flashes may eventually create an uncomfortable stinging sensation for the patient. After the laser treatment, patients should be advised not to drive for a few hours while the pupils are still dilated. Vision can remain a little blurry for the rest of the day, though there should not be much pain in the eye.

Rather than focus the light on a single spot, the eye care professional can make hundreds of small laser burns away from the center of the retina, a procedure called scatter laser treatment or panretinal photocoagulation. The treatment shrinks the abnormal blood vessels. Patients can lose some of their peripheral vision after this surgery, but the procedure saves the rest of the patient's sight. Laser surgery can also slightly reduce color and night vision.

A person with proliferative retinopathy will always be at risk for new bleeding as well as glaucoma, a complication from the new blood vessels. This means that multiple treatments can be required to protect vision.

Triamcinolone is a long acting steroid preparation. When injected in the vitreous cavity, it results in a decrease in the macular edema (thickening of the retina at the macula) caused due to diabetic maculopathy, along with an increase in the visual acuity. The effect of triamcinolone is transient, lasting up to three months, and necessitating repeated injections for maintaining the beneficial effect. Complications of intravitreal injection of triamcinolone include cataract, steroid induced glaucoma and endophthalmitis.

Instead of laser surgery, some people need an eye operation called a vitrectomy to restore vision. A vitrectomy is performed when there is a lot of blood in the vitreous. It involves removing the cloudy vitreous and replacing it with a balanced salt solution. Because the vitreous is mostly water, there should be no change in vision when the balanced salt solution replaces the vitreous.

Studies show that people who have a vitrectomy soon after a large hemorrhage are more likely to protect their vision than someone who waits to have the operation. Early vitrectomy is especially effective in people with insulin-dependent diabetes, who may be at greater risk of blindness from a hemorrhage into the eye.

Also provided are compositions and methods of treating or preventing retinopathy of prematurity (ROP) in a subject comprising: identifying a subject having or at risk of having said ROP, and administering to the retina of the subject a polypeptide disclosed herein.

Retinopathy of prematurity (ROP), previously known as retrolental fibroplasia (RLF), is a disease of the eye that affects prematurely born babies. It is thought to be caused by disorganized growth of retinal blood vessels which can result in scarring and retinal detachment. ROP can be mild and may resolve spontaneously, but can lead to blindness in serious cases. As such, all preterm babies are at risk for ROP, and very low birth weight is an additional risk factor. Both oxygen toxicity and relative hypoxia can contribute to the development of ROP.

Normally, maturation of the retina proceeds in utero and at term, the mature infant has fully vascularized retina. However, in preterm infants, the retina is often not fully vascularized. ROP occurs when the development of the retinal vasculature is arrested and then proceeds abnormally. The key disease element is fibrovascular proliferation. This is growth of abnormal new vessels that may regress, but frequently progresses. Associated with the growth of these new vessels is fibrous tissue (scar tissue) that may contract to cause retinal detachment. Multiple factors can determine whether the disease progresses, including overall health, birth weight, the stage of ROP at initial diagnosis, and the presence or absence of "plus disease". Supplemental oxygen exposure, while a risk factor, is not the main risk factor for development of this disease. Restricting supplemental oxygen use does not necessarily reduce the rate of ROP, and may raise the risk of other hypoxia-related systemic complications.

Patients with ROP are at greater risk for strabismus, glaucoma, cataracts and myopia later in life, and should be examined yearly to help prevent and treat these conditions.

Following pupillary dilation using eye drops, the retina is examined using a special lighted instrument (an indirect ophthalmoscope). The peripheral portions of the retina are pushed into view using scleral depression. Examination of the retina of a premature infant is performed to determined how far the retinal blood vessels have grown (the zone), and whether or not the vessels are growing flat along the wall of the eye (the stage). Retinal vascularization is judged to be complete when vessels extend to the ora serrata. The stage of ROP refers to the character of the leading edge of growing retinal blood vessels (at the vascular-avascular border). The stages of ROP disease have been defined by the International Classification of Retinopathy of Prematurity (ICROP).

Retinal examination with scleral depression is generally recommended for patients born before 30-32 weeks gestation, with birthweight 1500 grams or less, or at the discretion of the treating neonatologist. The initial examination is usually performed at 4-6 weeks of life, and then repeated every 1-3 weeks until vascularization is complete (or until disease progression mandates treatment).

In older patients the appearance of the disease is less well described but includes the residua of the ICROP stages as well as secondary retinal responses.

The most difficult aspect of the differential diagnosis can arise from the similarity of two other diseases: Familial Exudative Vitreoretinopathy, which is a genetic disorder that also disrupts the retinal vascularization in full-term infants, and Persistent Fetal Vascular Syndrome, also known as Persistent Hyperplastic Primary Vitreous, that can cause a traction retinal detachment difficult to differentiate but typically unilateral. In some aspects, the disclosed method can be used to treat Familal Exudative Vitreoretinopathy. In some aspects, the disclosed method can be used to treat Persistent Fetal Vascular Syndrome.

ICROP uses a number of parameters to describe the disease. They are location of the disease into zones (1, 2, and 3), the circumferential extent of the disease based on the clock hours (1-12), the severity of the disease (stage 1-5) and the presence or absence of "Plus Disease". Each aspect of the classification has a technical definition.

The zones are centered on the optic nerve. Zone 1 is the posterior zone of the retina, defined as the circle with a radius extending from the optic nerve to double the distance to the macula. Zone 2 is an annulus with the inner border defined by zone 1 and the outer border defined by the radius defined as the distance from the optic nerve to the nasal ora serrata. Zone 3 is the residual temporal crescent of the retina.

The circumferential extent of the disease is described in segments as if the top of the eye were 12 on the face of a clock. For example one might report that there is stage 1 disease for 3 clock hours from 4 to 7 O' clock.

The Stages describe the ophthalmoscopic findings at the junction between the vascularized and avascular retina. Stage 1 is a faint demarcation line. Stage 2 is an elevated ridge. Stage 3 is extraretinal fibrovascular tissue. Stage 4 is sub-total retinal detachment. Stage 5 is total retinal detachment.

In addition, "Plus disease" can be present at any stage. It describes a significant level of vascular dilation and tortuosity observed at the posterior retinal vessels. This reflects the increase of blood flow through the retina.

Stages 1 and 2 do not lead to blindness. However, they can progress to the more severe stages. Threshold disease is defined as disease that has a 50% likelihood of progressing to retinal detachment. Threshold disease is considered to be present when stage 3 ROP is present in either zone 1 or zone II, with at least 5 continuous or 8 total clock hours of disease, and the presence of plus disease. Progression to stage 4 (partial retinal detachment), or to stage 5 (total retinal detachment), can result in substantial or total loss of vision for the infant.

In order to allow timely intervention, a system of monitoring is undertaken for infants at risk of developing ROP. These monitoring protocols differ geographically because the definition of high-risk is not uniform or perfectly defined. In the USA the consensus statement of experts is informed by data derived by clinical trials and published in Pediatrics 2006. They included infants with birthweights under 1500 grams or under 28 weeks gestation in most cases.

Peripheral retinal ablation is the mainstay of ROP treatment. The destruction of the avascular retina is performed with a solid state laser photocoagulation device, as these are easily portable to the operating room or neonatal ICU. Cryotherapy, an earlier technique in which regional retinal destruction was done using a probe to freeze the desired areas, has also been evaluated in multi-center clinical trials as an effective modality for prevention and treatment of ROP. However, cryotherapy is no longer preferred for routine avascular retinal ablation in premature babies, due to the side effects of inflammation and lid swelling. Scleral buckling and/or vitrectomy surgery can be considered for severe ROP (stage 4 and 5) for eyes that progress to retinal detachment. Few centers in the world specialize in this surgery, because of its attendant surgical risks and generally poor outcomes.

Intravitreal injection of bevacizumab (Avastin) has been reported as a supportive measure in aggressive posterior retinopathy of prematurity.

"Vascular permeability" refers to the capacity of small molecules (ions, water, nutrients) or even whole cells (lymphocytes on their way to the site of inflammation) to pass through a blood vessel wall. Blood vessel walls are lined by a single layer of endothelial cells. The gaps between endothelial cells (cell junctions) are strictly regulated depending on the type and physiological state of the tissue.

Diseases and disorders characterized by undesirable vascular permeability include, for example, edema associated with brain tumors, ascites associated with malignancies, Meigs' syndrome, lung inflammation, nephrotic syndrome, pericardial effusion and pleural effusion. Thus, provided are compositions and methods of treating or preventing these or any other disease associated with an increase in vascular permeability or edema. For example, inhibiting edema formation should be beneficial to overall patient outcome in situations such as inflammation, allergic diseases, cancer, cerebral stroke, myocardial infarction, pulmonary and cardiac insufficiency, heart failure, renal failure, trauma, and retinopathies. Furthermore, as edema is a general consequence of tissue hypoxia, it can also be concluded that inhibition of vascular leakage represents a potential approach to the treatment of tissue hypoxia. For example, interruption of blood flow by pathologic conditions (such as thrombus formation) or medical intervention (such as cardioplegia, organ transplantation, and angioplasty) could be treated both acutely and prophylactically using inhibitors of vascular leakage.

Also provided are compositions and methods of treating or preventing ischemia/reperfusion injury following stroke and myocardial infarction in the context of compromised vascular permeability or otherwise. The said composition can be provided in a perfusion fluid for a patient. A deficit in tissue perfusion leads to persistent post-ischemic vasogenic edema, which develops as a result of increased vascular permeability. Tissue perfusion is a measure of oxygenated blood reaching the given tissue due in part to the patency of an artery and the flow of blood in an artery. Tissue vascularization may be disrupted due to blockage, or alternatively, it may result from the loss of blood flow resulting from blood vessel leakage or hemorrhage upstream of the affected site. The deficit in tissue perfusion during acute myocardial infarction, cerebral stroke, surgical revascularization procedures, and other conditions in which tissue vascularization has been disrupted, is a crucial factor in an occluded blood vessel or to repair or replace a damaged blood vessel, the ensuing reperfusion can, in some cases, lead to further damage. Likewise, during bypass surgery, it is necessary to stop the heart from beating and to have the patient hooked to a heart pump. Some patients who undergo bypass surgery, for example, may actually experience a worsening of condition ("post-pump syndrome"), which may be the result of ischemia during cessation of cardiac function during surgery. An arterial blockage may cause a reduction in the flow of blood, but even after the blockage is removed and the artery is opened, if tissue reperfusion fails to occur, further tissue damage may result. For example, disruption of a clot may trigger a chain of events leading to loss of tissue perfusion, rather than a gain of perfusion.

Angiogenesis and angiogenesis related diseases are closely affected by cellular proliferation. As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus lustrum, endometrial and placenta. The term "endothelium" is defined herein as a thin layer of flat cells that lines serous cavities, lymph vessels, and blood vessels. These cells are defined herein as "endothelial cells". The term "endothelial inhibiting activity" means the capability of a molecule to inhibit angiogenesis in general. The inhibition of endothelial cell proliferation also results in an inhibition of angiogenesis.

Both controlled and uncontrolled angiogenesis are thought to proceed in a similar manner. Endothelial cells and parricides, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

New blood vessels may also form in part by vasculogenesis. Vasculogenesis is often distinguished from angiogenesis by the source of the endothelial cells. Vasculogenesis is said to involve the recruitment of endothelial progenitor cells known as angioplasty. These angioplasty can come from the circulation or from the tissue. Vasculogenesis is regulated by similar signaling pathways as angiogenesis. Thus, the term "angiogenesis" is used herein interchangeably with vasculogenesis such that a method of modulating angiogenesis can also modulate vasculogenesis.

Provide herein are compositions and methods of modulating angiogenesis in a tissue, comprising delivering into endothelial cells of the tissue a composition comprising polypeptides disclosed herein. Also provided is a method of modulating angiogenesis in a tissue, comprising delivering into endothelial cells of the tissue a composition comprising a nucleic acid disclosed herein. Also provided is a method of modulating angiogenesis in a tissue, comprising administering to the tissue a composition comprising a vector disclosed herein, wherein the vector transducers an endothelial cell. In some aspects of the disclosed methods, angiogenesis is promoted to increase vascularization. In some aspects of the disclosed methods, angiogenesis is inhibited to reduce vascularization of a tissue.

For example, persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic-dependent, angiogenic-associated, or angiogenic-related diseases. These diseases are a result of abnormal or undesirable cell proliferation, particularly endothelial cell proliferation.

Thus, the methods and compositions described herein are useful for treating human and animal diseases and processes mediated by abnormal or undesirable endothelial cell proliferation, including, but not limited to, hemangioma, solid tumors, leukemia, central retinal vein occlusion, branch vein occlusion, retinal neovascularization secondary to carotid insufficiency, sickle cell retinopathy status post radiation retinitus, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation. The method and composition are particularly useful for treating angiogenesis-related disorders and diseases by inhibiting angiogenesis. Other uses for the disclosed peptides are disclosed in International Patent Publication WO/2006/069181, which is incorporated by reference herein in its entirety for the teaching of these methods.

Provided herein are compositions and methods of promoting wound healing, organ or tissue replacement and tissue regeneration following injury, disease, surgery or congenital malformation in a subject, comprising administering to the subject one or more of the herein provided compositions (e.g., polypeptides, nucleic acids, or vectors or combinations thereof).

It is understood that the disclosed compositions and methods are not limited to the particular methodology, protocols, and reagents described as these can vary. It is also to be understood that the terminology used herein is for the purpose of describing particular embodiments only, and is not intended to limit the scope of the present invention, which will be limited only by the claims.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

"Pharmaceutically acceptable" is meant a material that is not biologically or otherwise undesirable, i.e., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. On the other hand, in certain instances a pharmaceutically acceptable" carrier would be selected to undergo immediate or controlled degradation to release the said composition.

"Promote," "promotion," and "promoting" refer to an increase in an activity, response, condition, disease, or other biological parameter. This can include but is not limited to the initiation of the activity, response, condition, or disease. This can also include, for example, a 10% increase in the activity, response, condition, or disease as compared to the native or control level. Thus, the increase can be a 10, 20, 30, 40, 50, 60, 70, 80, 90, 100%, or any amount of increase in between as compared to native or control levels.

As used herein, "inhibit," "inhibiting," "inhibition" and "loss of function" mean to decrease an activity, response, condition, disease, or other biological parameter. This can include, but is not limited to, the complete loss of activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, agonizing, activating or gain of function mean to increase an activity, response, condition, disease, or other biological parameter. This can also include, for example, a 10% increase in the activity, response, condition, or disease as compared to the native or control level. Thus, the reduction can be a 10, 20, 30, 40, 50, 60, 70, 80, 90, 100%, 200%, 400% or any amount of increase in between as compared to native or control levels.

By "treat" or "treatment" is meant a method of reducing the effects of a disease or condition. Treatment can also refer to a method of reducing the underlying cause of the disease or condition itself rather than just the symptoms. The treatment can be any reduction from native levels and can be but is not limited to the complete ablation of the disease, condition, or the symptoms of the disease or condition. For example, a disclosed method for promoting wound healing is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels.

As used herein, "subject" includes, but is not limited to, animals, plants, bacteria, viruses, parasites and any other organism or entity that has nucleic acid. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The provided method can reduce scar tissue formation in a subject following tissue injury. By "scar tissue" is meant the fibrous (fibrotic) connective tissue that forms at the site of injury or disease in any tissue of the body, caused by the overproduction of disorganized collagen and other connective tissue proteins, which acts to patch the break in the tissue. Scar tissue may replace injured skin and underlying muscle, damaged heart muscle, or diseased areas of internal organs such as the liver. Dense and thick, it is usually paler than the surrounding tissue because it is poorly supplied with blood, and although it structurally replaces destroyed tissue, it cannot perform the functions of the missing tissue. It is composed of collagenous fibers, which will often restrict normal elasticity in the tissue involved. Scar tissue may therefore limit the range of muscle movement or prevent proper circulation of fluids when affecting the lymphatic or circulatory system. Glial scar tissue following injury to the brain or spinal chord is one of the main obstacles to restoration of neural function following damage to the central nervous system. A reduction in scar tissue can be assessed by the population of cell types within the injured site. For example, a reduction in glial scar tissue can be estimated by an increased ratio of neuronal to astrocytic cells. A reduction in scar tissue formation can be measured by a simple measurement of scar width or area of scar tissue (Wilgus et al., 2003). In addition histological assessments can be made about the restoration of structural complexity within healed tissue in comparison to normal tissue. The reduction in scar tissue can be partial or complete, meaning 10, 20, 30, 40, 50, 60, 70, 80, 90, 100% reduction, or any amount of reduction in between as compared to native or control levels.

In addition to reducing fibrotic tissue formation in a subject in following tissue injury, the provided compositions and methods can also be used to treat disorders associated with pathological increases in fibrotic tissue formation in a subject, such as for example, psoriasis, cutaneous and systemic mastocytosis, asthma, eczema, sinusitis, atherosclerosis, rheumatoid arthritis, inflammatory bowel disease, multiple sclerosis, pulmonary fibrosis and cystic fibrosis. A reduction in fibrotic tissue formation in a subject can be measured by clinical judgment of a doctor assessing whether a regain in normal structure and function of a given tissue and/or organ in a subject has resulted following a treatment. As an example, for psoriasis a doctor would assess the subject's skin to determine whether there has been a reduction in patches of raised red skin covered by flaky white buildup. Certain kinds of psoriasis, are characterized by a pimple-ish (pustular psoriasis) or burned (erythrodermic) appearance. In such cases, the doctor would determine whether treatment has resulted in the reduction of these symptoms. The reduction in fibrotic tissue can be partial or complete, meaning 10, 20, 30, 40, 50, 60, 70, 80, 90, 100% reduction, or any amount of reduction in between as compared to native or control levels. In the case of a tissue or organ in which a subject where a doctor judges that a biopsy is clinically available and/or necessary or in an animal model of the human disease, tissue fragments of biopsies would be prepared and tissue histological structure would be assessed by a clinical pathologist and/or trained histopathologist to determine if reduction in fibrosis and restoration of normal tissue structure and function has occurred. The area of fibrosis to normal tissue can also be quantitatively assessed on such histological preparations.

The provided method can improve tissue regeneration following tissue injury in a subject. By "regeneration" is meant the renewal, re-growth, or restoration of a body or a bodily part, tissue, or substance after injury or as a normal bodily process. In contrast to scarring, tissue regeneration involves the restoration of the tissue to its original structural, functional, and physiological condition. This is also referred to herein as tissue "complexity". The restoration can be partial or complete, meaning 10, 20, 30, 40, 50, 60, 70, 80, 90, 100% restoration, or any amount of restoration in between as compared to native or control levels. As an example, in the case of a skin injury, tissue regeneration can involve the restoration of hair follicles, glandular structures, blood vessels, muscle, or fat. In the case of a brain injury, tissue regeneration can involve maintenance or restoration of neurons. As an example in the case of skin an improvement in tissue regeneration can be assessed by measurements of the volume of fibrous scar tissue to normal regenerated skin as a ratio. As another example, counts can be made of discrete regenerating structures such as regenerating skin glands normalized to the volume of the wound area. As another example, counts of the density of cardiomyocytes can be made in the area of heart normally comprised of scar tissue following the healing of a myocardial infarction. Echocardiography can be used to measure the amount of recovery of cardiac function resulting from the regeneration of muscle cell in this scar tissue.

In one aspect, tissue regeneration involves the recruitment and differentiation of stem cells and/or progenitors cells to replace the damaged cells. These stem cells can be generated from the exogenous stem cells comprising the tissue engineered composition or be endogenous prompted by the composition to join, fuse or otherwise combine in the regenerative repair process. As used herein, a "stem cell" is an undifferentiated cell found among differentiated cells in a tissue or organ, or introduced as part of the tissue engineered composition as described elsewhere herein. The primary roles of stem cells in a living organism are to maintain and repair the tissue in which they are found. By stem cell differentiation is meant the process whereby an unspecialized cell (e.g., stem cell) acquires the features of a specialized cell such as a skin, neural, heart, liver, or muscle cell. As an example, in the case of a skin injury, tissue regeneration can involve the differentiation of stem cells present in the epithelium into hair follicles (Alonso and Fuchs, 2003). In the case of a brain injury, tissue regeneration can involve the differentiation of stem cells into neurons. In the case of a cardiac injury, tissue regeneration can involve the differentiation of stem cells into cardiomyocytes of various types (e.g., myocytes, conduction cells and nodal cells). The provided method can enhance stem cell differentiation following tissue injury in a subject. Enhanced stem cell differentiation can be measured by providing a clinically acceptable genetic or other means of marking endogenous or engrafted stem cells and determining the frequency of differentiation and incorporation of marked stem cells into normal tissue structures. The frequency of stem cell contribution to the repair can be partial or complete, meaning 1, 5, 10, 20, 30, 40, 50, 60, 70, 80, 90, 100% contribution, or any amount of contribution in between as compared to native or control levels. As another example, certain structures such as hair follicles are known to be regenerated from endogenous stem cells following tissue injury. As such, counts of marked stem cell derived hair follicles normalized to tissue injury area would serve as a quantitative assessment of enhanced stem cell differentiation. In a further example, marked resident stem cells in skeletal or cardiac muscle will be prompted to the contribute to the repair process. In another example, counts of the density of stem cell derived cardiomyocytes can be made in the area of heart normally comprised of scar tissue following the healing of a myocardial infarction.

In another aspect, tissue regeneration involves the proliferation and further differentiation of pre-existing cells and/or progenitors cells to replace damaged cells. One example of this could be in the formation of a blastema during the regeneration of newt limb. Another example may be the regeneration of new cardiac muscle cells that occurs following injury to the apex of the newborn mouse heart. These cells can be generated from the exogenous cells comprising a tissue engineered composition or be endogenous and prompted by the composition to join, fuse or otherwise combine in the regenerative repair process. The provided method can enhance cellular and tissue repair following tissue injury in a subject. Enhanced repair can be measured by providing a clinically acceptable genetic or other means of marking endogenous or engrafted cells and determining the frequency of proliferation, differentiation and incorporation of marked cells into normal tissue structures. The frequency of contribution to the repair can be partial or complete, meaning 1, 5, 10, 20, 30, 40, 50, 60, 70, 80, 90, 100% contribution, or any amount of contribution in between as compared to native or control levels. Counts of marked cells normalized to tissue injury area would serve as a quantitative assessment of tissue repair.

The provided composition can reduce inflammation in a subject. By "inflammation", "inflammatory response" or "immune response" is meant the reaction of living tissues to injury, infection or irritation characterized by redness, warmth, swelling, pain, and loss of function, produced as the result of increased blood flow and an influx of immune cells and secretions. Inflammation is the body's reaction to invading infectious microorganisms and results in an increase in blood flow to the affected area, the release of chemicals that draw white blood cells, an increased flow of plasma, and the arrival of monocytes (or astrocytes in the case of the brain) to clean up the debris. Anything that stimulates the inflammatory response is said to be inflammatory. Thus, in addition to reducing inflammation in a subject in response to tissue injury, the provided compositions and methods can also be used to treat disorders associated with pathological increases in levels of inflammatory cells, including, for example, asthma, eczema, sinusitis, atherosclerosis, rheumatoid arthritis, inflammatory bowel disease, cutaneous and systemic mastocytosis, psoriasis, and multiple sclerosis. A reduction in inflammation can be measured by a reduction in the density of inflammatory cell types such as, for example, monocytes or astrocytes. A reduction in inflammation can be measured by a reduction in the density of inflammatory cell types such as, for example, neutrophils, macrophages, microglia, mast cells, basophils, and monocytes. A measurement can be measured by reductions in allied cells such myofibroblasts and the like. A reduction in inflammation can be calculated by an in vivo measurement of neutrophil activity (Jones et al., 1994). In addition factors like frequency of mast cell degranulation or measurement of histamine levels or levels of reactive oxygen species can be used as measurements of reduction in inflammation. The level of inflammation can also be indirectly measured by checking for transcription levels of certain genes by qRT-PCR for e.g. genes like, Interferon-alpha, -beta and -gamma, Tumor Necrosis Factor-alpha, Interleukine 1beta, -2, -4, -5, -6, -8, -12, -18, -23, -27, CD4, CD28, CD80, CD86, MHCII, and iNOS. Measurement of pro-inflammatory cytokine levels in the tissues and or bodily fluids of the subject including plasma can measure a reduction in inflammation. It is noteworthy that a mechanism of action may be by inhibition of inflammatory cell migration and/or inhibition of pro-inflammatory chemicals (histamine, reactive oxygen species) and pro-inflammatory cytokines such as Interleukin (IL)-1, IL-6, IL-8 and tumor necrosis factor (TNF). The reduction in inflammation can be partial or complete, meaning 10, 20, 30, 40, 50, 60, 70, 80, 90, 100% reduction, or any amount of reduction in between as compared to native or control levels.

As used herein, tissue injury can result from, for example, a cut, scrape, compression wound, stretch injury, laceration wound, crush wound, bite wound, graze, bullet wound, explosion injury, body piercing, stab wound, surgical wound, surgical intervention, medical intervention, host rejection following cell, tissue or organ grafting, pharmaceutical effect, pharmaceutical side-effect, bed sore, radiation injury, cosmetic skin wound, internal organ injury, disease process (e.g., asthma, cancer), infection, infectious agent, developmental process, maturational process (e.g., acne), genetic abnormality, developmental abnormality, environmental toxin, allergen, scalp injury, facial injury, jaw injury, sex organ injury, joint injury, excretory organ injury, foot injury, finger injury, toe injury, bone injury, eye injury, corneal injury, muscle injury, adipose tissue injury, lung injury, airway injury, hernia, anus injury, piles, ear injury, skin injury, abdominal injury, retinal injury, eye injury, corneal injury, arm injury, leg injury, athletic injury, back injury, birth injury, premature birth injury, toxic bite, sting, tendon injury, ligament injury, heart injury, heart valve injury, vascular system injury, cartilage injury, lymphatic system injury, craniocerebral trauma, dislocation, esophageal perforation, fistula, nail injury, foreign body, fracture, frostbite, hand injury, heat stress disorder, laceration, neck injury, self mutilation, shock, traumatic soft tissue injury, spinal cord injury, spinal injury, sprain, strain, tendon injury, ligament injury, cartilage injury, thoracic injury, tooth injury, trauma, nervous system injury, burn, burn wound, wind burn, sun burn, chemical burn, aging, aneurism, stroke, digestive tract injury, infarct, or ischemic injury.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Use of JM Peptides in Causing a Potent Decrease of Collagen Synthesis by Scar Forming Fibroblasts The present disclosure describes compositions referred to as JM1 (JM juxtamembrane) and JM2 that were found to have a strong inhibitory effect on collagen synthesis, processing and secretion from scar forming cells or fibroblasts (FIGS. 1 and 2).

The synthetic JM peptides used in these experiments were of the amino acid sequence:

```
JM2
                                      (SEQ ID NO: 4)
   rrrr rrrr VFFKGVKDRVKGRSD JM1
                                      (SEQ ID NO: 5)
   rrrr rrrr VFFKGVKDRV
```

The 8 lower case r's represent D isomers of the amino acid arginine and together form a cell penetration sequence. The subsequent 15 (JM2) or 10 (JM1) amino acids (aas) are based on the juxtamembrane sequence of the gap junction protein Cx43. JM1 are based on aas 231 to 241 of Cx43. JM2 are based on aas 231 to 246 of Cx43.

Isolation and treatment of Neonatal Cardiac Fibroblasts with Cx43 based peptides (peptides used included ACT1, JM1, JM2, Antenapedia [ANT], reverse ACT1 [Rev], poly Arginine [poly r]). Neonatal cardiac fibroblasts (NHFs) were isolated from 3-4 day old rat hearts by collagenase digestion (100 U/mL) and differential attachment as previously described (Borg et al., 1984). All cells were maintained in Dulbecco's Modified Eagle Medium (DMEM) supplemented with 10% Fetal Bovine Serum and 100 U/mL penicillin G and 100 µg/mL streptomycin and used prior to passage four. For experiments, 40,000 NHFs were plated into the wells of a 24-well tissue culture plate and grown for 24-48 hours. On the day of treatment, media was removed from each well and replaced with fresh media containing 50 µg/mL L-ascorbic acid-2-phosphate; Sigma Chemical Co., St. Louis, Mo.). The appropriate volume of each peptide (resuspended in sterile, deionized 18 MΩ resistivity water) was added to achieve the desired final concentration (30, 90, 180 µM peptide concentrations were tested). Culture plates were incubated overnight in a 37° C. incubator with 5% CO2.

Protein Isolation and Examination of Collagen Synthesis by Western Blotting. Conditioned culture media was collected from each well and stored at −20° C. for analysis of soluble collagen. Cellular protein, including insoluble collagen and collagen still within the NHFs, were isolated by adding 100-200 µL of cell lysis buffer (0.01 M Tris, pH 7.4, 0.001 M Sodium Orthovanadate, 1% sodium dodecylsulfate [SDS]) to each well and incubating 10 minutes at room temperature. Prior to addition, cell lysis buffer was warmed to facilitate solubilzation of SDS and 100 µL of Halt protease inhibitor (Pierce Biotechnology, Rockford, Ill.) was added per 10 mL buffer to be used. After incubation, the well bottoms were scraped and liquid transferred to a microcentrifuge tube for storage at −20° C. Protein concentrations of cell lysates were determined using a Micro BCA assay (Pierce). SDS-PAGE samples were prepared by combining either 10 µg of cell lysate or 30 µL of conditioned media with XT loading buffer (BioRad, Hercules, Calif.), dithiotheritol and boiled for five minutes. Samples were loaded onto 3-8% Tris-Acetate Criterion XT gels (BioRad, Hercules, Calif.) and proteins separated at 140V. After electrophoresis, proteins were transferred onto 0.45 µm nitrocellulose membranes (BioRad) overnight at room temperature (Transfer buffer: 25 mM Tris, 192 mM Glycine, 20% Methanol, 0.01% SDS). The presence of collagen was determined by probing the membranes with a rabbit anti-mouse collagen type I antibody (MD Biosciences) at 1:20,000 dilution in blocking buffer (5% milk in Tris-buffered saline) followed by a goat anti-rabbit IgG horseradish peroxidase conjugated antibody at 1:100,000 (Southern Biotech Associates) and detection with Pierce SuperSignal Femto West detection reagent (Pierce).

To assess the activity of JM1 and JM2 peptides with respect to collagen production and their potential in mediating wound healing, cardiac fibroblasts were treated with these two peptides and their effectiveness compared to that for the previous described Cx43 peptide ACT1. NHFs were treated with various concentrations of JM1, JM2, ACT1, and ANT (Antenapedia) peptides, vehicle (water) or left untreated and the production of collagen both in the culture media and cell-associated collagen assessed by western blotting. FIG. 1 illustrates that treatment of NHFs with ACT1 resulted in a dose-dependent reduction in the secretion of mature, fully processed collagen where as treatment with ANT, vehicle (lane labeled HC180) or untreated (UT) samples showed high levels of mature collagen type I. Treatment with JM1 and JM2 also yielded a dose-dependent decrease in the production of mature, type I collagen; however, at the highest dose of JM1 and JM2 tested (180 µM), no mature type I collagen was detected in conditioned media. Even at the middle dose of 90 µM, JM1 and JM2 demonstrate more than a than 50% reduction in mature type I collagen produced compared to ACT1. Data from NHF cell lysate samples, shown in FIG. 2, revealed a similar trend in that treatment with JM1 and JM2 had a more profound reduction in the amount of mature type I collagen than treatment with the ACT1 peptide. To evaluate the impact of the poly-Arginine (poly-r) N-terminal sequence on JM1 and Jm2 activity, NHF cells were treated with a poly-r peptide. At equivalent concentrations (~90 µM) the amount of collagen produced by NHFs treated with JM1 and JM2 was less than half of that produced by cells treated with the poly-r peptide indicating that the effects of JM1 and JM2 on collagen production were largely due to the Cx43 sequence and not the presence of the poly-r sequence. These results indicate that JM1 and JM2 can have a more potent wound healing effects than those demonstrated by the ACT1 peptide.

The potency of JM peptides can be gauged by comparison to ACT1 (RQPKIWFPNRRKPWKKRPRPDDLEI) another Cx43 sequence developed by the Gourdie laboratory (see FIGS. 1 and 2). ACT1 has been also shown to promote wound healing, regeneration and tissue repair (Gourdie et al., U.S. Pat. No. 7,786,074). ACT1 incorporates aas 373 to 382 of Cx43 (RPRPDDLEI) and is distinct from JM1 and JM2. In the same assay on cultured fibroblasts ACT1 also reduced collagen processing and secretion, but this reduction was less than that caused by JM1 and JM2 (FIGS. 1 and 2).

Example 2

Use of Peptides in Experiments on Cx43 Expression in Cultured Cells

The first tests of JM1 and JM2 were performed from late March to early May 2008, as detailed in laboratory notebooks. The experiments centered on the basic cell biology of the peptides. To this end, a HeLa cell line stably expressing Cx43 (Cx43-HeLa; a cell line that the Gourdie lab has much experience working with), was used. Initially, cells were treated with 1, 2, 5, or 10 µM of either JM1 or JM2 and observed over a 24 hour period. Cell viability was assessed by acridine orange/ethidum bromide staining. No differences in cell death were observed in any of the treatment groups indicating that JM peptides showed no obvious toxicity. At 24 hours JM2 treated cells were more confluent than control cells indicating increased proliferation and survival in the JM2 treated cells.

Given that the 10 µM concentration of peptide was not toxic to cells, the inventors treated Cx43-HeLa cells with 10 µM JM1 or JM2 for 2, 4, 24, or 48 hours followed by fixation and immunofluorescent labeling of Cx43 and ZO-1. FIG. 3 shows these results at the 24 hour treatment. For both JM1 and JM2, greater cytoplasmic Cx43 was observed, particularly in perinuclear regions. However the most striking effects were on ZO-1 organization. In control cells ZO-1 localized to cell borders, often at sites of small, finger-like projections between the cells. Cytoplasmic ZO-1 was also notable. In JM-treated cells a strong contrast in the ratio of cell border to cytoplasmic ZO-1 was found, with relative levels at cell borders being increased over controls. Thus, in JM1 treated cells, ZO-1 cell border labeling was enhanced. In JM2 treated cells ZO-1 levels had well defined cell-cell interfaces and the monolayer appeared to be more epithelia-like. There was also a noticeable increase in the number of cells per area of field, supporting the earlier observation that JM2 treated cells appeared to proliferate and survive at an increased rate.

Example 3

In Vitro Scratch Injury

The potency of JM peptides can be gauged by comparison to ACT1 another Cx43 sequence developed by the Gourdie laboratory that has been also shown to promote wound healing, regeneration and tissue repair (Gourdie et al., U.S. Pat. No. 7,786,074, which is incorporated herein by reference. In Example 3 the effect of ACT1 treatment is thus described to provide an example of the use and results for JM peptides.

As described in Hunter et al. (2005), myocytes from neonatal rats were grown until forming a near-confluent monolayer on a tissue culture dish according to standard protocols. The cultures were subsequently allowed to culture for a further 5 days culture medium comprising 30 µM ACT1 peptide, 30 µM non-active control peptide (RQPKI-WFPNRRKPWKKIELDDPRPR) or phosphate buffered saline (PBS) containing no peptide or control peptide. The non-active control peptide comprises a polypeptide with a carboxyl terminus in which the peptide sequence has been reversed. The amino terminus of active and control peptides are both biotinylated, enabling detection (i.e., assay) of the peptides in the cell cytoplasm using standard microscopic or biochemical methods based on high affinity streptavidin binding to biotin.

Culture media with added peptides or vehicle control was changed every 24 hours during the experiment. The peptide greatly increased the extent of Cx43 gap junction formation between myocytes relative to the control conditions (Hunter et al. (2005).

The transformed fibroblast line NIH-3T3 cells were grown over 2-3 days until forming a near-confluent monolayer on a tissue culture dish according to standard protocols and the monolayer was then pre-treated with peptide for 24 hrs, and "scratch-injured" with a p200 pipette tip. The "scratch injury" was subsequently allowed to repopulate for 24 hours in the presence of 30 µM active peptide dissolved in the culture media or in presence of two control conditions.

In the first control condition, the "scratch-injured" cells were allowed to repopulate for 24 hours in the presence of a non-active control peptide dissolved in the culture media at a concentration of 30 µM. In the second control condition, phosphate buffered saline (PBS) was added to the culture media and the "scratch-injured" cells were allowed to repopulate in the presence of this vehicle control solution containing no active peptide or control inactive peptide. The "scratch injury" of active peptide-treated cells remained relatively repopulated after 24 hours, with few cells repopulating the area within the initial "scratch injury" edges. The peptide treated cells also can show reduced proliferation of the cells in the experimental cellular model.

Example 4

In Vivo Skin Wound Healing

In Example 4 the effect of ACT1 treatment is described to provide an example of use and results for JM peptides. The results described in Example 4 were published in Ghatnekar et al. (2009) and in Gourdie et al., U.S. Pat. No. 7,786,074, which are incorporated herein by reference.

Neonatal mouse pups were desensitized using hypothermia. A 4 mm long incisional skin injury was made using a scalpel through the entire thickness of the skin (down to the level of the underlying muscle) in the dorsal mid line between the shoulder blades. 30 µl of a solution of 20% pluronic (F-127) gel containing either no (control) or dissolved ACT1 peptide at a concentration of 60 µM was then applied to the incisional injuries. Pluronic gel has mild surfactant properties that may aid in the uniform dispersion of the peptide in micelles. More importantly, 20% pluronic gel stays liquid at temperatures below 15° C., but polymerizes at body temperature (37° C.). This property of pluronic gel probably aided in the controlled release of peptide into the tissue at the site of incisional injury, protecting the peptide from break-down in the protease-rich environment of the wound and also enabling active concentrations of the peptide to be maintained over prolonged periods. Inactive control or active peptide containing gel was applied subsequently 24 hours after the initial application. No further application of peptide containing gel was made after the second application. By 48 hours it can be noted that the treated injury was significantly more closed, less inflamed, less swollen (note ridges at the wound edge), and generally more healed in appearance than the control injury. These differences in inflammation, swelling and healing between the control and treatment and control persisted at the 72 and 96 hour time points. At 7 days, the active peptide treated wound, had a smoother and less scarred appearance than the control peptide-treated injury.

Figures 4K, 4L, 4M:
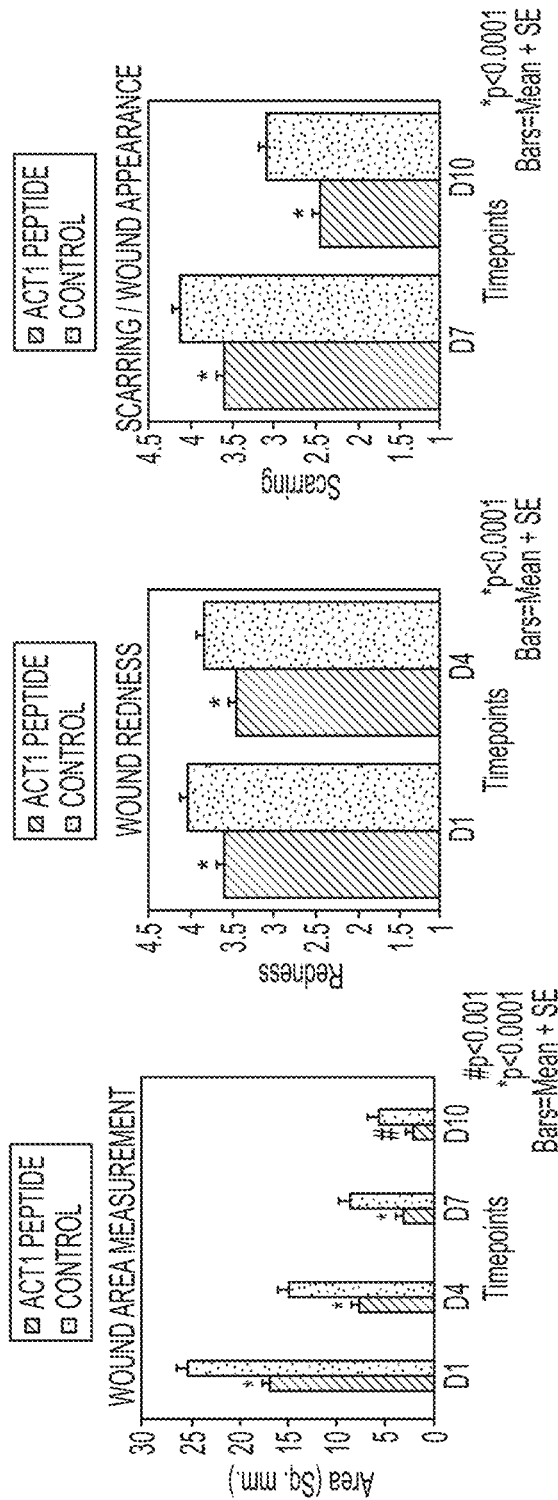

Anesthetized adult mice had 8 mm wide circular excisional skin injuries made by scalpel down to the underlying muscle in the dorsal mid line between the shoulder blades. The boundary of the injury was demarcated by an 8 mm wide circular template cut in a plastic sheet. 100 µl of a solution of 30% pluronic gel containing either no (control) or dissolved ACT1 peptide at a concentration of 100 µM was then applied to the excisional injuries. Peptide containing gel was applied subsequently 24 hours after the initial application. No further applications were made after the second application. The treated excisional injuries closed faster, were less inflamed in appearance, healed faster and scarred less than the control injuries over a 10-14 day time course. Histochemical analyses confirmed that active peptide treated wounds healed with less redness/inflammation and area of scar tissue, as well demonstrating partial regeneration of epidermal and vascular organization (e.g., FIG. 4). The provided composition is thus contemplated to provide a treatment for dermal injuries.

Example 5

In Vivo Healing of Chronic Skin Wounds

Poor healing or chronic wounds such as venous ulcers of the leg, diabetic foot ulcers, or pressure ulcers are a common cause of morbidity, can be recurrent for a given patient and are difficult and expensive treat. There are few if any approved or effective pharmacological treatments of such poor healing wounds. In one example, patients clinically diagnosed by their Doctor as having ulceration of venous origin would be treated with JM peptide. Diagnosis may include measurement of the ratio of ankle to brachial systolic pressure and a determination that this pressure was abnormal (e.g., >0.8). Other aids to diagnosis could include arterial and venous Doppler, venous outflow strain-gauge plethysmography, and photoplethysmography. Treatment of the wound would occur every 1, 2, 3, 4 or 5 days. Prior to treatment the ulcer would be irrigated with a saline solution, JM Peptide at 100 µM dissolved in a 2-10% ethylcellulose gel or other suitable vehicle would then be applied to the wound such that it evenly covered it. The volume of gel applied would depend on ulcer size. The wound would then be covered with a dry gauze dressing and the dressing would be held in place by a toe-to-knee elastic compression bandage. The progression of healing would be monitored by the patients Doctor and the initial healing process would be considered complete when full re-epithelialisation had occurred. The patient would also return to the clinic at subsequent intervals after healing to ensure that recurrence had not occurred. In the case of recurrence, treatment would be repeated until complete healing was observed.

Example 6

In Vivo Wound Healing in Association with a Stem Cell Treatment

In Example 6 the effect of ACT1 treatment is described to provide as an example of use and results for JM peptides. The results described in Example 6 for ACT1 peptide were published in Gourdie and Potts, US Patent application, US20110086068, which is incorporated herein by reference.

Figure 5:
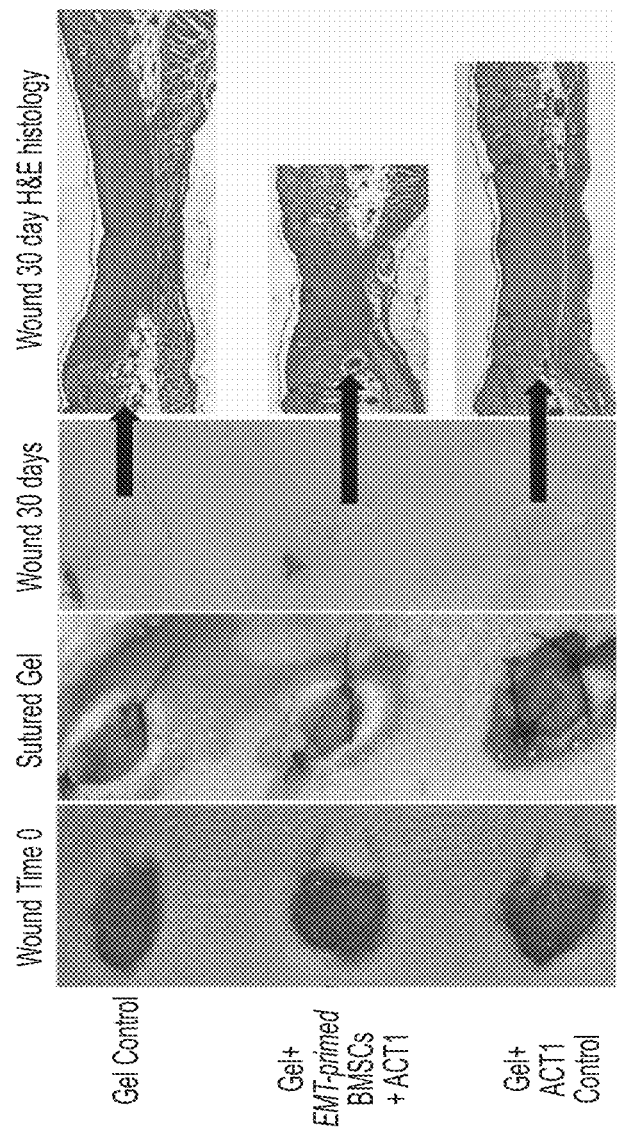
FIG. 5. Bone marrow mesenchymal stem cells enhance regeneration and reduce scar tissue following wounding. RH panel: 8 mm skin wounds on back of rat immediately after wound (Time 0). RH-mid: Gels sutured in at time 0. LH mid: 30 day-old healed wounds. Red=scar boundary. LH: H&E mid-scar plane (arrow). Note dramatically reduced scar (yellow line) of stem cell+peptide treated wound relative to a gel-only control and an ACT1+ve control. Note also epidermal complexity (regeneration index) of wound receiving BMSCs with peptide.
Figure 6A:
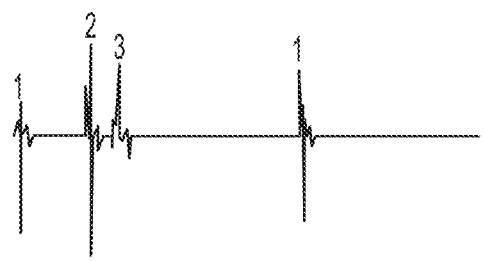
FIGS. 6A-G. Electrophysiological evidence of cardiac arrhythmia reduction following treatment.
Figure 6B:
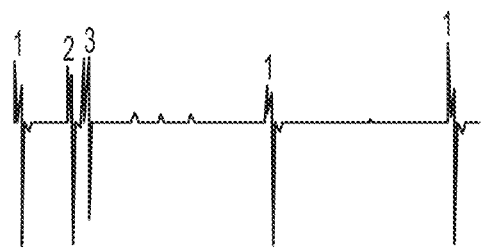
Figure 6C:
Figure 6D:
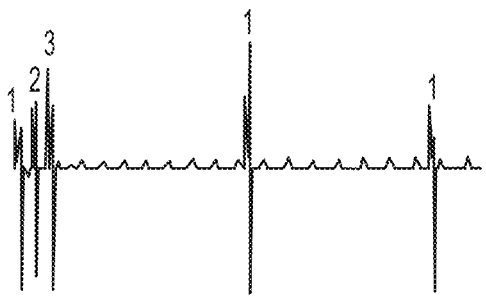
Figure 6E:
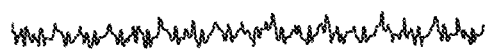
Figure 6F:
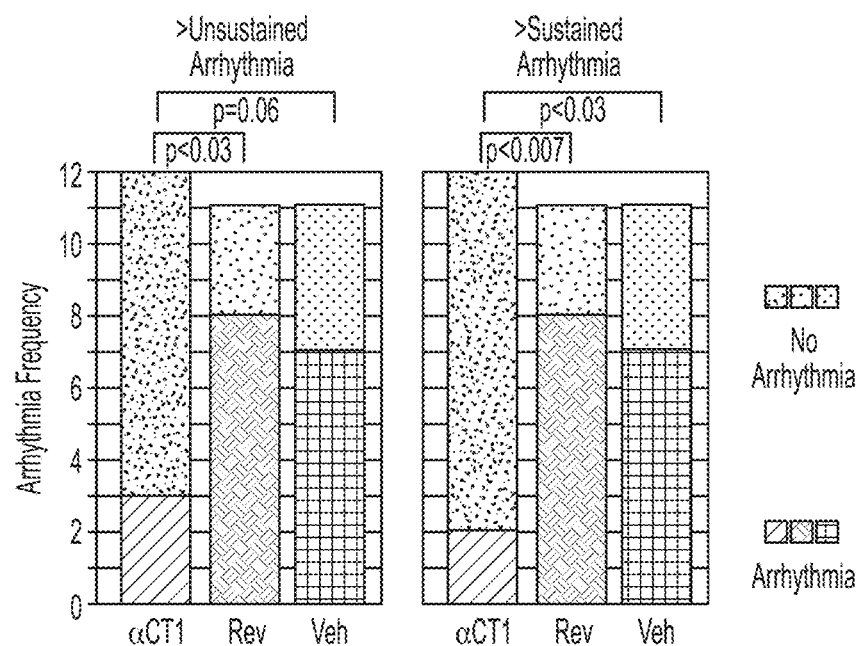
Figure 6G:
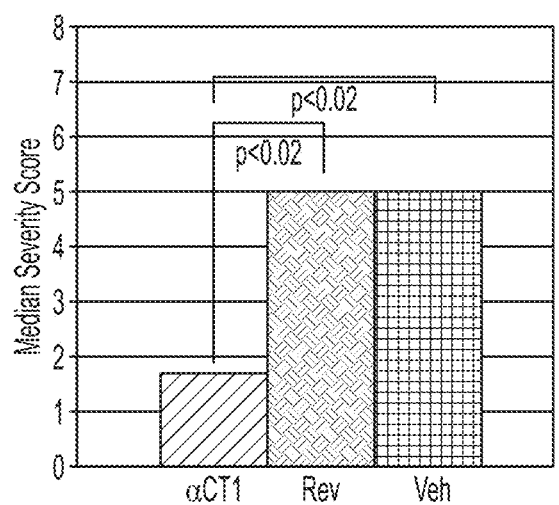

Stem cells were primed using the method described herein prior to engraftment into a wound. Adult bone marrow stromal cells (BMSC—mesenchymal stem cells) were isolated from adult rat femurs and passaged and cultured to produce a pure population of BMSC. A small biopsy punch (8 mm) was used to create a small, 8 mm diameter round wound on the back of the animal (FIG. 5). The punch site was inlayed with the preformed collagen cell containing the BMSC cells (configured in a toroid as per Gourdie and Potts, US20110086068) and/or peptide and two 4-0 prolene stitches were placed in the skin at the biopsy sight to hold the gel in place. The collagen gel (1 mg/ml) was polymerized in a sterile hood and BMSC cells were treated with the ACT1 peptide (150 µM) and then added either on top of the 1.5 mm gel (toroid) or mixed into the polymerizing gel. Wounds were also treated with the gel only, gel plus peptide alone, gel plus cells alone and toroids with an inactive control peptide. Animals were allowed to heal for 30 days and then sacrificed and the pelts were removed and the wounds excised and surrounding skin was processed for standard embedding in paraffin epidermal surface-up (FIG. 5).

From wound edge to wound edge every 30th section was mounted on a glass slide and stained with H&E histochemistry. Images of the granulation in each section were then recorded as single images or montages of 2-3 images. Generally 15-30 serial 300 um-spaced sections were recorded per wound. The granulation tissue area, length of epidermal surface and number of follicles intersecting the epidermis were then counted or measured using Image J software from each wound montage. Estimates of wound granulation tissue volume and the granulation tissue area measurements were recorded for each section. Similarly, scar surface area was estimated as was follicle density in the scar epidermis. T-tests for paired samples were carried using MS Excel (p<0.05). Measurements on treatments wounds within individual rats were normalized to the gel only control wound as a baseline.

The peptide-alone treated wound had a scar area and scar tissue volume that were significantly (p<0.05) smaller than the controls and most other treatments (FIG. 5). However, the wound that received both the BMSC toroid and the peptide had a scar that was even smaller in surface area than the peptide-alone treated wound. This finding of improved healing for the combinatorial treatment over all other treatments/controls was a consistent result. It was also noted that these same 2 wounds, Gel+ACT1 and Gel+BMSC Toroid+ active peptide, showed consistent significantly faster closure rates than the other 4 wounds. Qualitative and quantitative appraisals of the wounds indicated the following pattern of variance in scar size: Gel+BMSC toroid+active peptide< (smaller than) Gel+active peptide<Gel+BMSC Toroid<Gel alone=Gel+BMSCs (non-toroidal)+active peptide wound=Gel+BMSC Toroid+Rev control wound. Importantly, the combinatorial treatment of gels containing the toroid of BMSCs and active peptide consistently had the smallest scars at the end of the 30-day experiment. The provided composition is thus contemplated to provide a treatment of dermal injuries in association with stem cells.

Example 7

In Vivo Cardiac Wound Healing and Arrhythmia Reduction

In Example 7 the effect of ACT1 treatment is described to provide an example of contemplated use and results for JM peptides. The results described in Example 7 were published in O'Quinn et al. (2011); Gourdie et al., U.S. patent application US20100286762; and Norris et al. (2008), which are incorporated herein by reference.

One of the commonest injuries to the heart is a myocardial infarction (MI) that occurs as a sequalae to coronary heart disease (CHD). CHD is the biggest killer of people in developed countries. During an MI or "heart attack" there is a sudden failure of coronary circulation. If the patient survives, the MI scar may cause sickness or death from loss of cardiac function (heart failure) or prompt the development of life-threatening arrhythmias. The provided invention would be deployed to reduce scarring following MI and thus ameliorating morbidity and mortality associated with CHD.

We developed a new method for injuring the heart in an animal model that was specifically designed to increase the ability to determine whether our therapeutic approach causes regeneration rather than the normal process of formation of scar tissue following an injury such as MI. This method involved delivering a freezing injury to the heart that always generated a non-transmural wound of consistent size and depth in the left ventricular wall muscle. Because wound size was consistent between mice, the inventors can be certain of the exact amount of scar tissue that would be deposited in the heart in each animal injured. More importantly, the consistency of the lesion enabled us to determine with certainty that has not been previously achievable by others as whether newly regenerated muscle was present in the healed injury.

To undertake the injury, 12-24 wk female CD1 mice (Charles River) were used. Mice were anesthetized (isoflurane), intubated and a left thoracotomy was performed at the 4th intercostal space. The LV wall was cryo-injured by exposure for 5 sec to a liquid-N2 chilled 3 mm circular flat-tip probe (Brymill: CRY-AC-3) such that the LV surface was slightly depressed. In the case of treatment of the animal model with the composition cryo-injury, the mouse receives EMT-primed BMSCs in gel together with 3 ng/ml of TGF-beta3 over the cryo-injury, and the gel is then held by 2 small dissolving sutures on the surface of the epicardium. Cel-Tak™ adhesive (BD Biosciences) or other surgical adhesive can also be used to secure the gel to the wound. Surgical wounds are then closed using 6-0 silk sutures (Ethicon) and sealed with Nexabond™.

Using the said cardiac-injury model, we have showed (i.e., p<0.05), that release of ACT1 from a methyl-cellulose patch on the injury results in significant improvement in LV diastolic and systolic function over a 8 week time course. This improvement in mechanical function was associated with significantly increased scar uniformity. Treated hearts also showed higher and more uniform, intercalated-disk-localized and pS368 phosphorylated Cx43 in myocytes bordering the scar. Consistent with evidence that downregulated and disordered Cx43 at the infarct border zone is a key factor in cardiac conduction disturbance, we determined that there was a dramatically reduced (p<0.05) frequency and severity of arrhythmias in peptide-treated animals as assessed by electrophysiological studies (pacing and S1-S2 protocols—e.g., FIG. 6).

In another example of the novel injury method, analysis of heart pump function by echocardiography showed that one week following injury in a second group of treatment mice (mice in which bone marrow containing stem cells were infected in vivo with a periostin shRNA lentivirus) and control mice (i.e., mice similarly receiving a control virus) showed a similar (~20%) decline in the efficiency of heart pumping function—as measured by % ejection fraction from the left ventricle. Ejection fraction is a standard clinical measure of cardiac pumping efficiency. This decline indicated that just after freeze wounding both treatment and control hearts had received a similar initial degree of injury as reflected by their similar reduction in function over the first week. However, at the end of the following 4 weeks, a stage that we would expect the healing of the injury to the heart and scar formation to be nearing completion, cardiac pump function of the treatment had improved to be <98% better than that of controls. Remarkably, by 4 weeks heart pump function in the treatment had recovered to levels identical to those of a normal uninjured heart. Meanwhile in controls, pump function had declined at the 4 week period by 50% compared to uninjured hearts.

The improvement in % fractional shortening of the left ventricle is another clinically used measurement of cardiac function and contractility. Percent fractional shortening improved by more than 120% in the treatment relative to control at 4 weeks following injury. As was the case with ejection fraction, treatment caused a recovery of % fractional shortening levels to those of a normal, uninjured heart at 4 weeks, whereas controls continued to show significant declines in this index of cardiac contractile function.

The systolic and diastolic volume of the left ventricle during the cardiac contraction cycle are two other commonly used indices of cardiac function. Increases in these indices are recognized as indicative of a loss of cardiac function and are viewed by clinicians as disease markers for the development of eventual heart dilation, heart failure and death. The diastolic volume of the left ventricle of treatment was significantly improved, being 40% less dilated than that of control. More remarkably, left ventricular systolic dimension was improved to be >75% lower than controls. Putting this another way, at 46.5, the left ventricular volume of control at systole was 5-times more dilated at systole than that of the 10.61 value measured from the echocardiograms of treatment. Treatment also caused both left ventricular volume indices to recover to levels found in the normal, uninjured heart. No such recovery to normality has ever been noted to occur in controls.

The data at 4 weeks post-injury led us to conclude that the mice that had received our standardized cardiac injury and treatment unexpectedly recovered to normal cardiac pump function and contractility. In further contrast to controls, there was no sign of pathological cardiac dilation indicating that treated hearts were progressing to heart failure and eventual death.

Echocardiographic measurements of % ejection fraction, % fractional shortening, and left ventricular volume at diastole and systole were repeated at 6 weeks. These measurements indicated that the improvement in these parameters found at 4 weeks were sustained 6 weeks following treatment and injury. By contrast, none of these cardiac function parameters showed any improvement in the control at 6 weeks and were for most part were similar to the depressed measurements taken in controls at 4 weeks. Indeed, left ventricular volume at diastole showed further significant deterioration in the control indicating a continuing progression toward heart failure in the untreated control.

Second, the unexpectedly large beneficial effects on regeneration of cardiac muscle and reduction of scar in the injured heart were noted. Following echocardiography at 6 weeks, hearts were removed for morphological and histological analyses. A large pale scar was evident on control hearts with no sign of regeneration. This large scar extended nearly to fully incorporate the boundaries of the initial injury. By contrast, the area of initial injury in a treated heart showed only a minimal amount of visible scar at the 6 week time point. In quantitative terms, less than 10% of the initially injured area on the control heart is cardiac muscle. By contrast, the treated heart showed a 70-90% regeneration of normal cardiac muscle. Thus, in summary our unexpected ability to prompt a full recovery of function in treated hearts is correlated with an equally impressive and unexpectedly extensive regeneration of normal cardiac muscle at the injury.

That regenerated muscle was present was further confirmed by histology of the hearts. Myocytes in treated hearts were found throughout the scar with a particular concentration of these cells near the epicardial border of the scar. This sub-epicardial population was notable for a number reasons. First, it is direct evidence for myocardial regeneration. The freeze injury is via a liquid nitrogen-cooled probe applied to the outer surface of the heart generating a hemi-spherical injury volume. During the freeze injury, the broadest sector of lethally frozen tissue is at the epicardium just under the freezing probe, i.e., the site where we see the "new myocytes" after 4 weeks of healing. Thus, this zone of sub-epicardial "new myocytes" must have regenerated over old necrotic tissue frozen near the epicardium—the previous cells at this location could not have survived the freeze injury. Indeed, in more than 20 control hearts subject to our standardized freeze injury evidence of regeneration at the sub-epicardium was never seen.

The myocytes in this sub-epicardial zone were compact and highly aligned. This means that our treatment method had not only induced "new myocytes", it had also the regenerated the precise tissue organization that existed at this locale in the heart prior to injury. Thus our treatment had unexpectedly regenerated structure at both cellular and tissue scales—i.e., in addition to restoring function at the organ level. Thirdly, we note that these "new myocytes" are contiguous with adjacent myocardium. Cx43 immunolabeling indicates that these new myocytes also express the gap junction protein. Such tissue organization is consistent with electromechanical integration with surrounding myocardial tissues and the lowering the likelihood of arrhythmia. As noted previously, we contemplate that our novel composition will prevent arrhythmias.

It can also be noted that the collagen staining appears significantly paler in the treated hearts indicating that collagen organization is different from that of controls. Whereas much cardiac research is focused on attempting to promote adult myocyte cell cycle re-entry to regenerate cardiac muscle, our novel approach leads to modification of scar organization in vivo. We posit that the scar in the treated animals is a "better scar", permitting a new type of remodeling of this region with new myocytes. Finally, the section reveals that the extent of scar tissue as indicated by comparing the area of scar tissue is significantly less (>60-70% less) in the treatment compared to controls. This means that our treatment has an unexpectedly profound effect of tipping the balance between scar formation, organization and inducing a multiscalar regeneration of functional myocardium in the injured heart.

In a further example in heart, the provided composition can be introduced via keyhole surgery in a human subject who has suffered an MI (i.e., preferably within 1 week of the MI) under full anesthetic by a surgeon into the minimally disrupted pericardial sac of the subject via a catheter. In another example, the composition would be sutured or secured by sterile surgical adhesive into place over an acutely healing MI while the subject's heart is exposed during coronary artery bypass graft surgery (CABG) and the like. Following CABG surgery the healing of the myocardium of the subject would be monitored for improvement in cardiac function by routine EKG, ambulatory EKG, echocardiography, blood assays and other tests of cardiac well being and healing that a qualified clinician deemed necessary for the recovery of the subject. The provided composition can thus provide a treatment for injury to the heart and cardiovascular system.

Example 8

In Vivo Brain and Spinal (CNS) Wound Healing

In Example 8 the effect of ACT1 treatment is described to provide an example of contemplated use and results for JM peptides. The results described in Example 8 were published in Gourdie et al., U.S. Pat. No. 7,786,074, which is incorporated herein by reference.

In one example, anesthetized adult rats were positioned in a stereotaxic apparatus. A midline incision was made on the scalp to expose the skull. A stereotaxic drill was sighted 2 mm posterior to the bregma and 2 holes were drilled with a 1 mm spherical bit, each at 2.5 mm to the right and left of the bregma, and 3.5 mm below the dura. A cerebral lesion was made by inserting an 18-gauge needle. The coordinates were determined from the atlas by Paxinos and Watson (1986). The hollow fiber membrane (HFM) was inserted in the hole and external skin sutures were placed to cover the stab. The ACT peptide was dissolved at 100 µM concentration in a 2% collagen vehicle solution contained within the HFM. Studies of isolated HFMs indicated that these bioengineered constructs were capable of slow release of detectable levels of peptide (as assayed by biotin-streptavidin reaction) in aqueous solutions for periods of at least 7 days. Reactive astrocytosis associated with inflammation and subsequently with glial scar formation follows a well-characterized time course after brain injury in rodent models (Norenberg, 1994; Fawcett and Asher, 1999). Typically, the astrocytic response in rat brain peaks after a week, together with loss of neurons and other aspects of brain tissue complexity. Subsequently with the emergence of glial scar tissue, the density of GFAP-positive astrocytes decreases.

In the control tissue, a high density of immunolabeled GFAP-positive astrocytes was observed near the site of injury caused by the HFM. The density of these cells appeared to diminish slightly distal from the injury. By contrast, a much lower density of GFAP-positive astrocytes was observed adjacent the HFM filled with peptide. Indeed, the levels of GFAP positive cells were not dissimilar to those seen in normal uninjured brain tissue. In the brain injury treated by active peptide, it was seen that GFAP-positive astrocytes were not only less numerous, but are also smaller than those seen in the control injury.

In the control tissue, a high density of immunolabeled GFAP-positive astrocytes and low density of NeuN immunolabeled neurons were observed near the site of injury caused by the HFM. The density of these cells appeared to diminish and increase distal from the HFM, respectively. By contrast, a much lower density of GFAP-positive astrocytes and higher numbers NeuN immunolabeled neurons was observed proximal (as well as distal) to the HFM filled with peptide. These results indicate that the high density of neurons associated with treatment can be from generation of new neurons. The peptide can also increase neuronal density in part by sparing neurons from cell death following brain injury.

Subjects with acute spinal cord injuries to the central nervous system (CNS) represent a seriously problematic group for whom even a small neurological recovery of function can have a major influence on their subsequent independence. The provided composition can thus be useful in patients with a complete cord injury who normally have a very low chance of recovery. For optimal recovery of function the composition would optimally be applied acutely or sub-acutely within 1 week of the initial injury. The prognosis of incomplete cord syndromes would also be improved by the composition.

In a related example, spinal cord experiments were carried out on adult SD rats as previously described by Banik and co-workers (Sribnick et al., 2006). Rats are anesthetized and laminectomies are performed at T-12. Trauma is administered by dropping a weight of 5 g from a height of 8 cm onto an impounder (0.3 cm in diameter; 40 g·cm force) gently placed on the spinal cord. 30 µM peptide and control treatments (as per eye and heart injury) were immediately applied and wounds sutured closed. Spinal cord edema is assessed at 48 hrs post-injury, as described above. Cell death caused by compression injury was also assessed acutely on 5 µm sections of spinal cord from the lesion, which are co-labeled with NeuN and TUNEL staining as a marker for neurons and cell death respectively. Assessment of inflammatory cell infiltration (e.g., microglia and macrophages) was done using OX42 and ED2 antibodies. To determine the long-term benefits of treatment of treatment the functional and behavioral recovery of rats were tracked over time courses up 6 months following injury and NeuN and GFAP immunohistology will be used to assess glial scar and neurogenesis across the scar as described above for the brain injury. The provided composition can thus provide a treatment for injury to the brain.

In another contemplated example, a subject with an acute anterior cord injury due to a flexion injury of the cervical spine would have surgery performed to expose the dorsal aspect of spinal cord at the level of the injury. A gel containing the composition described herein would then be placed directly on the injury. This gel may also contain neurogenic stem cells co-delivered with the provided composition to promote regenerative healing of the spinal cord. Single or multiple compositions are applied depending on severity of the injury. The surgical wound exposing the spinal cord injury is then sutured shut, enclosing the composition in situ. Improvement in function is assessed by a doctor at intervals (e.g., 6, 12, 26 and 52 weeks) following treatment by neurological outcome tests including assessments designed to measure motor activity, pinprick skin sensitivity and recovery of sensation. CT/MRI of the spine at the level of injury is also undertaken to monitor the healing progression of the subject. Medium- and long-term management would then be directed towards rehabilitation, including physiotherapy and occupational therapy to enable as full recovery of function as is possible following the treatment. The provided composition can thus provide a treatment for injury to the spinal chord.

In one aspect the recovery of spinal function will occur because of regeneration of new spinal cord neural connections from stem cells. This reparative aspect will occur in other CNS and PNS (peripheral nervous system) tissues. In another aspect, the recovery of spinal cord function will be contributed to by reduction in inflammation, swelling, odema and tissue loss associated with placement of the composition. Assay of this can be tested in animal models. For example, following injury to rat spinal cord in vivo, rats are treated with the composition. Soluble fluorescein-isothionate-tagged BSA (bovine serum albumin) or Evans blue dye is then injected into the tail vein. Control animals show leakage of the dye from the vascular system into tissues within and surrounding the spinal cord. However, animals treated with the composition demonstrate only limited dye leakage, with it majorly being confined with intact vascular structures. In the case of the CNS tissues such as the brain and spinal cord, this is due to the composition promoting the maintenance of the blood-brain barrier. However, the maintenance of barrier function should in some aspect be seen in all tissues of the body. The results indicate that leakage of the capillary-vascular system is not restricted to the CNS (e.g., spinal cord, brain, retina) and that a broader range of medical applications, such as for treatment of conditions of blood vessels, would benefit from treatment with the provided composition.

Example 9

In Vivo Treatments of the Eye

In Example 9 the effect of ACT1 treatment is described to provide an example of use and results for JM peptides. The results described in Example 9 were published in Rohrer and Gourdie, alpha-Connexin c-terminal (act) peptides for treating age-related macular degeneration, PCT/US2008/067944, Jun. 23, 2008 and Gourdie and Potts, US20110086068, which are incorporated herein by reference.

Normal eyesight is dependent on the transparency and regular curvature of the cornea. The histoarchitecture of the cornea is similar to that of skin-consisting of a stratified epithelium overlying a collagen-rich stromal matrix embedded with fibroblastic cells (e.g., keratocytes), although is largely avascular except at the periphery. Severe injury, surgery (Corneal refractive surgeries (CRS) such as photorefractive keratectomy (PRK)) and certain disease processes can lead to the loss of corneal transparency via activation of fibrotic/scarring processes in the corneal stroma. The resultant severe fibrosis of the cornea is difficult to treat and typically requires corneal transplant, which may lead to further complications. A safe and effective approach to reducing corneal scarring complication such as provided by our composition would thus be welcomed by opthalmologists and eye surgeons alike.

Minor scratches on the cornea are common and the composition is not envisaged to be used for normally healing minor injuries. However, the composition would be of use in the treatment of more serious injuries to the cornea that may occur from small flying particles when drilling, sawing, chiseling, grinding, lawn mowing, and so on without eye protection and also from chemical burns such as that resulting form caustic solutions, acids, wet concrete and the like. Also the composition would be used in patients receiving CRS/PRK surgeries that may present high risk profiles such as those displaying wide pupils or evidence of poor wound healing such as might occur in a diabetic patient.

Following standard sub-acute stabilization and cleansing by a clinician, a subject suffering a severe chemical burn would have a collagen gel containing 180 µM JM peptide prepared, placed directly on the injury. Preferably the treatment would be undertaken within 1 week of the initial injury. Single or multiple compositions can be applied depending on severity of the injury. Antibiotic eye drops would then be placed in the eye to prevent infection. The composition can also be placed in association membrane to further aid healing. The eyelid would then be temporarily sutured closed, to retain the composition and a bandage would then be placed over the closed eye. Painkillers such as paracetamol or ibuprofen would be used to ease pain over the subsequent healing process. 7-14 days later the lids would be released and repair of the cornea assessed by an opthalmologist for inflammation, scarring and other clinical indications of corneal healing. Improvement in function is assessed by a doctor at intervals (e.g., 6, 12, 26 and 52 weeks) following treatment by vision tests. An eye patch to cover the eye would not normally be advised after 10-14 days following injury as this may impair the healing process.

We have already published an animal model of corneal injury (Chen et al., 2009). In this model, adult (12 wk) SD rats were anesthetized and the central cornea treated with 20% ethanol for 30 seconds using a 3-mm marker placed on the corneal surface. The cornea is then thoroughly rinsed with saline and the loosened epithelial layer removed using a detaching spatula. A treatment (i.e., PBS containing ACT1 peptide) or control gel was then placed in the alcohol burn injury and the eye-lid sutured shut for 48 hours to hold the gel in place.

Figure 7:
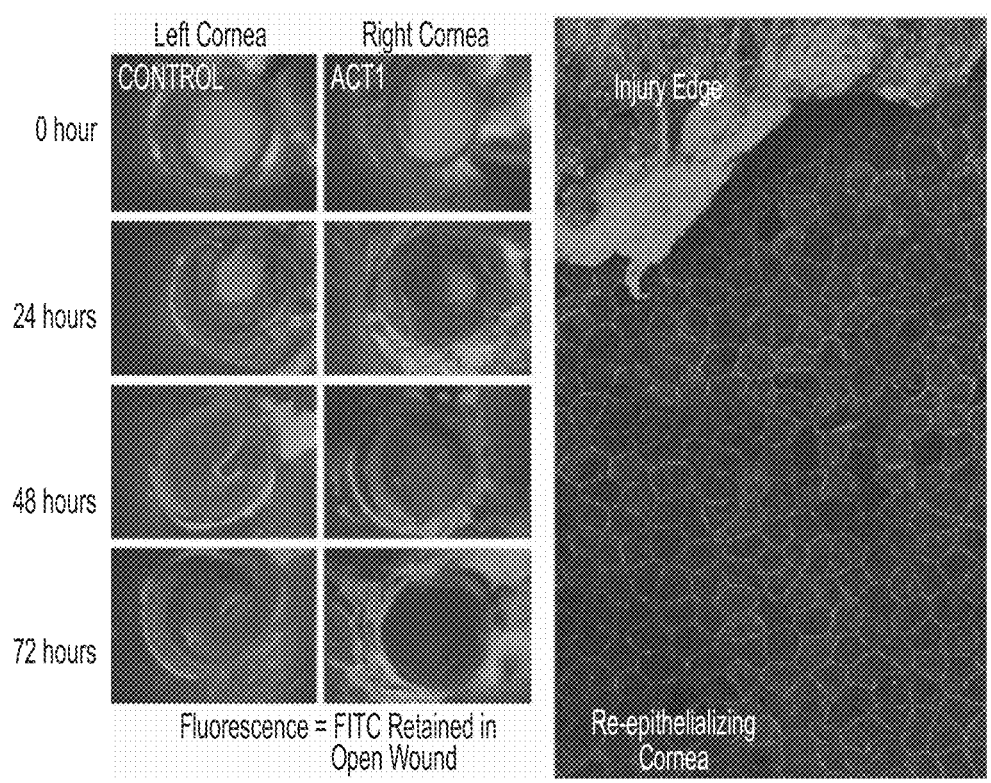
FIG. 7. Wound closure following corneal epithelial removal. Rat corneas were treated with alcohol and the epithelium removed as described above. Flourescein drops were added do demonstrate the removal of the epithelium. If there is no tight epithelial barrier the flourescein binds to the underlying stroma. By 24 hrs the ACT1 treated corneas are re-epithelializing much faster than control corneas. By 72 hrs, the ACT1 treated corneas displayed a significantly greater re-epithelialization. (Right) A confocal image of the re-epithelializing corneas stained with ZO-1 and Connexin 43 to demonstrate the junctional integrity of the new epithelium. The injury edge is shown to give reference to where the re-epithelializing begins.

Corneal wound closure was determined by administering 0.25% fluorescein sodium eye drops and digitally capturing the cornea under a fluorescent stereomicroscope at 0, 48, 72, 96, and 120 (closure is usually complete by 120 hours in rat) hours post-injury. Levels of scar tissue deposition and transparency were assessed on whole mounts of isolated corneas days post injury. Corneal tissue was subject to standard histological and immunohistochemical studies on tissues sections to assess corneal epithelial and endothelial integrity and collagen organization and myofibroblast (alpha-SMA) density in the stroma. Corneas treated with active peptide showed faster closure and more complete corneal regeneration than control corneas (FIG. 7). The provided composition is thus contemplated to provide a treatment for injury to the cornea of the eye.

Figure 8:
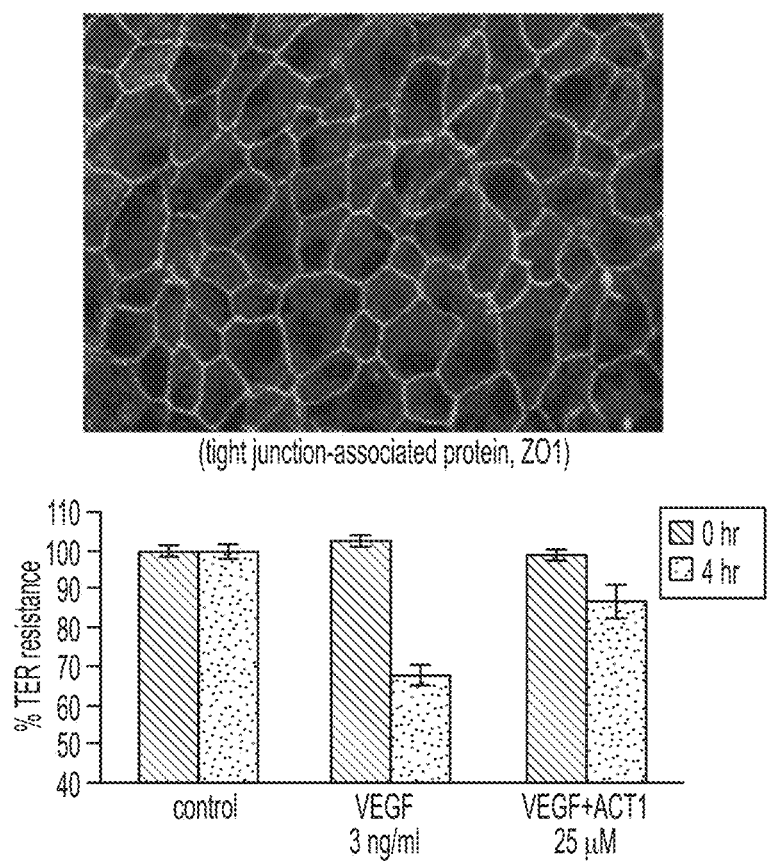
FIG. 8. ACT1 ameliorates VEGF-dependent reduction in transepithelial resistence (TER). (Top) RPE monolayer stained with ZO1. (Bottom) VEGF significantly ($p<0.05$) reduces TER by 4 hours post-application. Pre-treatment with ACT1 ameliorated the drop in TER.

Trans-epithelial resistance (TER) measurements, using ARPE19 cell (immortalized human RPE cells) mono layers has revealed that VEGF leads to rapid deterioration, which was blocked by pre-treating the cells with the ACT1 peptide US2008067944 (FIG. 8). Thus, this peptide can prevent damage to RPE/Bruch's membrane. The Peptide contains a NT cell internalization sequence (CIS). Together with a mild detergent that is used in ocular applications, Brij-78, the CIS assists in permeation of peptide into interior fluids and tissues of the eye. In some aspects, thus JM peptides can enter the internal fluids and tissues of eye and this is a mode of action of CIS containing peptides in treating diseases of the eye such as macular degeneration. The provided composition can thus provide a treatment for promoting stabilization of RPE cells and tissues to permeation in response to VEGF increase.

Application of peptide in a solution containing 0.05% Brij-78 to the cornea of mouse eyes resulted in a detectable level of ACT1 in the internal fluids of the anterior chamber (i.e., the aqueous humor) 20 and 40 minutes post application. Lower levels of peptide could also be detected by Western blotting in fluid from the posterior chamber of eye 20 and 40 minutes, i.e., the vitreous humor. Following application of peptide in a solution containing 0.05% Brij-78 to the cornea of mouse eyes, peptide was detectable in the retinal pigment epithelial layer of eye minutes post-application. Moreover, peptide was immunohistochemically detected in the retinal pigment epithelial layer of eyes exposed to the peptide, but not to the vehicle control solution via corneal application.

Three CD1 mice were anesthetized by IP injection of ketamine per standard protocol. ACT1 peptide (final conc 100 uM) was dissolved in a solution containing normal saline and 0.05% Brij-78 was gently dripped onto the corneal surface of both eyes and allowed to permeate for 20 or 40 min. 0.05% Brij-78 in saline was used on a control mouse. The mice were sacrificed in a CO2 chamber and cervically dislocated at 20, 40 min (the control mouse sacrificed at 20 min). The eyes were removed and rinsed in PBS. A small incision was made in the anterior chamber and the aqueous humor (~10 flL) was transferred to tube and flash frozen in a dry ice ethanol bath. The total sample was dissolved in 2× samples loading buffer and loaded on a 10-20% Tris-Tricine gel. Gel was transferred to a PDVF membrane and stained using RBT Sigma antiCX43 CT antibody (1:10000) and a goat anti-RBT AP secondary (1:15000) to reveal the ACT1 band at <10 kDa. Application of peptide to the cornea in Brij-78 was the same as described above. After sacrifice the mouse eyes were removed, washed in PBS briefly, and transferred to 5% paraformaldehyde overnight. The eyes were embedded in paraffin, sectioned, and stained with Sigma Rbt anti-Cx43, streptavidin and Hoeschst stain and placed at 4 degrees overnight. Peptide is detectable in the interior fluids and tissues of the eye following a simple corneal exposure.

Electroretinography (ERG) to assess level of CNV damage can be recorded using similar protocols to those published by Gresh et al. (2003) (See also FIG. 10). Mice are dark-adapted overnight, anesthetized and pupils dilated. Body temperature is stabilized at 37° C. (DC-powered heating pad). A ground-electrode is placed in the tail, a reference-electrode in the forehead. ERG responses are measured using contact lenses with a gold-ring electrode held in place by methylcellulose. ERGs are recorded (EPIC-2000, LKC Technologies), using a Grass strobe-flash stimulus (gain of 2 k, notch filter set at 60 Hz). Responses are band-pass filtered (0.1-1500 Hz) and digitized (1 kHz, 12 bit accuracy). Stimuli to isolate rods consist of 10 µsec single-flashes at a fixed intensity (2.48 photopic cd-s/m2) under scotopic conditions. Single-flash responses are averaged 2-4× with an inter-stimulus interval of 120 sec. Cone responses can then be recorded under light-adapted conditions, using stroboscopic illumination (1-30 Hz) for stimulation. A-wave amplitude is measured from baseline to the a-wave trough; b-wave amplitude from the a-wave trough or baseline to the peak of the b-wave, and implicit time from onset of stimulus to a-wave trough or b-wave peak.

Figure 9:
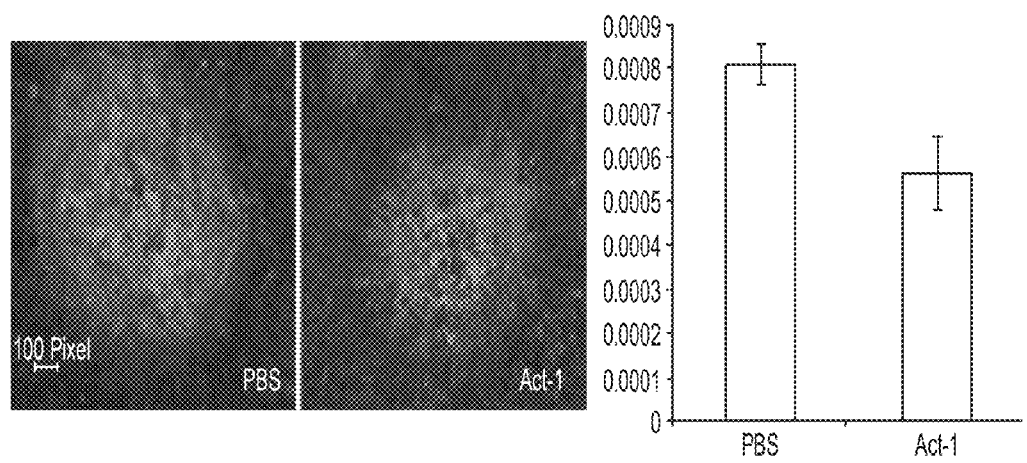
FIG. 9. ACT1 reduces choroidal neovascularization (CNV) progression. (Left) RPE/choroid flat-mount from a laser-treated 3-month-old C57BL/6 mouse treated with PBS or ACT1, stained with isolectin-B4. (Right) The increase in the size of the lesion as determined by confocal microscopy was significantly reduced.
Figure 10:
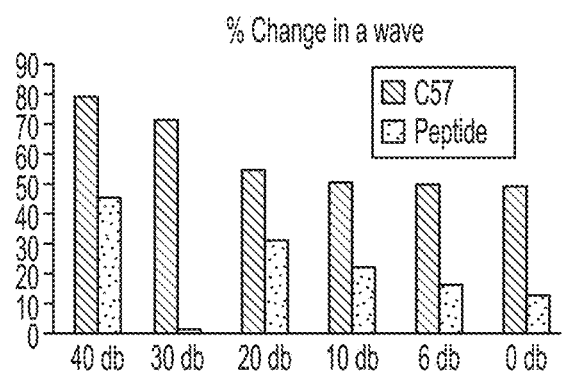
FIG. 10. Functional evidence that ACT1 reduces choroidal neovascularization (CNV) progression. CNV lesions result in a drop in electro-retinal gram amplitudes as can be seen in laser induced CNV in 3-month-old C57BL/6 mice treated with PBS (bars on left) or ACT1 (bars on right). The % change in a-wave amplitude (upper chart) is measured as function of the change baseline to the a-wave trough; the % change in b-wave amplitude (lower chart) is measured as a function of the change from the a-wave trough or baseline to the peak of b-wave, and with timing implicit from onset of stimulus to a-wave trough or b-wave peak.
Figure 10:
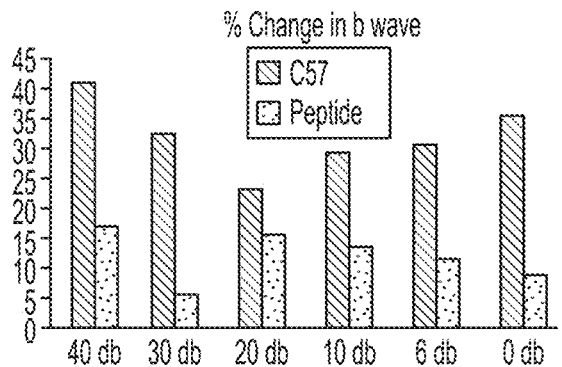
Figure 11:
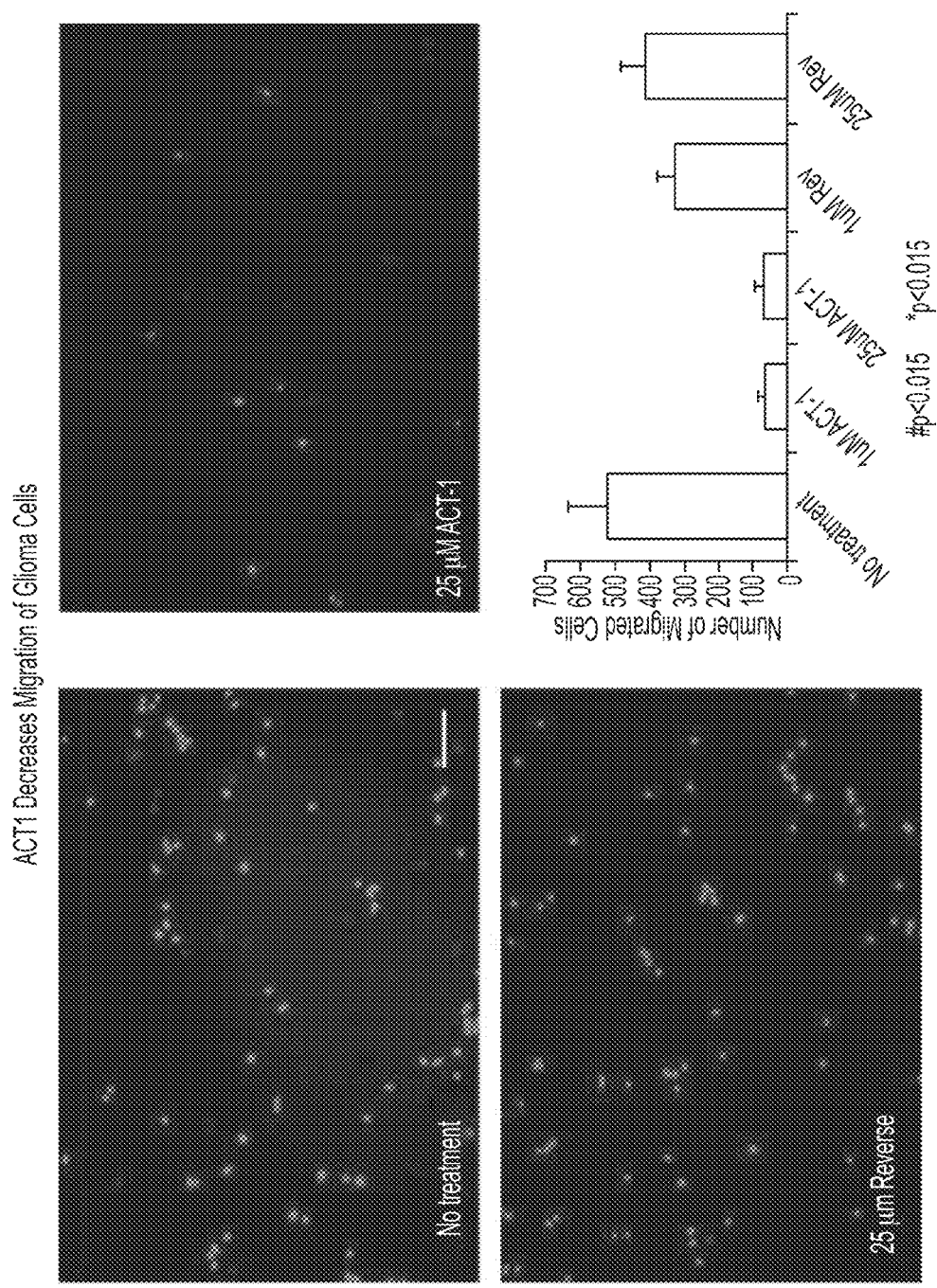
FIG. 11. Reduction in glioma cell metastatic behavior. Boyden chamber migration assays showed that ACT-1 significantly decreased both U87 MG ($p<0.003$) and C6 ($p<0.015$) motility across a porous membrane (Bonferroni t-test). These results provide insights into the role of the Cx43 C-terminus in the malignant behavior of glioma cells. Small molecules such as the peptide that target gap junction organization and promote wound healing may also modulate invasiveness or metastasis of malignant cells.
Figure 12A:
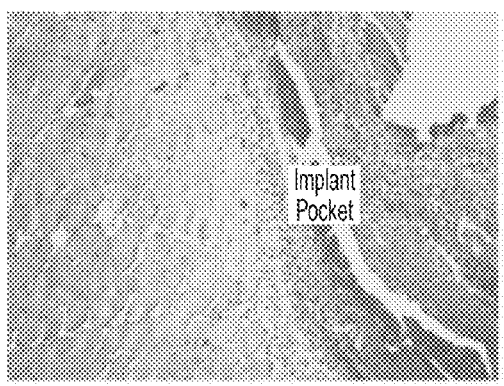
FIGS. 12A-D. JM peptide decreases inflammation associated with silicon implants.
Figure 12C:
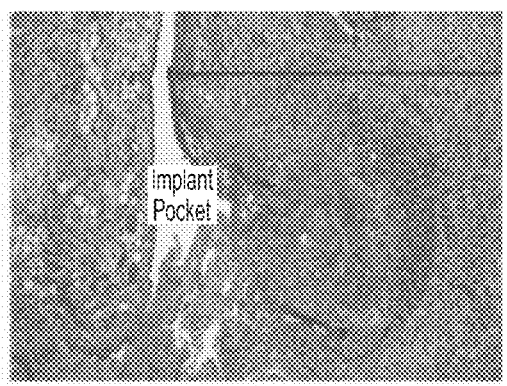
Figure 12B:
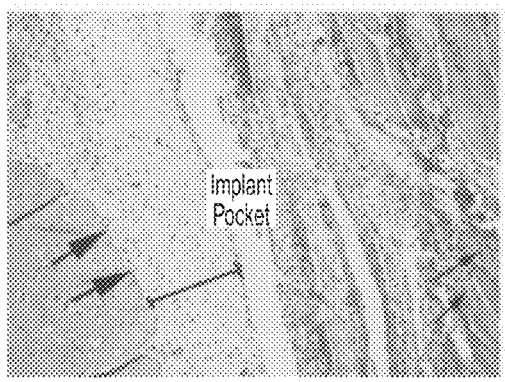
Figure 12D:
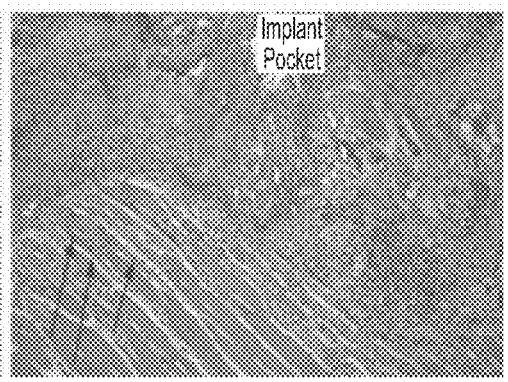

As shown in FIGS. 9 to 11, and in the NIH challenge grant appended to this application (*Treatment of Age Related Macular Degeneration and Diabetic Eye Diseases and Disorders*), in studies in vivo we have shown that: 1) ACT1 can be formulated to permeate into the chambers of the eye following corneal application (i.e., intravitreal injection not required); and 2) in a laser-induced choroidal neovascularization (CNV) mouse model of retinal macular degeneration, peptide treatment reduced CNV injury spread and improved retinal function (as measured by electro-retinal gram (ERG), relative to controls. These results parallel our published data that the peptide reduces inflammation, time to heal and scar tissue formation following dermal wounding. The provided composition is thus contemplated to provide a treatment for macular degeneration.

Example 10

Uses in Tissue Engineering

Results described in Example 10 were published in part in Gourdie and Potts, US20110086068, which is incorporated herein by reference and Soder et al. (2009), which are incorporated herein by reference.

Loss of skeletal muscle mass is an important problem for surgeons. Skeletal muscle has some ability to regenerate from endogenous stem cells called satellite cells. However, if the injury is large, this natural reparative ability can be overwhelmed. In such cases, muscle is not regenerated and scar tissue replaces lost muscle—if the patient is fortunate.

One clinically important example of injuries involving muscle that can be difficult to repair are ventral hernias (also known as incisional hernias). Annually, over 2 million abdominal operations are performed in the United States. (Millikan, 2003). Given a failure rate for abdominal closures of 11 to 20 percent, it is not surprising that over 100,000 ventral hernia repairs are attempted each year in the United States alone. The incidence of ventral hernias has remained relatively stable over the last 75 years despite many medical advances.

The repair of ventral hernias typically involves the closing the hernia with a synthetic mesh or more recently decellularized human dermis (Alloderm, LifeCell). Although these methods effectively "patch the hole" they lack the ability to reconstitute the lost abdominal muscle. The mesh imparts no contractile function and with large hernias it is ineffective at producing counter pressure from the contracture of remaining abdominal musculature. These repair techniques do little to reestablish the dynamic role of the abdominal wall in support of the torso and lumbar spine. With dynamic repairs, force vector summation of abdominal wall contraction is focused on the repair itself. Mesh repairs are also associated with bowel obstruction (5%), enterocutaneous fistulae (2-5%), and infection (1-2%). The aggregate incidence of long term complications associated with mesh repair approaches 27% (Mudge and Hughes, 1985). In the following example we outline how our invention can be used to repair an experimental ventral hernia in a rat—by extension in a human subject.

To create the ventral hernia model, 250 gram male Sprague Dawley rats are used. This size male rat has sufficient tissue for isolation of satellite cells, creation of the abdominal defect and has matured sufficiently to be considered adult in phenotype. After general anesthesia is achieved, the animal is prepped in standard surgical manner. A 1 cm×1 cm excisional wound is then generated in the abdominal muscle through to the cavity of the abdomen. To isolate autologous satellite cells from skeletal muscle of the same rat, a muscle biopsy (0.5 mm×0.5 mm×0.2 mm=0.05 cm$^3$) is extracted from the vastus lateralis and placed in mosconas on ice. This provides the 10 to 1 expansion of cells required to repair the defect. The biopsy wound is approximated and closed by suture. The sampled muscle tissue is rinsed vigorously with PBS at least three times to remove blood. The tissue is then minced thoroughly with scissors to dislodge adherent fat and washed several times with cold PBS. Warmed and gassed protease is added (sigma #P-5147; 1.25 mg/ml in Krebs Ringer Bicarb. Buffer (Cat #K4002)) to the tube with the tissue at a concentration of 1:5 (enzyme: tissue), followed by 1.25 hours shaking incubation at 37° C. The tube is centrifuged and the pellet is resuspended in 25-30 ml of high serum media (DMEM+25% Fetal Bovine Serum+1% Pen/Strep antibiotic+0.1% Gentamycin). DNAse is added and the tube is shaken vigorously and centrifuged to collect the sample. Spun supernatants are then panned onto 150 mm dishes with 25-30 ml media for 1.5 hours at 37° C. in the incubator. The cells are dislodged with 0.25% trypsin-EDTA when cells are at least 90% confluent, counted and seed onto CtCs. A sister culture of satellite cells is then created in collagen coated culture dishes. The cells are then characterized by immunolabeling for Pax 7, Myf5, MyoD, and sarcomeric myosin (MF20). In previous studies, the satellite cell cultures are 80+% positive for Pax7 and MyoD.

For generation of skeletal muscle stem cells, 30-50 collagen gels are prepared in 2 cm diameter circular wells as described above. Dispersed satellite cells (12×10$^6$ per well) are then applied to the well. The cells are allowed to attach and culture of the collagen substrate for 24 hours and then the gel is released as per standard practice for the disclosed invention. Alternately, the gels can be released after cell attachment is achieved, static or dynamic strain is then applied to generate preferred alignment and differentiation potential of the adherent cells. The gels (containing cells or no cells) can also be soaked for example in 100 µM JM peptide, assisting muscle regeneration by the stem cells.

Following a 24 hour period in culture, circular gels containing peptide and stem cells can then be stacked within a single well, each layer being adhered to the next by small dab of Cell-Tak™ at the gel edge. The cylindrical 3d assembly of gel layers of skeletal stem muscle cells then has a suture threaded through the middle of its long axis, removed from the culture well and then placed in the open excisional wound in the abdominal muscle of the rat. The suture thread through the cylinder of stem cells stabilizes the assembly and also is used to secure it in place. To increase the robustness of the repair multiple 3d tissue engineered constructs of satellite cells can be applied to the ventral hernia. The repair site is then covered with an appropriate surgical membrane and wound dressing to protect the wound and implanted tissue engineered device. Animals are then sampled at time points between initial wounding and 16 weeks.

In the rat model, inflammatory response, scarring and skeletal muscle regeneration can be assessed using histochemistry and immunohistochemistry (e.g., Pax7, MyoD, MF20 expression) of the repaired abdominal tissues using standard approaches. Functional assessment of live tissue from the repair can be done by taking regenerated muscle from the repair placing in a muscle bath, oxygenated (95% $O_2$ and 5% $CO_2$) Krebs solution maintained at 37° C. at pH 7.4, and undertaking physiological tests of muscle function: isometric contraction, length/tension relationship determination, and breaking stress and strain. In human subjects, closure of the hernia, assessments of scarring and restoration of abdominal muscle function as assessed by a qualified clinician would be undertaken. Small biopsies of the repair can also be taken for direct assessment of muscle regeneration by histology by a qualified histotechnologist under the supervision of a clinician. However, it would be advisable to keep such invasive diagnoses to a minimum. The provided composition can modulate the wound-healing response to a cellularized tissue engineered implant, promoting its integration and maintenance in the human body.

In another example, Silicone disks coated with either vehicle control or ACT1 peptide were implanted submuscularly into male Sprague-Dawley rats. Capsulectomies were performed on days 1, 2, 3, 14, and 28. The implant capsules and surrounding tissue were analyzed histologically and biochemically. The peptide modulated the wound-healing response to silicone implants by attenuating neutrophil infiltration, increasing vascularity of the capsule tissue, reducing type I collagen deposition around the implant, and reducing the continued presence of contractile myofibroblasts. The provided composition can thus provide an enabling technology for modulating the wound-healing response to implants, promoting integration of implanted materials and tissue-engineered devices in the human body.

Example 11

Uses in Cancer Treatment

Results described in Example 11 were published in part in abstract form as Zhu et al., 2007 at the Pediatric Academic Societies 2007 Annual Meeting, May 5-8, 2007, Toronto Canada, which is incorporated herein by reference.

The infiltration of glioma cells within the central nervous system (CNS) accounts for high rates of mortality and morbidity. This infiltration requires cellular attachment, cytoskeletal-dependent motility, and protease-dependent invasiveness. Recent research has revealed that a hallmark of many glioma cell lines is the aberrant expression of gap junctions, intercellular membrane channels that allow direct cell-to-cell communication. Gap junction channels are composed of protein subunits called connexins, which are maintained and organized by many scaffolding proteins and cytoskeletal components. One such scaffolding protein is zonula occludens-1 (ZO-1), which binds to the carboxyl terminus of connexin43 (Cx43), a major gap junction protein subtype.

In many malignant glioma cell lines, Cx43 gap junction organization may play important roles in tumorigenicity, and more specifically, in invasiveness. A peptide, called ACT-1 and based on the CT of Cx43, was designed to be a competitive inhibitor of Cx43 and ZO-1 interaction and has been previously shown to alter gap junction dynamics in fibroblasts. In this study, U87 MG glioblastoma cells (which express Cx43) treated with the peptide displayed a higher degree of aggregation, a significant aspect of tumor cell migration (FIG. 12). In contrast, the adhesive properties of the Cx43-deficient C6 glioma cell line did not change in response to peptide treatment. Interestingly, the C6 cells did display altered morphology after treatment with the peptide, suggesting that the peptide also influences cytoskeletal organization, another important factor in glioma migration. These results provide insight into the role of the Cx43 CT in malignancy. The provided composition can thus provide a new approach for cancer treatment.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure.

Example 12

JM2 Peptide Decreases Inflammation and Scarring and Promotes Regenerative Healing Associated with Silicon Implants Animals Harlan Sprague-Dawley (Indianapolis, Ind.) male rats weighing approximately 200-300 g were used throughout this work. Animals were managed in the institutional animal care facility in compliance with the Guide for the Care and Use of Laboratory Animals published by the National Academy of Sciences and all animal protocols were approved by the University of South Carolina Institutional Animal Care and Use Committee (IACUC).

JM2 Preparation

25% pluronic F127 gel (Sigma-Aldrich, St. Louis, Mo. 63103), which is liquid at 4° C., but gels at 37° C., was used as a delivery vehicle for JM2 peptide. Pluronic gel has mild surfactant properties that aid in peptide dispersion. The JM2 peptide was reconstituted in 1× PBS containing the 25% pluronic gel to a final concentration of 180 micomolar.

Implantation Procedure

Animals were anesthetized with 2.75% isoflurane balance oxygen gas. After achievement of general anesthesia, the surgical site consisting of the animal's upper back was prepped by clipping fur down to skin and applying betadine scrub solution in triplicate. Sterile towels were draped to define the surgical field. PWAS Silicone sensors (5 mm diameter) were autoclave sterilized and warmed to 37° C. prior to implantation. For the treatment group, implants were dipped twice in JM2 pluronic solution prior to implantation. For the vehicle control group, the implants were dipped in saline only. This coating procedure produced an even coating of the implant. A muscle pocket was created under the latissimus dorsi muscle and implants were inserted. 50 μl of the corresponding solution was also injected into the muscle pocket prior to closure. The muscles were reapproximated with 4-0 Prolene (Ethicon Inc, Somerville, N.J. 08876) and the skin closed with 4-0 Prolene and skin staples. Upon recovery from anesthesia animals were given a bolus of 3 ml normal saline subcutaneously and 0.1 mg/kg Buprenorphine HCl (Reckitt Benckiser Healthcare Ltd., Hull, England HU8 7DS) intra-muscularly to alleviate pain.

Capsule Morphometric Analysis

Nine animals were organized into three groups, 24 hours post implantation, 72 hours post implantation, and 4 weeks post implantation. In each group, three animals JM2 treatment and one control. PWAS Silicone disks (5 mm diameter) were implanted as previously described. At each time point post implantation, four animals from each group underwent capsulectomy to remove the implant and surrounding tissue capsule. The tissue was vibrotome sectioned and stained for H&E and Masson's trichrome. Three tissue sections from each animal were examined with light microscopy. FIG. 12 shows that presence of the JM2 peptide decreased inflammation and reduced skeletal muscle necrosis associated with a silicone implant in vivo. FIG. 13 shows that treatment with JM2 peptide improved healing and decreased capsule formation, scarring and fibrosis associated with the silicon implant, as well as promoting the longterm maintenance, and/or growth and regeneration of skeletal muscle and other tissues surrounding the silicone implant.

Example 13

JM1 and JM2 Peptides can Inhibit Cx43 Hemichannel Activity

The hypothesis that ACT1, JM1, and/or JM2 can inhibit Cx43 hemichannel activity, thereby preventing release of the inflammatory activator ATP, was tested in the following experiments. Data was generated regarding the mechanism of JM peptides on Cx43 GJ channels and hemichannels. The effect of JM2 on GJ channels was tested as follows. Cx43-HeLa cells were treated with 10 μM JM2 or vehicle for 2, 6, and 24 hrs in standard cell culture conditions. Vehicle treated controls were generated. The cells were labeled for Cx43, N-Cadherin, and the nucleus. Cells were fixed with 2% paraformaldehyde and labeled with Cx43 antibody, N-cadherin antibody (to indicate cell-cell apposing membranes), and Hoecsht nuclear stain. We observed typical punctate Cx43 GJs in control cells. In contrast, cells treated for 2 hrs with JM2 displayed little GJ labeling. Whether this lack of labeling is a result of changes in expression level or GJ formation will have to be address by Western analysis, as proposed below. Interestingly, GJ labeling began to return at 6 hrs, and appeared normal after 24 hrs. These data indicate that JM2 temporarily reduces cell-surface Cx43 in cultured cells. Similar results were observed with JM1 peptide.

As JM1 and JM2 are based on part of a putative juxtamembrane microtubule binding motif of Cx43, cells were also labeled for microtubules using an anti-α-tubulin antibody. The 2 hr time point was focused on as it seemed to have the greatest effect on Cx43 labeling. A decrease cell-surface Cx43 labeling in JM2 treated Cx43-HeLa cells, and what appeared to be an increase in intracellular Cx43 labeling, was again observed. Importantly, the inventors also observed disruption of microtubule organization. Since the JM region also shows homology to protein phosphatase interaction domains and thus additional complexity for the molecular mechanism may exist.

Figure 14:
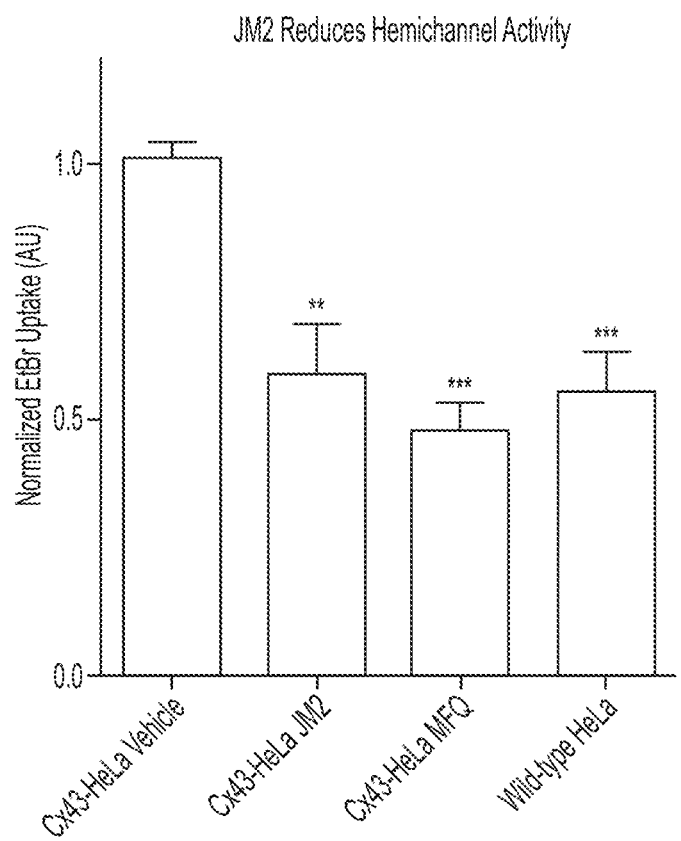
FIG. 14. JM2 reduces hemichannel activity. Cx43-HeLa and wild-type HeLa cells were treated with vehicle, and Cx43-HeLa cells were additionally treated with 50 µM JM2 or 25 µM mefloquine (MFQ) for 2 hrs. Cells were subjected to ethidium bromide (EtBr) assay for hemichannel activity as described in Rhett et al. (2011). These results represent the average of at least 4 experiments, and error bars=SEM. ANOVA with post-hoc analysis comparing pairs of data was used to determine significance.  $p<0.01$; * $p<0.001$ FIG. 15. ATP is released from endothelial cells in response to low $Ca^{2+}$ and the inflammatory cytokine IL-6. HMVECs were treated for 5 hours with either nothing or IL-6 (0.01 ng/mL). After the 5 hr incubation, HBSS (w/$Ca^{2+}$ and $Mg^{2+}$)-25 mM HEPES was added to one set of controls ("Control") and the IL-6 treated cells for 5 min. To the other set of control wells, HBSS (w/o $Ca^{2+}$ and $Mg^{2+}$)-25 mM HEPES was added as a positive control for Cx43 hemichannel-mediated ATP release ("Low $Ca^{2+}$"). The error bars represent the standard error for replicates within the same experiment.

These labeling studies only provided direct evidence for an effect of JM2 on GJ channels, not hemichannels. However, the observed increase in intracellular Cx43 labeling suggested the possibility that targeting microtubules with JM2 affects Cx43 trafficking to, or stability in, the membrane. Therefore, we proceeded to carry out studies on hemichannel activity as described for ACT1 in Rhett et al, 2011. The inventors found that JM2 was a highly effective hemichannel blocker (FIG. 14). Specifically, treatment of Cx43-HeLa cells with 50 μM JM2 for 2 hrs (as compared to 180 μM ACT1 for 2 hrs in Rhett et al., 2011), significantly reduced hemichannel activity to the level of wild-type HeLa cells (i.e., not expressing Cx43).

Figure 15:
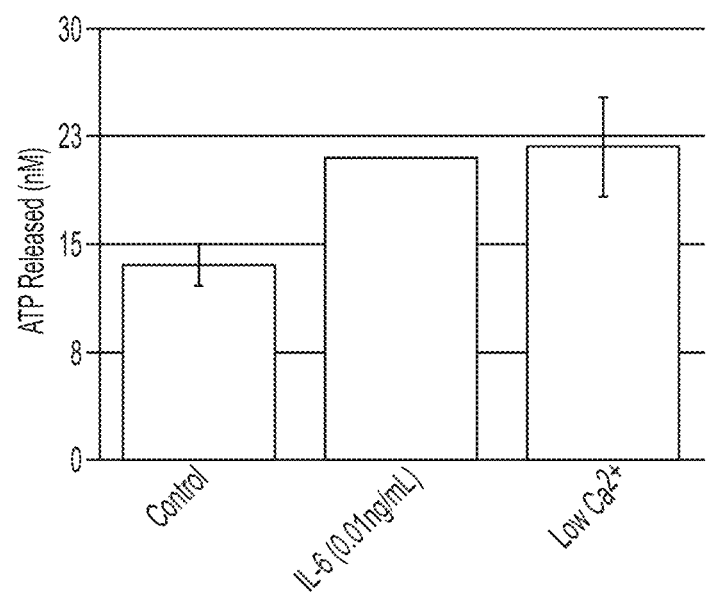

The possibility that Cx43 acts as a mediator of inflammation through hemichannel mediated release of ATP was further examined. Studies on ATP release in the HeLa cell models, as well as primary human microvascular endothelial cells (HMVECs), were performed. Endothelial cells were chosen as a model for ATP release because of their direct access to the blood stream, through which neutrophils have been demonstrated to migrate in response to injury-generated purinergic signaling (McDonald et al., 2010; Baroja-Mazo et al., 2013). The inventors observed increased ATP release in response to cellular stress in the form of low Ca2+, a widely used trigger for connexin hemichannel opening, and the inflammatory cytokine IL-6 (FIG. 15). However, the inventors also observed that, in preliminary experiments, ATP released in response to low $Ca^{2+}$ was not inhibited by treatment with mefloquine, a commonly used connexin channel blocker. Endothelial cells may also release ATP through vesicular exocytotic mechanisms in a $Ca^{2+}$ dependent manner (Bodin and Burnstock, 2001; McDonald et al., 2010). Pannexin channels, which can also mediate ATP release, are similarly sensitive to mefloquine (Lohman et al., 2012; Bodin et al, 2001).

Strategies for Promoting Survival of Satellite Cells Following Implantation

Cell transplantation therapies for muscle regeneration are currently challenged by low survival of implanted cells (typically 5-10%). aCT1, one of the compounds we use in this project, inhibits Cx43 hemichannel activity in the perinexus (Rhett et al., 2011; Rhett and Gourdie, 2012; Lohman et al., 2012). JM peptides may be used in a Cx43-based targeting approach. Similar to aCT1, JM peptides also potently reduce Cx43 hemichannel activity. The molecular mechanism of aCT1 and JM peptides may be distinct, raising the prospect for further increase in efficacy based on therapeutic approach combining the two novel compounds.

In addition to Cx43 hemichannel targeting to improve survival of engrafted cells, pre-aggregation of satellite cells prior to implantation into injured skeletal muscle may be performed. The effect of bone marrow stem cells, an 'immune-privileged' cell type, on the survival of implanted aggregates is also being examined. Satellite cells and bone marrow stem cells (BMSCs) were from adult rats and aggregates have been generated from satellite cells using Morgan molds. Satellite cell survival following engraftment of these aggregates in a rat model in vivo can be performed.

The addition of JM2 peptide can block the function of Cx43 hemichannels. In the control images, profound inflammatory infiltrate were seen. The border zone between the tissue reaction area and the intact skeletal muscle was ill defined with what appears to be continued necrosis of the native muscle. In contrast, exposure to a JM1 or JM2 peptide resulted in a substantially narrower tissue reaction zone. The border zone between the intact muscle and implant reaction area is much better defined with little continued muscle necrosis at 24 hours.

Figure 16:
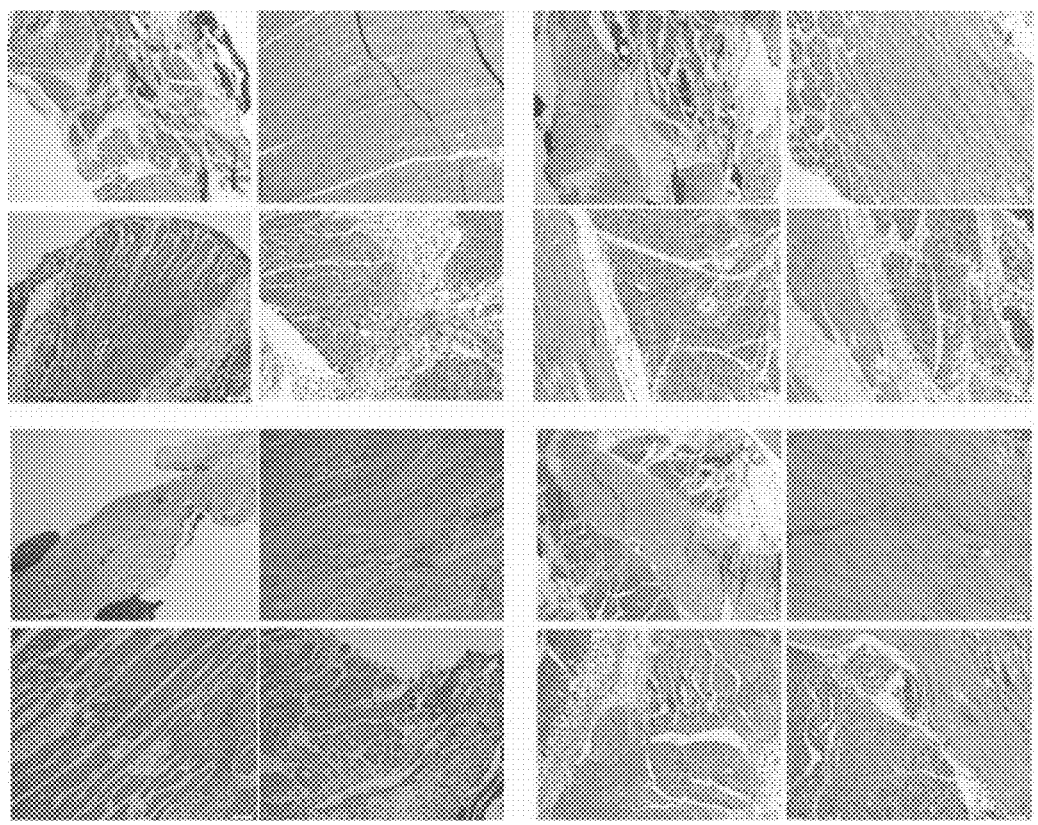
FIG. 16. A composite panel of microscopy images taken from H&E stained sections of muscle tissue adjacent to the silicon implant. Upper left—These images are of the implant alone the top left images is a low magnification image of the affected muscle tissue, as can be seen, there is significant inflammatory infiltrate as well as coagulative necrosis of the muscle fibers. The other images in the panel are high magnification showing areas of high inflammation and necrosis bottom two panels and relatively low inflammation away from the implant site, upper right. The top right set of images is from the tissue adjacent to the implant that had also been treated with exogenous ATP. As can be seen, there is profound inflammatory infiltrate and there are few areas without coagulative necrosis of the muscle tissue. Conversely, the bottom left panel shows the results of the addition of apyrase at the time of implantation. Similar to the addition of JM2 or ACT1 peptides, marked decrease in inflammatory infiltrate, well defined margins between healthy muscle and dying tissue, and less coagulative necrosis were seen. The bottom right panel is a demonstration of the effect of the addition of exogenous ATP to skeletal muscle. The mere presence of ATP causes significant inflammation. These data suggest that ATP is playing a significant role in targeting early inflammatory cells to the implant site. And that by modulating the ATP signal we can potentially modulate the initial inflammatory reaction.

15 male Sprague Dawley rats underwent unilateral implantation of silicon wafer implants. Three animals received implants only, three received implants plus exogenous ATP, three received implants plus exogenous apyrase, an enzyme that scavenges ATP, three underwent surgery alone without an implant, and three received a percutaneous injection of exogenous ATP into the latissimus dorsi muscle. The implants were harvested after 24 hours to evaluate the extent of inflammatory infiltrate and preservation of muscle. As can be seen in FIG. 16, top left panel, the implant alone causes significant inflammatory infiltrate as well as ill-defined boarder areas and coagulative necrosis of muscle fibers. The addition of exogenous ATP causes a profound increase in inflammatory infiltrate in the implant region, top right panel. Interestingly, treatment with apyrase at the implant site significantly reduced the inflammatory infiltrate. There are still some inflammatory cells present but there numbers are greatly reduced and the muscle is preserved, lower left panel. Finally, a simple percutaneous injection of ATP caused more inflammatory infiltrate than the surgery alone, further confirming our hypothesis that extracellular ATP plays a profound role in neutrophil targeting to damaged skeletal muscle tissue.

Example 14

Effect of Loss of Cx43 Function on STEMI Repair of Mechanically Active Skeletal Muscle Analysis of STEMI implants in the active skeletal muscle of the abdominal wall was performed. New muscle in the repair and reductions in the amount of scar tissue formation were observed. New skeletal muscle was generated that has fibrous scar tissue in-between most of the muscle fibers. The inventors hypothesized that there may be tissues that develop early on in development that are generic for the creation of vascular beds and for creating motor neuron connections. The inventors further hypothesized that these tissues may be affected by differentiating cells to proliferate and form blood vessels or motor neuron connections. For vascular bed formation, these cells can include endothelial cells and fibroblasts derived from the splanchnic mesoderm. To mimic this in an autologous transplant, stromal vascular fraction cells were isolated from adipose tissues and attempt to form endothelial cell tubule networks. For motor innervation, these cells were taken from the neural crest. The following data on STEMI repairs of active skeletal muscle was generated.

In attempting to quantify the neutrophil infiltrate using a myeloperoxidase stain, the inventors observed that some of the cells stained darker than others. Upon further investigation, these cells were not neutrophils as but rather were macrophages. The inventors further determined that at the 24 hour time point, untreated implants showed predominately neutrophils; however, when treated with ACT1 the primary inflammatory infiltrate was macrophages. This data supports the idea that the JM peptides can close Cx43 hemichannels and reduce or mute the ATP signal for inflammatory cell migration.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,610,795
U.S. Pat. No. 4,215,051
U.S. Pat. No. 4,554,101
U.S. Pat. No. 4,680,338
U.S. Pat. No. 4,684,611
U.S. Pat. No. 4,868,116
U.S. Pat. No. 4,897,268
U.S. Pat. No. 4,897,355
U.S. Pat. No. 4,946,778
U.S. Pat. No. 4,952,500
U.S. Pat. No. 4,980,286
U.S. Pat. No. 5,075,109
U.S. Pat. No. 5,141,648
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,552,157
U.S. Pat. No. 5,563,055
U.S. Pat. No. 5,563,250
U.S. Pat. No. 5,565,213
U.S. Pat. No. 5,567,434
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,725,871
U.S. Pat. No. 5,736,524
U.S. Pat. No. 5,738,868
U.S. Pat. No. 5,741,516
U.S. Pat. No. 5,756,353
U.S. Pat. No. 5,780,045
U.S. Pat. No. 5,780,448
U.S. Pat. No. 5,789,215
U.S. Pat. No. 5,795,587

U.S. Pat. No. 5,804,212
U.S. Pat. No. 5,880,270
U.S. Pat. No. 5,945,100
U.S. Pat. No. 5,981,274
U.S. Pat. No. 5,994,624
U.S. Pat. No. 6,261,834
U.S. Pat. No. 7,786,074
U.S. Patent Appln. US2011/0086068
U.S. Patent Appln. US2010/0286762
U.S. Patent Appln. US2008/067944
PCT Appln. PCT/US2008/067944
PCT Appln. WO 89/07136
PCT Appln. WO 90/02806
PCT Appln. WO 94/09699
PCT Appln. WO 95/06128
Almquist et al., *J. Med. Chem.*, 23:1392-1398, 1980.
Alonso L, Fuchs E. Stem cells in the skin: waste not, Wnt not. Genes Dev. 2003 May 15; 17(10):1189-200.
Ausubel et al., In: *Current Protocols in Molecular Biology*, John Wiley and Sons, 1994.
Bagshawe et al., *Br. J. Cancer,* 58:700-703, 1988.
Bagshawe, *Br. J. Cancer,* 60:275-281, 1989.
Banerji et al., *Cell,* 33(3):729-740, 1983.
Baroja-Mazo A, Barbera-Cremades M, Pelegrin P. The participation of plasma membrane hemichannels to purinergic signaling. Biochim Biophys Acta. 2013; 1828(1):79-93. doi: 10.1016/j.bbamem.2012.01.002. PubMed PMID: 22266266.
Battelli et al., *Cancer Immunol. Immunother.,* 35:421-425, 1992.
Ben-Bassat et al., *J. Bacteriol.,* 169:751-7, 1987.
Benner, *TIB Tech.,* 12:158-163, 1994.
Berkneret et al., *Virology,* 61:1213-1220, 1987.
Bittner et al., *Methods in Enzymol,* 153:516-544, 1987.
Bodanszky et al., *J. Antibiot.,* 29(5):549-53, 1976.
Bodin P, Burnstock G. Purinergic signalling: ATP release. *Neurochem Res.* 2001; 26(8-9):959-69. PubMed PMID: 11699948.
Boffa et al., *Circulation,* 100(18):1901-1908, 1999.
Borg et al., *Dev. Biol.,* 104:86-96, 1984.
Bout, *Human Gene Therapy,* 5:3-10, 1994.
Brigham et al. *Am. J. Resp. Cell. Mol. Biol.,* 1:95-100, 1989.
Brown and Burlingham, *J. Virol.,* 12:386-396, 1973.
Brown and Greene, *DNA Cell Biol.,* 10:6, 399-409, 1991.
Bucci et al., *Nat. Med.,* 6:1362-1367, 2000.
Buso, S.; Spiazzi, G.; Meneghini, M.; Meneghesso, G., "Performance Degradation of High-Brightness Light Emitting Diodes Under DC and Pulsed Bias," Device and Materials Reliability, IEEE Transactions on, vol. 8, no. 2, pp. 312-322, June 2008.
Cahill et al., *TIBS,* 14(10):400-403, 1989.
Caillaud, *Eur. J. Neuroscience,* 5:1287-1291, 1993.
Caruthers et al., *Nucleic Acids Symp. Ser.,* (7):215-223, 1980.
Chan, Y. F.; Moallem, M.; Wang, W., "Efficient implementation of PID control algorithm using FPGA technology," 2004. *CDC. 43rd IEEE Conference on Decision and Control*, vol. 5, no., pp. 4885-4890 Vol. 5, 14-17 Dec. 2004.
Chao-Hsuan Liu; Chun-Yu Hsieh; Yu-Chiao Hsieh; Ting-Jung Tai; Ke-Horng Chen, "SAR-Controlled Adaptive Off-Time Technique Without Sensing Resistor for Achieving High Efficiency and Accuracy LED Lighting System," Circuits and Systems I: Regular Papers, IEEE Transactions on, vol. 57, no. 6, pp. 1384-1394, June 2010.
Chardonnet and Dales, *Virology,* 40:462-477, 1970.
Chen and Okayama, *Mol. Cell Biol.,* 7(8):2745-2752, 1987.
Chen et al. *Invest. Ophthalmol. Vis. Sci.,* 50:2480, 2009.
Chow and Kempe, *Nucleic Acids Res.,* 9(12):2807-2817, 1981.
Colbere-Garapin et al., *Dev Biol Stand,* 50:323-326, 1981.
Cote et al., *Proc. Natl. Acad. Sci. USA,* 80(7):2026-2030, 1983.
Cotter and Robertson, *Curr. Opin. Mol. Ther.,* 5:633-644, 1999.
Crea and Horn, *Nucleic Acids Res.,* 8(10):2331-2348, 1980.
Creighton, In: *Proteins Structures And Molecular Principles*, W.H. Freeman and Co., N.Y. 50-60, 1983.
Creighton, In: *Proteins Structures And Molecular Principles*, W.H. Freeman and Co., NY, 34-49, 1983.
Creighton, In: *Proteins: Structure and Molecular Properties*, W. H. Freeman & Co., San Francisco, 79-86, 1983.
Dai et al., *Mol. Biol. Cell,* 218(6):2264-2273, 2007.
Davidson et al., *J. Virology,* 61:1226-1239, 1987.
Dawes et al., *Int. J. Biochem. Cell Biol.,* 28(2):229-238, 1996.
Derossi et al., *Biol. Chem.,* 269:10444-10450, 1994.
Dewan et al., HTRA1 promoter polymorphism in wet age-related macular degeneration. Science. 2006 Nov. 10; 314(5801):989-92.
"Electric Lighting consumption", The Solid State Lighting and Display Center, [Online] Available: http://ssld-c.ucsb.edu/consumption.php.
Eltzschig et al., *Circ. Res.,* 99(10):1100-1108, 2006.
European Appln. EP 45665 CA
Fawcett J W, Asher R A. The glial scar and central nervous system repair. Brain Res Bull. 1999 August; 49(6):377-91.
Fechheimer et al., *Proc. Natl. Acad. Sci. USA,* 84:8463-8467, 1987.
Feigner et al., *Proc. Natl. Acad. Sci. USA,* 84:7413-7417, 1987.
Fiers et al., *Nature,* 273:113, 1978.
Fischer et al., *J. Pept. Res.,* 55:163-172, 2000.
Fraley et al., *Proc. Natl. Acad. Sci. USA,* 76:3348-3352, 1979.
Frankel and Pabo, *Cell,* 55:1189-1193, 1988.
Fu et al., *J. Biol. Chem.,* 279(35):36943-36950, 2004.
Gao et al., *Bioorg. Med. Chem.,* 10:4057-4065, 2002.
Ghatnekar et al., *Regen. Med.,* 4(2):205-223, 2009.
Gomez-Foix et al., *J. Biol. Chem.,* 267:25129-25134, 1992.
Goodenough and Paul, *Nat. Rev. Mol. Cell Biol.,* 4(4):285-294, 2003.
Gopal, *Mol. Cell Biol.,* 5:1188-1190, 1985.
Graham and Van Der Eb, *Virology,* 52:456-467, 1973.
Green and Loewenstein, *Cell,* 55:1179-1188, 1988.
Greenway et al., *Gene,* 18:355-360, 1982.
Gresh et al., *Vis. Neurosci.,* 20(2):211-220, 2003.
Gulati, A., "Modulation Techniques for LED Dimming-AN49262", Application Note, Cypress Perform, Oct. 22, 2008.
Guzman, *Circulation,* 73:1201-1207, 1993.
Haj-Ahmad et al., *Virology,* 57:267-274, 1986.
Hann, *J. Chem. Soc Perkin Trans.,* I 307-314, 1982.
Harland and Weintraub, *J. Cell Biol.,* 101(3):1094-1099, 1985.
Hartman and Mulligan, *Proc. Natl. Acad. Sci. USA,* 85:8047-8051, 1988.
Hochuli et al., *Bio/Technology,* 6:1321-1325, 1988.
Holladay et al. *Tetrahedron. Lett.,* 24:4401-4404, 1983.
Hong and Clayman, *Cancer Res.,* 60:6551-6556, 2000.
Hruby *Life Sci.,* 31:189-199, 1982.
Huang et al., *J. Neurosci.,* 32(10):3333-3338, 2012.

Huang-Jen Chiu; Yu-Kang Lo; Jun-Ting Chen; Shih-Jen Cheng; Chung-Yi Lin; Shann-Chyi Mou, "A High-Efficiency Dimmable LED Driver for Low-Power Lighting Applications," Industrial Electronics, IEEE Transactions on, vol. 57, no. 2, pp. 735-743, February 2010.
Hudson et al., Int. J. Pept. Prot. Res., 14:177-185, 1979.
Hughes et al., Cancer Res., 49:6214-6220, 1989.
Hunter et al., Mol. Biol. Cell, 16(12):5686-5698, 2005.
Ibba and Hennecke, Bio/technology, 12:678-682 (1994.
Ibba, Biotech. Genetic Engineer. Rev., 13:197-216, 1995.
Inouye and Inouye, Nucleic Acids Res., 13:3101-3109, 1985.
Jaeger et al., Methods Enzymol., 183:281-306, 1989b.
Jaeger et al., Proc. Natl. Acad. Sci. USA, 86:7706-7710, 1989a.
R. James, Berry Jay, E. Harri, and Ronald R. Williams, "Light-Emitting Diodes as Sensors for Colorimetric Analyses," Appl. Spectrosc. 51, 1521-1524 (1997).
Jennings-White et al., Tetrahedron Lett., 23:2533, 1982.
Jones et al., In vivo measurement of neutrophil activity in experimental lung inflammation. Am J Respir Crit Care Med. 1994 June; 149(6):1635-9.
Kaeppler et al., Plant Cell Rep., 9:415-418, 1990.
Kaneda et al., Science, 243:375-378, 1989.
Kato et al, J. Biol. Chem., 266:3361-3364, 1991.
Kirshenbaum, J. Clin. Invest., 92:381-387, 1993.
Klein et al., Complement factor H polymorphism in age-related macular degeneration. Science. 2005 Apr. 15; 308(5720):385-9.
Kohler and Milstein, Nature, 256:495-497, 1975.
Laimins et al., Proc. Natl. Acad. Sci. USA, 78:993, 1981.
Le Gal La Salle et al., Science, 259:988-990, 1993.
Leung, C. Y., Mok, P. K. T. and Leung, K. N., "A 1-V integrated current mode boost converter in standard 3.3/5-V CMOS technologies," IEEE J. Solid-State Circuits, vol. 40, no. 11, pp. 2265-2274, November 2005.
Lin et al., J. Biol Chem., 270:14255-14258, 1995.
Rob Lineback, IC Insights, "Solid-state lighting set to boost LED growth," LED Magazine, May 2006, [Online] Available: http://ledsmagazine.com/articles/features/3/5/6/1, Department of Energy.
Litzinger and Huang, Biochimica. Biophysica. Acta, 1104:179-187, 1992.
Lohman A W, Billaud M, Isakson B E. Mechanisms of ATP release and signalling in the blood vessel wall. Cardiovasc Res. 2012; 95(3):269-80. doi: 10.1093/cvr/cvs187. PubMed PMID: 22678409; PubMed Central PMCID: PMC3400358.
Lu et al., FASEB J., Mar. 13, 2012 (ahead of print)
Lundberg et al., Biochem. Biophys. Res. Comm., 299, 2002.
Lusky et al., Mol. Cell. Biol., 3:1108, 1983.
Maniatis, et al., Molecular Cloning, A Laboratory Manual, Cold Spring Harbor Press, Cold Spring Harbor, N.Y., 1988.
Massie et al., Mol. Cell. Biol., 6:2872-2883, 1986.
McConlogue, Mol. Cell Biol., 6(8):2865-2871, 1986.
McDonald B, Pittman K, Menezes G B, Hirota S A, Slaba I, Waterhouse C C, et al. Intravascular danger signals guide neutrophils to sites of sterile inflammation. Science. 2010; 330(6002):362-6. Epub 2010/10/16. doi: 330/6002/362 [pii]10.1126/science.1195491. PubMed PMID: 20947763.
Millikan, Surg. Clin. N. Am., 83(5):1223, 2003.
Morley, Trends Pharm. Sci., 463-468, 1980.
Morris et al., Nat. Biotechnol., 19:1173-1176, 2001.
Morrison et al., Proc. Natl. Acad. Sci. USA, 81(21):6851-6855, 1984.
Morey, J. Clin. Invest., 92:1580-1586, 1993.
Moullier, Nat. Genetics, 4:154-159, 1993.
Mudge and Hughes, Br. J. Surg., 72:70-71, 1985.
Mulligan and Berg, Proc. Natl. Acad. Sci. USA, 78(4):2072-2076, 1981.
Mulligan and Berg, Science, 209:1422, 1980.
Mulligan, Science, 260:926-932, 1993.
Nabel et al., Science, 244(4910):1342-1344, 1989.
Needleman and Wunsch, J. MoL Biol., 48:443, 1970.
Neuberger et al., Nature, 312(5995):604-608, 1984.
Nicolau and Sene, Biochim. Biophys. Acta, 721:185-190, 1982.
Nicolau et al., Methods Enzymol., 149:157-176, 1987.
Norris et al., In: Periostin Inhibitory Compositions For Myocardial Regeneration, Methods Of Delivery, And Methods Of Using Same, 2008.
Norenberg M D. Astrocyte responses to CNS injury. J Neuropathol Exp Neurol. 1994, May; 53(3):213-20.
O'Hare et al., Proc. Natl. Acad. Sci. USA, 78: 1527, 1981.
Oehlke et al., Biochim. Biophys. Acta., 1414; 127-139, 1998.
Omirulleh et al., Plant Mol. Biol., 21(3):415-428, 1993.
O'Quinn et al., Circ Res., 108(6):704-715, 2011.
O'Regan et al., Gene, 77:237-251, 1989.
Osborne et al., Mol. Cell Biol., 4:1293, 1984.
Park et al., Proc. Natl. Acad. Sci. USA, 97:8245-8250, 2000.
Pearson and Lipman, Proc. Natl. Acad. Sci. USA, 85:2444, 1988.
Pietersz and McKenzie, Immunolog. Reviews, 129:57-80, 1992.
Pinner, D. J., Friend, R. H., and Tessler, N., "Transient electroluminescence of polymer light emitting diodes using electrical pulses," Journal of Applied Physics, vol. 86, no. 9, pp. 5116-5130, November 1999.
Pooga et al., FASEB 1, 12, 67-77, 1998.
Potrykus et al., Mol. Gen. Genet., 199(2):169-177, 1985.
Potter et al., Proc. Natl. Acad. Sci. USA, 81:7161-7165, 1984.
Pursiainen, Otto, Linder, Norbert; Jaeger, Arndt; Oberschmid, Raimund; Streubel, Klaus, "Identification of aging mechanisms in the optical and electrical characteristics of light-emitting diodes," Applied Physics Letters, vol. 79, no. 18, pp. 2895-2897, October 2001.
Ragot, J. Gen. Virology, 74:501-507, 1993.
Ram et al. Cancer Res., 53:83-88, 1993.
Remington: The Science and Practice of Pharmacy, 19$^{th}$ Ed., Gennaro (Ed.), Mack Publishing Company, Easton, Pa. 1995.
Remington: The Science and Practice of Pharmacy, 21$^{st}$ Ed., Lippincott Williams and Wilkins, 2005.
Remington's Pharmaceutical Sciences, 18th Ed. Mack Printing Company, 1289-1329, 1990.
"Reverse Biasing Photo Detectors", ILX Lightwave, [Online] Available: http://www.ilxlightwave.com/technotes/TN %203600-4%20REV02%20Reverse %20Biasing %20Photodetectors.pdf
Rhett J M, Jourdan J, Gourdie R G. Connexin 43 connexon to gap junction transition is regulated by zonula occludens-1. Molecular Biology of the Cell. 2011; 22(9): 1516-28. Epub 2011/03/18. doi: 10.1091/mbc.E10-06-0548. PubMed PMID: 21411628; PubMed Central PMCID: PMC3084674.
Rich, Human Gene Therapy, 4:461-476, 1993.
Rippe, et al., Mol. Cell Biol., 10:689-695, 1990.
Rizo and Gierasch, Ann. Rev. Biochem., 61:387, 1992.
Roessler, J Clin. Invest., 92:1085-1092, 1993.
Roffler et al., Biochem. Pharmacol, 42:2062-2065, 1991.
Rousselle et al., Mol. Pharmacol., 57:679-686, 2000.
Ruther et al., EMBO J, 2(10):1791-4, 1983.

Sahin-Toth et al., *Protein Sci.*, 3:240-247, 1994.
Sambrook et al., In: *Molecular cloning*, Cold Spring Harbor Laboratory Press, Cold Spring Harbor, N.Y., 2001.
Santerre et al., *Gene*, 30: 147-156, 1984.
Sawada et al., *Nature Cell Biol.*, 5:352-357, 2003.
Senter et al., *Bioconjugate Chem.*, 4:3-9, 1993.
Senter, et al., *Bioconjugate Chem.*, 2:447-451, 1991.
Seth et al, *J. Virol.*, 51:650-655, 1984.
Seth et al., *Mol. Cell. Biol.*, 4:1528-1533, 1984.
Smith and Moss, *Gene*, 25(1):21-8, 1983.
Smith and Waterman, *Adv. Appl. Math.*, 2:482, 1981.
Soder et al., *Plast. Reconstr. Surg.*, 123(5):1440-1451, 2009.
Southern and Berg, *J. Molec. Appl. Genet.*, 1:327, 1982.
Spatola et al., *Life Sci.*, 38:1243-1249, 1986.
Spatola, In: *Chemistry and Biochemistry of Amino Acids, Peptides, and Proteins*, Weinstein (Ed.), Marcel Dekker, N.Y., 267, 1983a.
Spatola, In: *Peptide Backbone Modifications*, 1:3, (general review), 1983b.
Sribnick et al., *J. Neurosci. Res.*, 84(5):1064-1075, 2006.
Steigerwald, D. A.; Bhat, J. C.; Collins, D.; Fletcher, R. M.; Holcomb, M. O.; Ludowise, M. J.; Martin, P. S.; Rudaz, S. L., "Illumination with solid state lighting technology," Selected Topics in Quantum Electronics, IEEE Journal of, vol. 8, no. 2, pp. 310-320, March/April 2002.
Sugden et al., *Mol. Cell. Biol.*, 5:410-413, 1985.
Sun et al., *Nat. Genetics*, 8:33-41, 1994.
Svensson and Persson, *J. Virol.*, 55:442-449, 1985.
Takeda et al., *Nature*, 314(6010):452-454, 1985.
Takenaga et al., *J. Control Release*, 52(1-2):81-87, 1998.
Tence et al., *Cell Signal*, 24(1):86-98, 2012.
Thorson et al., *Methods in Molec. Biol.*, 77:43-73, 1991.
King Tong Lau, Susan Baldwin, Roderick L. Shepherd, Paul H. Dietz, William. S. Yerzunis, and Dermot Diamond, "Novel fused-LEDs devices as optical sensors for colorimetric analysis," Talanta, Volume 63, Issue 1, Molecular Recognition and Chemical Sensors, pp. 167-173, 10 May 2004.
Toyofuku et al., *J. Biol. Chem.*, 273(21):12725-12731, 1998.
Tur-Kaspa et al., *Mol. Cell Biol.*, 6:716-718, 1986.
"Using Light Emitting Diodes, Solid State Lighting", Department of Energy, [Online] Available: http://www1.eere.energy.gov/buildings/ssl/using_leds.html.
Van Heeke and Schuster, *J. Biol. Chem.*, 264(33):19475-19477, 1989.
Varga et al., *J. Virol.*, 65:6061-6070, 1991.
Verma, In: *Microbiology*, American Society for Microbiology, 229-232, Washington, 1985.
Vigneron et al., *Proc. Natl. Acad. Sci. USA*, 93:9682-9686, 1998.
Wai-Keung Lun; Loo, K. H.; Siew-Chong Tan; Lai, Y. M.; Tse, C. K., "Bilevel Current Driving Technique for LEDs," Power Electronics, IEEE Transactions on, vol. 24, no. 12, pp. 2920-2932, December 2009.
Wawrzynczak and Thorpe, In: *Immunoconjugates, Antibody Conuugates In Radioimaging And Therapy Of Cancer*, Vogel (Ed.), NY, Oxford University Press, 28, 1987.
Wei Zhao; Byung Hwa Kim; Larson, A. C.; Voyles, R. M., "FPGA implementation of closed-loop control system for small-scale robot," Advanced Robotics, 2005. ICAR '05. Proceedings., 12th International Conference on, vol., no., pp. 70-77, 18-20 Jul. 2005.
Wickham et al., *Cell*, 73:309-319, 1993.
Wigler et al., *Proc. Natl. Acad. Sci. USA*, 77(6):3567-3570, 1980.
Wilgus et al., Reduction of scar formation in full-thickness wounds with topical celecoxib treatment. Wound Repair Regen. 2003 January-February; 11(1):25-34.
Wilson et al., *Science*, 244:1344-1346, 1989.
Wing Yan Leung; Tsz Yin Man; Mansun Chan, "A high-power-LED driver with power-efficient LED-current sensing circuit," Solid-State Circuits Conference, 2008. ESSCIRC 2008. 34th European, vol., no., pp. 354-35'7, 15-19 Sep. 2008.
Wolff et al., *Science*, 247:1465-1468, 1990.
Wolff, *Nature*, 352:815-818, 1991.
Wong et al., *Gene*, 10:87-94, 1980.
Wu and Wu, *Biochemistry*, 27: 887-892, 1988.
Wu and Wu, *J. Biol. Chem.*, 262:4429-4432, 1987.
Yang et al., A variant of the HTRA1 gene increases susceptibility to age-related macular degeneration. Science. 2006 Nov. 10; 314(5801):992-3.
Yuequan Hu; Jovanovic, M. M., "LED Driver With Self-Adaptive Drive Voltage," Power Electronics, IEEE Transactions on, vol. 23, no. 6, pp. 3116-3125, November 2008.
Zabner, *Cell*, 75:207-216, 1993.
Zabner, *Nat. Genetics*, 6:75-83, 1994.
Zhang, *BioTechniques*, 15:868-872, 1993.
Zhang et al., 2001 replaces Almer
Zhang et al., Interaction between krit1 and icap1alpha infers perturbation of integrin beta1-mediated angiogenesis in the pathogenesis of cerebral cavernous malformation. Hum Mol Genet. 2001 Dec. 1; 10(25):2953-60.
Zoller, *Curr. Opinion Biotech.*, 3:348-354, 1992.
Zuker, *Science*, 244:48-52, 1989.

What is claimed is:

1. A method of treating a cancer in a subject, comprising administering to the subject a pharmacologically effective dose of an isolated peptide, wherein the peptide is less than 50 amino acids in length and comprises JM1 (VFFKGVKDRV; SEQ ID NO:1) or JM2 (VFFKGVKDRVKGKSD; SEQ ID NO:2), or a sequence having at least 90% sequence identity to JM1 (SEQ ID NO:1) or JM2 (SEQ ID NO:2); wherein the cancer is a glioblastoma, colon cancer, or a pancreatic cancer.

2. The method of claim 1, wherein the cancer is a pancreatic cancer.

3. The method of claim 1, wherein the cancer is a glioblastoma.

4. The method of claim 1, wherein the subject is a human.

5. The method of claim 1, wherein the peptide is coupled to a cell penetrating peptide or a cell internalization peptide.

6. The method of claim 5, wherein the cell penetrating peptide is a polyarginine, penetratin, an Antennapedia sequence, TAT, HIV-Tat, Antp-3A (Antp mutant), Buforin II, Transportan, MAP (model amphipathic peptide), K-FGF, Ku70, prion, pVEC, Pep-I, SynB1, Pep-7, HN-1, BGSC (Bis-Guanidinium-Spermidine-Cholesterol), or BGTC (Bis-Guanidinium-Tren-Cholesterol).

7. The method of claim 6, wherein the cell penetrating peptide is a polyarginine.

8. The method of claim 7, wherein the polyarginine consists of five to nine arginine residues, wherein a plurality of the arginine residues in the polyarginine are D-isomers of arginine.

9. The method of claim 7, wherein the polyarginine consists of RRRRRRRR (SEQ ID NO:3), wherein the arginine residues in the polyarginine are D-isomers of arginine.

10. The method of claim 8, wherein the peptide consists of the sequence rrrrrrrrVFFKGVKDRVKGRSD (SEQ ID NO:4).

11. The method of claim 8, wherein the peptide consists of the sequence rrrrrrrrVFFKGVKDRV (SEQ ID NO:5).

12. The method of claim 1, wherein the peptide does not comprise a cell penetrating peptide sequence or a cell internalization peptide.

13. The method of claim 12, wherein the peptide consists of VFFKGVKDRVKGKSD (SEQ ID NO: 6).

14. The method of claim 12, wherein the peptide consists of VFFKGVKDRV (SEQ ID NO: 7).

15. The method of claim 1, wherein the peptide is comprised in a pharmaceutical preparation.

16. The method of claim 15, wherein said pharmaceutical preparation comprises from about 0.001-10% w/v or v/v of the peptide.

17. The method of claim 15, said pharmaceutical preparation comprises from about 0.1 μM to about 1000 μM of the peptide.

18. The method of claim 15, wherein the pharmaceutical preparation further comprises a second therapeutic agent.

19. The method of claim 18, wherein the second therapeutic agent is a chemotherapeutic.

20. The method of claim 19, wherein the second chemotherapeutic is cisplatin, paclitaxel, or carmustine.

21. The method of claim 1, wherein the cancer is a metastatic cancer.

22. The method of claim 1, wherein the cancer is a colonic carcinoma.

* * * * *